US009611514B2

(12) United States Patent
Dziembowski et al.

(10) Patent No.: US 9,611,514 B2
(45) Date of Patent: Apr. 4, 2017

(54) METHOD FOR SELECTION OF HDIS3 PIN DOMAIN INHIBITORS AND USE OF HDIS3 PIN DOMAIN INHIBITORS FOR CANCER TREATMENT

(71) Applicants: INSTYTUT BIOCHEMII I BIOFIZYKI POLSKIEJ AKADEMII NAUK, Warsaw (PL); ONCOARENDI THERAPEUTICS SP ZOO, Warsaw (PL); MIEDZYNARODOWY INSTYTUT BIOLOGII MOLEKULARNEJ I KOMORKOWEJ W WARSZAWIE, Warsaw (PL)

(72) Inventors: Andrzej Dziembowski, Warsaw (PL); Rafal Tomecki, Warsaw (PL); Karolina Drazkowska, Warsaw (PL); Roman Szczesny, Warsaw (PL); Krystian Stodus, Warsaw (PL); Weronika Jonko, Warsaw (PL); Marcin Nowotny, Warsaw (PL); Adam Golebiowski, Warsaw (PL); Jacek Olczak, Lodz (PL)

(73) Assignees: INSTYTUT BIOCHEMII I BIOFIZYKI POLSKIEJ AKADEMII NAUK, Warsaw (PL); ONCOARENDI THERAPEUTICS SP ZOO, Warsaw (PL); MIEDZYNARODOWY INSTYTUT BIOLOGII MOLEKULARNEJ I KOMORKOWEJ W WARSZAWIE, Warsaw (PL)

( * ) Notice: Subject to any disclaimer, the term of this patent is extended or adjusted under 35 U.S.C. 154(b) by 0 days.

(21) Appl. No.: 14/892,000

(22) PCT Filed: May 20, 2014

(86) PCT No.: PCT/IB2014/061558
§ 371 (c)(1),
(2) Date: Nov. 18, 2015

(87) PCT Pub. No.: WO2014/188337
PCT Pub. Date: Nov. 27, 2014

(65) Prior Publication Data
US 2016/0090639 A1 Mar. 31, 2016

Related U.S. Application Data

(60) Provisional application No. 61/825,739, filed on May 21, 2013.

(30) Foreign Application Priority Data

May 21, 2013 (PL) .................... P.403980

(51) Int. Cl.
C12Q 1/68 (2006.01)
C12Q 1/18 (2006.01)
G01N 33/573 (2006.01)
G01N 33/50 (2006.01)
A61K 31/472 (2006.01)
C12N 15/81 (2006.01)

(52) U.S. Cl.
CPC .......... C12Q 1/6897 (2013.01); A61K 31/472 (2013.01); C12N 15/81 (2013.01); C12Q 1/18 (2013.01); G01N 33/5008 (2013.01); G01N 33/5011 (2013.01); G01N 33/5038 (2013.01); G01N 33/573 (2013.01); G01N 2333/916 (2013.01); G01N 2333/922 (2013.01); G01N 2500/04 (2013.01); G01N 2500/10 (2013.01)

(58) Field of Classification Search
None
See application file for complete search history.

(56) References Cited

U.S. PATENT DOCUMENTS

2002/0064784 A1* 5/2002 Friend .................... C12Q 1/025
435/6.11

OTHER PUBLICATIONS

Chapman et al. Nature Mar. 2011 467-472.*
Hiroaki et al. PLoS ONE Mar. 2007 e317 1-12.*
International Preliminary Report on Patentability dated May 22, 2015, which issued during prosecution of International Application No. PCT/IB2014/061558.
International Search Report dated Sep. 24, 2014, which issued during prosecution of International Application No. PCT/IB2014/061558.
Chapman, et al. "Initial genome sequencing and analysis of multiple myeloma" Nature, Mar. 2011, 471(7339):467-472.
Murakami, et al. "Ribonuclease Activity of Dis3 is Required for Mitotic Progression and Provides a Possible Link between Heterochromatin and Kinetochore Function" PLoS ONE, Mar. 2007, 2(3):e317.
Papandreou, et al. "Identification of an Ire1alpha endonuclease specific inhibitor with cytotoxic activity against human multiple myeloma" Blood, Jan. 2011, 117(4):1311-1314.
Schaeffer, et al. "The exosome contains domains with specific endoribonuclease, exoribonuclease and cytoplasmic mRNA decay activities" Nature Structural & Molecular Biology, Jan. 2009, 16(1):56-62.
Sun, et al. "Catalytic mechanism of *Escherichia coli* ribonuclease III: kinetic and inhibitor evidence for the involvement of two magnesium ions in RNA phosphodiester hydrolysis" Nucleic Acids Research, Feb. 2005, 33(3):807-815.

* cited by examiner

Primary Examiner — Jeffrey S Lundgren
Assistant Examiner — Michael Schmitt
(74) Attorney, Agent, or Firm — Vedder Price P.C.; Thomas J. Kowalski; Deborah L. Lu

(57) ABSTRACT

The present invention relates to a method for selection or screening of hDIS3 PIN domain inhibitors, yeast strain and cell line used in such methods It also relates to new therapeutic agents selected hDIS3 PIN domain inhibitors and uses thereof in the treatment of cancers having mutations inhDIS3 RNB domain, especially multiple myeloma. The invention also relates to composition comprising new therapeutic agent hDIS3 PIN domain inhibitor and method for inducing synthetic lethality in a cancer cell.

18 Claims, 15 Drawing Sheets

FIG. 1A
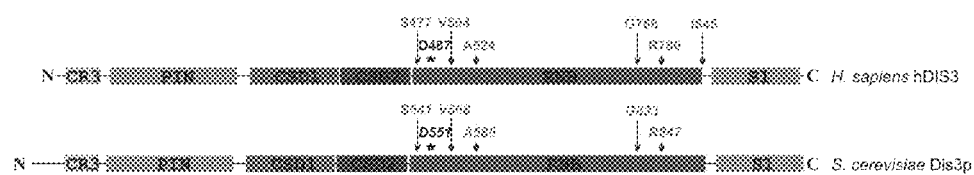
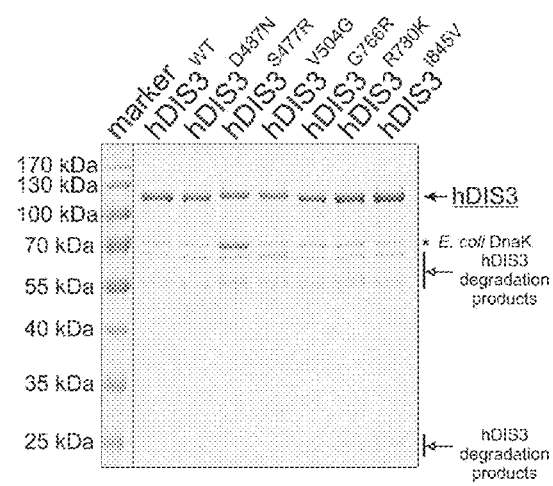
FIG. 1B
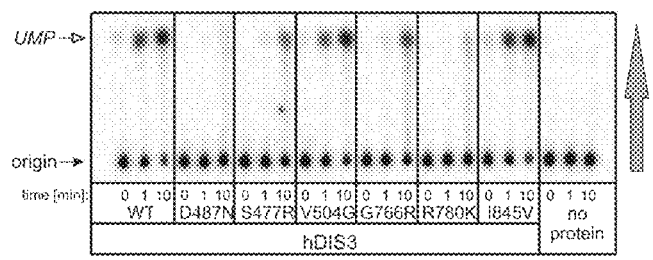
FIG. 1C

FIG. 3A
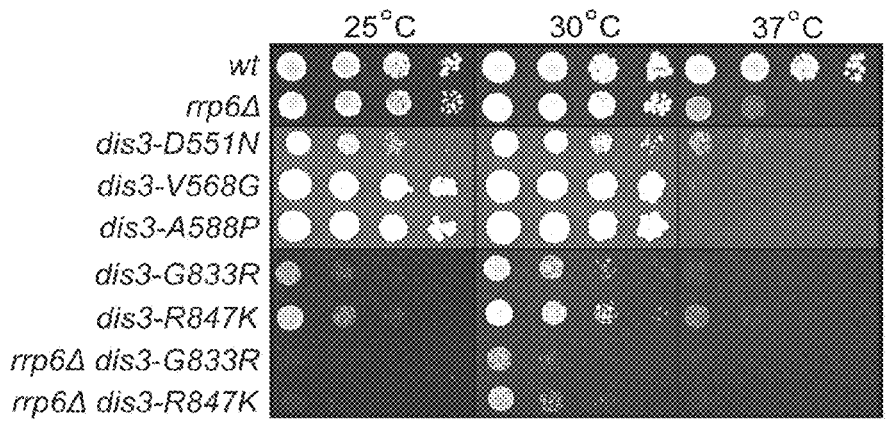
FIG. 3B
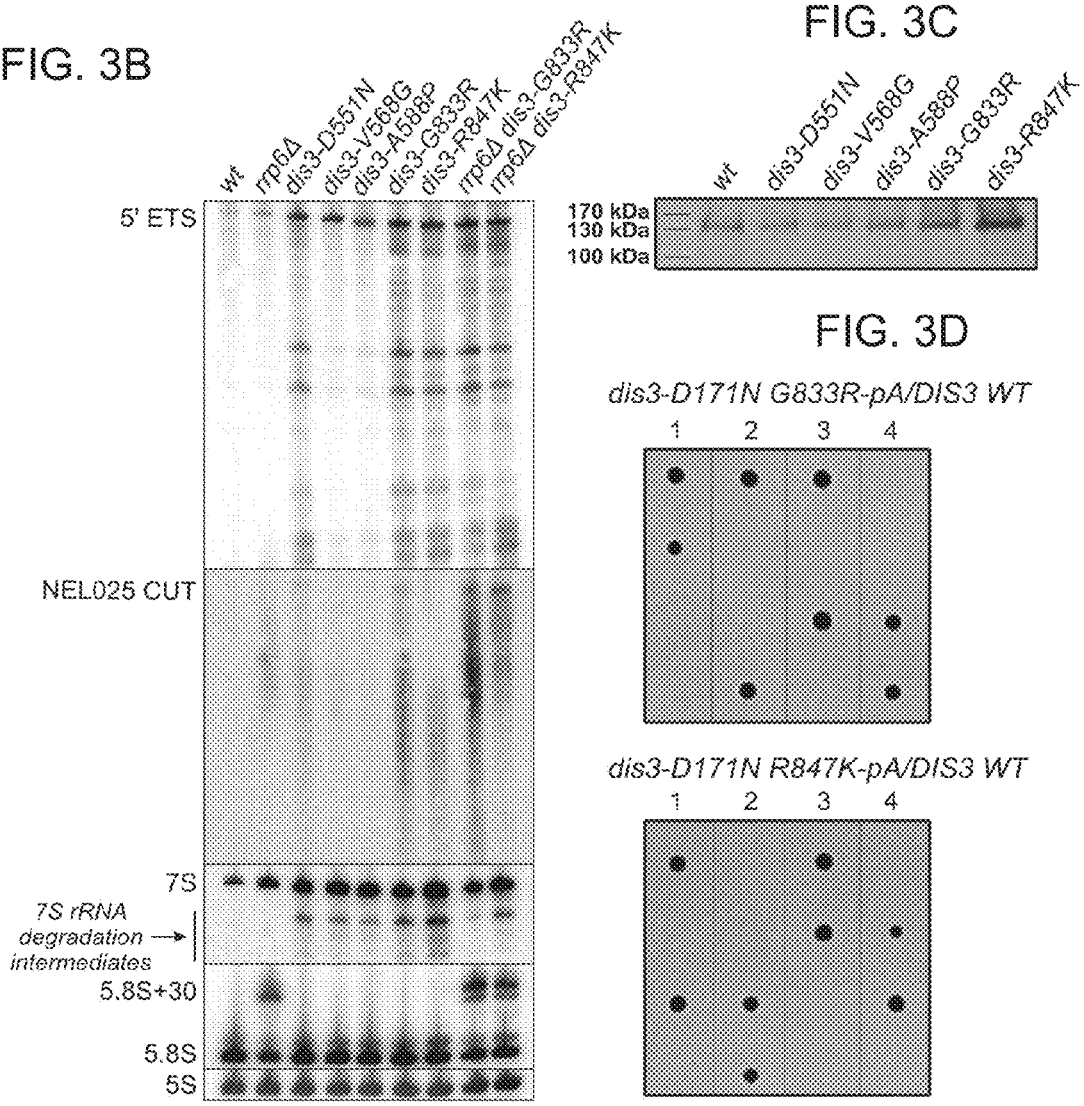
FIG. 3C
FIG. 3D

FIG. 9A
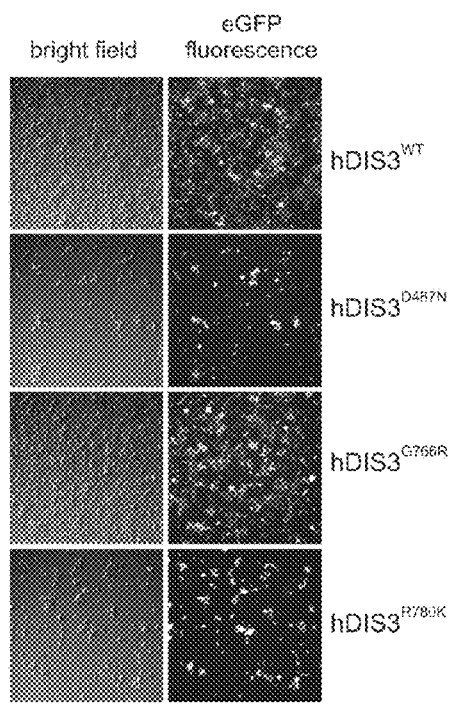
FIG. 9B
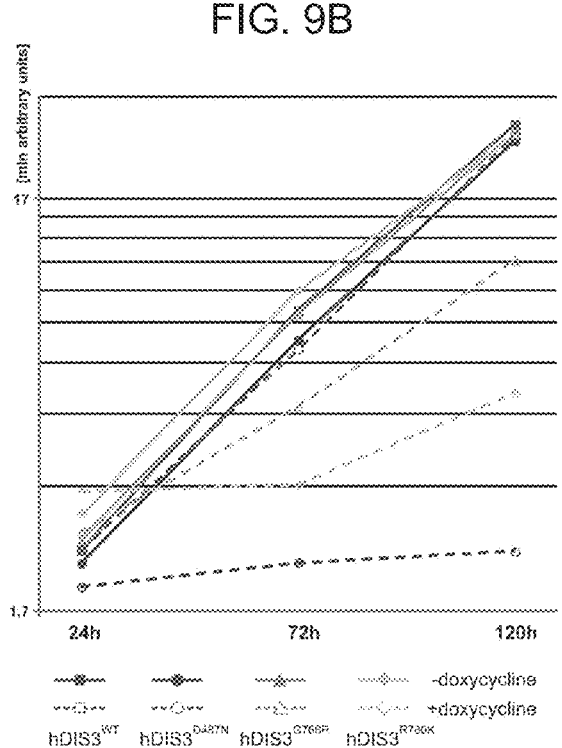
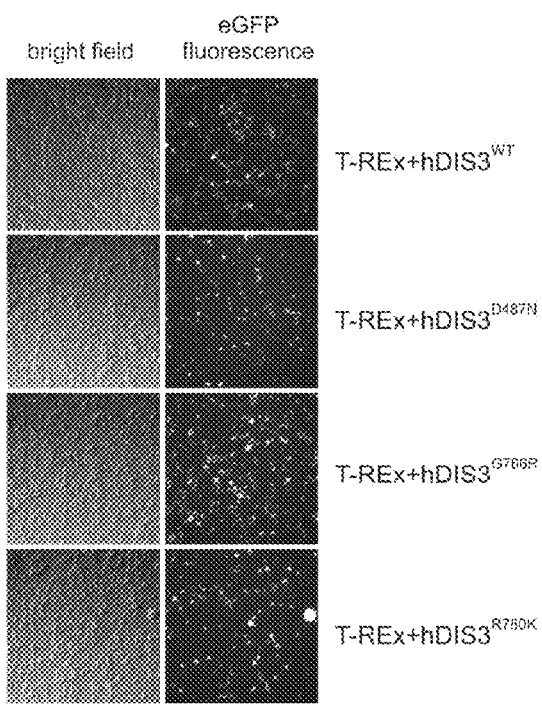
FIG. 9C

FIG. 10A
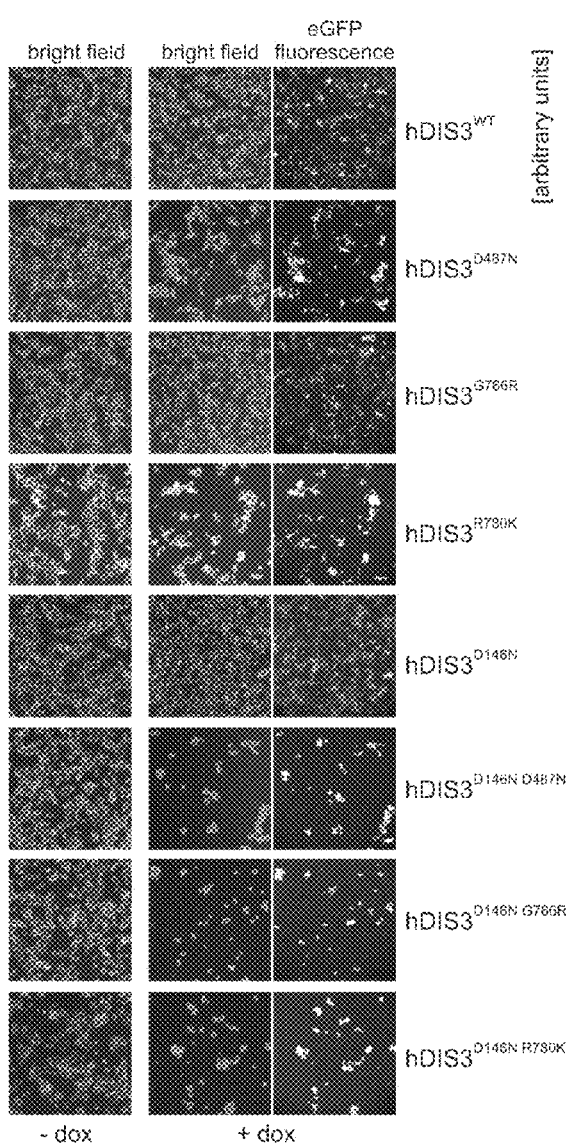
FIG. 10B
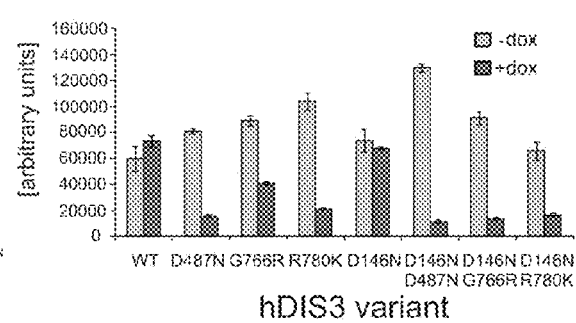
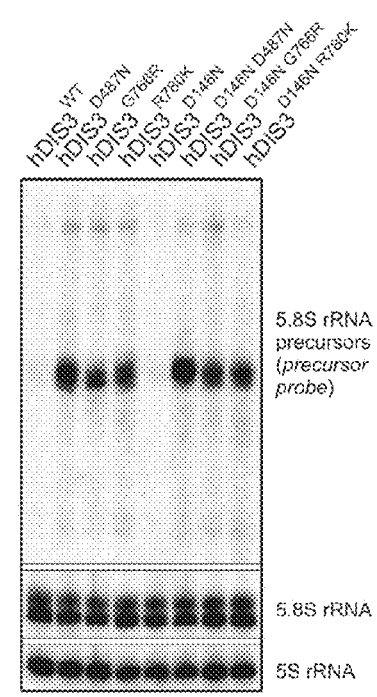
FIG. 10C

METHOD FOR SELECTION OF HDIS3 PIN DOMAIN INHIBITORS AND USE OF HDIS3 PIN DOMAIN INHIBITORS FOR CANCER TREATMENT

The present application is filed pursuant to 35 U.S.C.§371 as an U.S. National Phase Application of International Patent Application No. PCT/IB2014/061558 filed on May 20, 2104, which published as PCT Publication No. WO 2014/188337 on Nov. 27, 2014, which claims benefit of Polish Patent Application Number P.403980 filed May 21, 2013 and U.S. Provisional Application No. 61/825,739 filed May 21, 2013.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Nov. 18, 2015, is named 45981_01_2001_SL.txt and is 35,208 bytes in size.

DESCRIPTION

Technical Field

The present invention relates to a method of selection of hDIS3 PIN domain inhibitors, yeast strains and cell lines used in such methods. It also relates to new therapeutic agents selected hDIS3 PIN domain inhibitors and uses thereof in the treatment of cancers having mutations in hDIS3 RNB domain, especially multiple myeloma. The invention also relates to composition comprising new therapeutic agent hDIS3 PIN domain inhibitor and method for inducing synthetic lethality in a cancer cell.

The invention also relates to the methods of selection and screening for hDIS3 PIN domain inhibitors, as well as to the methods of screening of cancer patients, like multiple myeloma for the susceptibility of cancer cells to synthetic lethality with hDIS3 PIN domain catalytic inhibition.

Background Art

Synthetic lethality has recently emerged as one of the most promising strategies for development of targeted cancer therapies (Porcelli et al. 2012). Such a strategy enables the targeting of cancer cells with a potentially low effect on untransformed cells. For example, breast cancer cells with mutations in the BRCA1 and BRCA2 are very sensitive to inhibition of poly [ADP-ribose] polymerase (PARP1), whereas inhibition of PARP1 has little influence on survival and proliferation of normal cells with wild-type BRCA (Bryant et al. 2005; Farmer et al. 2005). Lead compounds based on PARP1 inhibitors are in advanced clinical trials (Barber et al. 2013).

Multiple myeloma (MM) is a lethal neoplastic disease which accounts for over 1% of all tumors, 10-15% of hematologic malignances, and 20% of deaths related to cancer of the blood and bone marrow (Laubach et al. 2011). It is difficult to treat and no successful therapy has been found up to this time.

The genetic background of MM is not completely understood. In up to 90% of MM patients chromosomal abnormalities are detected.

Recent publication describing whole-genome sequencing of 38 MM patients provided a global view on the somatic mutations associated with this cancer (Chapman et al. 2011). Approximately 50% of patients had either NRAS or KRAS activating mutations placing them together with chromosomal translocations as major prerequisites for development of MM. Unexpectedly, hDIS3 gene, not previously described as proto-oncogene or tumor suppressor was frequently mutated in the MM patients. hDIS3 protein is a well described catalytic subunit of the exosome complex, which plays a crucial role in eukaryotic RNA processing and decay (see below) (Chapman et al. 2011). High frequency of hDIS3 gene mutations in MM patients has been lately confirmed in another high-throughput study (Walker et al. 2012).

Interestingly, hDIS3 gene mutations were also found in global screens dedicated to other types of cancer, like medulloblastoma (in this case it was a true catalytic mutation changing D479 to V, which disrupts coordination of the $Mg^{2+}$ ion thereby abolishing hDIS exonucleolytic activity) and several cases of acute myeloid leukaemia (including a substitution of another aspartate in the active site: D488N) (Parsons et al. 2011; Ding et al. 2012). Additionally, hDIS3 was identified in transcriptomic analyses as one of the genes, whose expression differentiates superficial spreading melanoma from nodular melanoma (Rose et al. 2011). Furthermore, hDIS3 overexpression was earlier observed in human colorectal cancer and in a mouse model of this cancer, where elevated levels of respective mRNA and protein positively correlated with the incidence of metastasis (Lim et al. 1997; Liang et al. 2007). Very recently, functional genomics study defined hDIS3 as one of several genes essential for the growth maintenance of colorectal cancer cell lines (Camps et al. 2013).

The eukaryotic RNA decay and processing pathways are the essential components of the regulation of gene expression. RNA turnover is a crucial part of the cell homeostasis.

The exosome complex, which catalyzes 3'-5' exonucleolytic RNA degradation, is a primary eukaryotic ribonuclease that plays a fundamental role in virtually all pathways of RNA turnover (Lebreton & Séraphin, 2008; Schmid & Jensen, 2008; Tomecki et al. 2010a). Altogether, it participates in: turnover of normal mRNAs and AU-rich elements-regulated decay of unstable mRNAs (Gherzi et al. 2004; Mukherjee et al. 2002); nuclear processing of stable RNA classes (snRNA, snoRNA, rRNA, tRNA) (Allmang et al. 1999; Gudipati et al. 2012); degradation of unstable transcripts arising from intergenic regions, whose presence was discovered in exosome mutants (Wyers et al. 2005); complete degradation of mRNA after endonucleolytic cleavage initiated by siRNA in RNA interference pathway (Orban and Izaurralde, 2005). Furthermore, the exosome complex plays a crucial role in quality control of RNA both in the nucleus and the cytoplasm. It participates in such cytoplasmic RNA quality control pathways as the degradation of transcripts containing premature stop codons (NMD, nonsense-mediated decay), lacking stop codon (NSD, non-stop decay), or mRNAs with some steric obstacles, which cause ribosome stalling during translation (NGD, No-Go decay) (Allmang et al. 1999; Allmang et al. 2000; Assenholt et al. 2008; Gudipati et al. 2012; Isken & Maquat, 2007; Kadaba et al. 2004; Parker, 2012; Wang et al. 2008). Most importantly, it is a primary enzyme responsible for the degradation of unwanted molecules in the nucleus, including improperly processed pre-mRNAs, rRNAs and tRNAs and precursors of their synthesis. An interesting function of the exosome is in suppressing pervasive transcription since in exosome mutants huge amount of RNAs arising from intergenic and antisense regions accumulate (Preker et al. 2008; Lubas et al. 2011). Some of such transcripts have regulatory functions and participate in chromatin silencing of the genes located near sites they arise from (Camblong et al. 2007).

hDIS3 protein is a catalytic subunit of the RNA exosome complex, which plays a crucial role in RNA processing and decay. The exosome complex has an evolutionarily conserved structure. It is composed of 9-subunit ring, which despite homology to archaeal and bacterial phosphorolytic ribonucleases is devoid of any detectable catalytic activity (Liu et al. 2006; Dziembowski et al. 2007). The catalytically-inactive central exosome channel formed by the ring subunits has important functions in the regulation of ribonucleolytic activities of the complex (Wasmuth & Lima, 2012; Drazkowska et al. 2013), which are supplied entirely by associated catalytic subunits. Ribonucleases responsible for the enzymatic activity of the exosome belong to two different families: Dis3-like proteins are similar to bacterial RNases II/R while Rrp6-like subunits are members of RNase D family (reviewed in Tomecki et al. 2010a). The exosome was discovered in yeast and the majority of the research work has been done using this model system (Mitchell et al. 1997). In yeast genome there are single genes coding for Dis3 and Rrp6 proteins. Dis3 is the only essential catalytic subunit being present both in the nucleus and the cytoplasm. This multidomain protein is endowed with two different catalytic activities: 3'-5' exonucleolytic one residing in RNB domain and endonucleolytic one arising from the N-terminal PIN domain (Dziembowski et al. 2007; Lebreton et al; 2008, Schaeffer et al. 2009; Schneider et al; 2009). Dis3 exonuclease active site is located near the bottom of the central channel of the 9-subunit ring through which substrates are delivered (Bonneau et al. 2009; Malet et al. 2010). Both activities cooperate with each other but the exo one is more important for the cell physiology (Lebreton et al. 2008; Schaeffer et al. 2009; Schneider et al. 2009). Rrp6 is restricted to the nucleus and is responsible for only a subset of nuclear exosome functions. The exosome does not function on its own and needs appropriate cofactors for its full activity and efficient recognition of multiple substrates. The central components of all cofactors are RNA helicases, which are believed to transfer the substrate into the central channel of the ring, which then delivers RNA to Dis3 exonucleolytic active site.

There are important differences between human and yeast exosomes despite the well conserved structure, especially in the properties of the catalytic subunits. Human genome encodes two proteins—hDIS3 and hDIS3L, which contain all Dis3 elements including newly discovered CR3 motif and a structurally intact PIN domain required for the interaction with the 9-subunit ring (Tomecki et al. 2010b; Staals et al. 2010; Schaeffer et al. 2012). Proteomic analyses confirmed that both hDIS3 and hDIS3L interact with the human exosome ring, most probably in mutually exclusive manner. Notably, both human Dis3 homologues are processive 3'-5' hydrolytic exonucleases, whereas only hDIS3 has also retained endonuclease activity in its PIN domain. In vivo localization studies and analyzes of substrate specificities revealed that hDIS3L is restricted to cytoplasmic exosome, whereas hDIS3 is mainly a nucleoplasmic protein with a small fraction present in the cytoplasm (Tomecki et al. 2010b, Staals et al. 2010). Additionally, human RRP6 is mainly nuclear and significantly enriched in the nucleoli, with a minor fraction in the cytoplasm. Thus, human RNA exosomes, although basing on the same structural scaffold as their *S. cerevisiae* counterparts, exist as functionally and compositionally distinct variants in different areas of the nucleus and in the cytoplasm (Lykke-Andersen et al. 2011).

Disclosure Of The Invention

Because of the unsatisfactory performance, the occurrence of severe side effects and the fact that resistance to currently used therapeutic agents is quickly developing in cancer (tumor) cells like myeloma cells, new, dedicated therapeutics that specifically affect cancer cells are greatly needed.

The information presented above suggests the existence of a molecular link between functions of the exosome complex and development of different cancers.

The present invention is based on the unexpected finding that inhibition of endonucleolytic DIS3 PIN domain activity in the DIS3 bearing mutation corresponding to mutation found in cancer patients in DIS3 RNB domain gives the effect of synthetic lethality in the cells having such mutation.

As described above, changes in hDIS3 activity, often due to mutations in hDIS3 gene, are frequently found in cancer patients, such as melanoma, colorectal cancer, medulloblastoma, acute myeloid leukaemia, and, in particular, multiple myeloma (MM) patients. Because of the importance of RNA metabolism for cell homeostasis, cancer cells harboring such mutations may be potentially more vulnerable to further impairments to the exosome complex activity. However, in the art there are no successful therapy methods or effective therapeutic agents capable of exploiting this. There are also no methods for selecting, screening and efficient testing of potential new therapeutic agents for such treatment, especially there is no method available for effective selecting and screening for new therapeutic agents, and there is no therapeutic agent which can be used in the treatment of cancers based on synthetic lethality between the mutations present in the RNB domain and the inhibition of endonucleolytic activity of the hDIS3 PIN domain.

Thus, the aim of the invention is to provide for a methods of selection and screening of hDIS3 PIN domain inhibitors, yeast strains and cell lines used in such methods. The aim of the invention is to provide new therapeutic agents—selected hDIS3 PIN domain inhibitors and uses thereof in the treatment of cancers, especially multiple myeloma, bearing mutations in hDIS3 RNB domain, based on synthetic lethality between the mutations present in the RNB domain and the inhibition of endonucleolytic activity of the hDIS3 PIN domain.

The invention relates to a method for selection for the DIS3 PIN domain endonuclease activity inhibitor for use in therapy of cancer cells having the mutation in hDIS3 RNB domain, wherein the method comprises the following steps:

a) construction of a model system comprising DIS3, its fragments, homologues or variants with a mutation in RNB domain, preferably by introducing the mutation occurring in hDIS3 in cancer cells, b) contacting the model system obtained in a) with a tested agent, a putative DIS3 PIN domain endonuclease activity inhibitor, c) evaluation of the activity of the PIN domain in the presence and absence of the tested agent, by the way appropriate to the model system, d) selection of the tested agent for which PIN domain activity is changed as contacted with the tested agent and by this obtaining the DIS3 PIN domain endonuclease activity inhibitor.

The invention also relates to the method for selection for the DIS3 PIN domain endonuclease activity inhibitor for the use in therapy of cancer cells having the mutation in hDIS3 RNB domain, wherein the method comprises:

a) obtaining a purified protein comprising the DIS3 PIN domain, its fragment, variant or homologue, preferably the isolated hDIS3 PIN domain;

b) contacting the protein obtained in a) with a tested agent, a putative DIS3 PIN domain endonuclease activity inhibitor, c) evaluation of the activity of the PIN domain in the presence and absence of the tested agent, preferably by in vitro digestion of RNA substrates, d) selection of the tested agent for which PIN domain activity is changed as contacted with the tested agent and by this, obtaining the DIS3 PIN domain endonuclease activity inhibitor.

The method involving the use of purified hDIS3 variants with mutations in hDIS3 RNB domain is a suitable model system for selection and screening for hDIS3 PIN domain inhibitors in vitro.

The invention also relates to the method of selection for a DIS3 PIN domain endonuclease activity inhibitor for the use in therapy of cancer cell having the mutation in hDIS3 RNB domain, wherein the method comprises:

a) construction of a yeast strain comprising Dis3 with the mutation in RNB domain, preferably by introducing the mutation equivalent to the mutation occurring in hDIS3 in cancer cells, b) contacting the yeast strain obtained in a) with a tested agent, a putative DIS3 PIN domain endonuclease activity inhibitor, c) evaluation of the activity of the PIN domain in the presence and absence of the tested agent, d) selection of the tested agent as the DIS3 PIN domain endonuclease activity inhibitor which after treatment of the yeast constructed in a), but not the yeast with wild type Dis3, leads to selective growth retardation or cell death (synthetic lethality).

Method involving the use of yeast strains with mutations in Dis3 RNB domains is a suitable model system for selection and screening for DIS3 PIN domain inhibitors in vivo.

The invention also relates to the method for selection for a hDIS3 PIN domain endonuclease activity inhibitor for the use in therapy of cancer cells having a mutation in hDIS3 RNB domain, wherein the method comprises:

a) construction of an engineered cell line, preferably a human cell line, comprising hDIS3 with a mutation in RNB domain, its fragment or variant, preferably by introducing a mutation occurring in hDIS3 in cancer cells, b) contacting the cell line obtained in a) with a tested agent, a putative hDIS3 PIN domain endonuclease activity inhibitor, c) evaluation of the activity of the PIN domain in the presence and absence of the tested agent, d) selection of the tested agent as a hDIS3 PIN domain endonuclease activity inhibitor, which after treatment of the cell line constructed in a) but not the cell line expressing wild type hDIS3, leads to selective growth retardation or cell death (synthetic lethality).

The method involving the use of engineered human cell lines with mutations in hDIS3 RNB domain is a suitable model system for selection and screening for hDIS3 PIN domain inhibitors in vivo.

In the preferred method for selection for a DIS3 PIN domain endonuclease activity inhibitor according to invention, the mutation in hDIS3 gene in cancer cells is at least one mutation occurring in multiple myeloma, medulloblastoma, acute myeloid leukaemia.

In the preferred method for selection for a DIS3 PIN domain endonuclease activity inhibitor according to invention, the mutation in hDIS3 RNB domain in cancer cells is at least one mutation selected from S477R, G766R, R780K, V504G, A524P, I845V, D487N with relation to SEQ ID NO: 1.

In the preferred method for selection for a DIS3 PIN domain endonuclease activity inhibitor according to invention the hDIS3 has at least one mutation in the coding sequence within its RNB domain of AA 427-843 of SEQ ID NO: 1, preferably contains at least one amino acid change within its RNB domain of AA 427-843 of SEQ ID NO: 1.

In the preferred method for selection for a hDIS3 PIN domain endonuclease activity inhibitor the DIS3 PIN domain is hDIS3 PIN of AA 1-217 of SEQ ID NO: 1.

The invention also relates to therapeutic agent for use in the treatment of cancer cell having a mutation in hDIS3 RNB domain, wherein the therapeutic agent is obtained with the method of selction for a DIS3 PIN domain endonuclease activity inhibitor according to invention.

The invention also relates to therapeutic agent 2-hydroxy-(4H)-isoquinoline-1,3-dione (also known as ACILAHYL), its derivatives, resolved enantiomers, diastereoisomers, solvates and pharmaceutically acceptable salts thereof for use in treatment of cancer cell having a mutation in hDIS3 RNB domain.

The preferred therapeutic agent is used for cancer cell having a mutation in hDIS3 RNB domain in the cancer cell with at least one mutation selected from S477R, G766R, R780K, V504G, A524P, I845V, D487N with relation to SEQ ID NO: 1.

The preferred therapeutic agent is used for cancer cell in which the hDIS3 RNB domain is hDIS3 RNB domain with at least one mutation in the sequence AA 427-843 of SEQ ID NO: 1.

If the therapeutic agent is a chemical compound the invention also includes solvates, pharmaceutically acceptable prodrugs, pharmaceutically active metabolites, and pharmaceutically acceptable salts of such compounds. With respect to the therapeutic agent 2-hydroxy-(4H)-isoquinoline-1,3-dione the invention also includes derivatives, resolved enantiomers, diastereoisomers, solvates and pharmaceutically acceptable salts thereof having inhibitor activity for DIS3 PIN domain endonuclease activity.

The invention also relates to the use of the therapeutic agent of the invention or the one obtained by the method for selection for a DIS3 PIN domain endonuclease activity inhibitor, for preparation of a medicament for treating cancer cells having a mutation in hDIS3 RNB domain.

The invention also relates to the use of 2-hydroxy-(4H)-isoquinoline-1,3-dione, its derivatives, resolved enantiomers, diastereoisomers, solvates and pharmaceutically acceptable salts thereof for preparation of a medicament for treating cancer cells having a mutation in hDIS3 RNB domain.

The therapeutic agent is preferably used for cancer cell having the mutation in hDIS3 RNB domain with at least one mutation selected from S477R, G766R, R780K, V504G, A524P, I845V, D487N with relation to SEQ ID NO: 1.

Preferably the cancer cell having a mutation in hDIS3 RNB is selected from multiple myeloma, medulloblastoma, acute myeloid leukaemia.

In the preferred use of the therapeutic agent, hDIS3 has at least one mutation in the coding sequence within its RNB domain of AA 427-843 of SEQ ID NO: 1, preferably contains at least one amino acid change within its RNB domain of AA 427-843 of SEQ ID NO: 1.

The invention also relates to the composition comprising a therapeutic agent for use in the treatment of cancer cells having a mutation in hDIS3 RNB domain, wherein the therapeutic agent is obtained with the method for selection for a DIS3 PIN domain endonuclease activity inhibitor of the invention or is therapeutic agent of the invention.

In the preferred embodiment the composition is used for the cancer cell having a mutation in hDIS3 RNB domain in the cancer cell with at least one mutation selected from S477R, G766R, R780K, V504G, A524P, I845V, D487N with relation to SEQ ID NO: 1.

In the preferred use of composition the cancer cell having a mutation in hDIS3 RNB is selected from multiple myeloma, medulloblastoma, acute myeloid leukaemia.

The composition preferably further comprises at least one additional agent having anti-cancer activity, wherein the additional agent has anti-cancer activity against multiple myeloma, medulloblastoma or acute myeloid leukaemia.

Preferably the additional agent is selected from bortezomib, carfilzomib clafen (cyclophosphamide), cyclophosphamide, cytoxan (cyclophosphamide), doxil (doxorubicin hydrochloride liposome), doxorubicin hydrochloride liposome, dox-SL (doxorubicin hydrochloride liposome), evacet (doxorubicin hydrochloride liposome), kyprolis (carfilzomib), lenalidomide, LipoDox (doxorubicin hydrochloride liposome), mozobil (plerixafor), neosar (cyclophosphamide), plerixafor, pomalidomide (pomalyst), pomalyst, revlimid (lenalidomide), synovir (thalidomide), thalidomide, thalomid (thalidomide), velcade (bortezomib), zoledronic acid, zometa (zoledronic acid) for myeloma;

adriamycin PFS (doxorubicin hydrochloride), adriamycin RDF (doxorubicin hydrochloride), arsenic trioxide, cerubidine (daunorubicin hydrochloride), clafen (cyclophosphamide), cyclophosphamide, cytarabine, cytosar-U (cytarabine), cytoxan (cyclophosphamide), daunorubicin hydrochloride, doxorubicin hydrochloride, neosar (cyclophosphamide), rubidomycin (daunorubicin hydrochloride), tarabine PFS (cytarabine), trisenox (arsenic trioxide), vincasar PFS (vincristine sulfate), vincristine sulfate for acute myeloid leukemia (AML);

lomustine, cisplatin, carboplatin, vincristine or cyclophosphamide for medulloblastoma.

In the preferred use of composition DIS3 in cancer cell has at least one mutation in the coding sequence within its RNB domain of AA 427-843 of SEQ ID NO: 1, preferably contains at least one amino acid change within its RNB domain of AA 427-843 of SEQ ID NO: 1.

The present invention also relates to therapeutic agent, its preparations or compositions comprising a therapeutic agent of the invention, or composition of the invention in a pharmaceutically acceptable carrier. The choice of a pharmaceutically acceptable carrier will depend on the administration route, as well as on the solubility of the therapeutic agent and the need to protect it from inactivation or degradation prior to entering the cell, tissue or organism. Pharmaceutically acceptable carriers may comprise solvents, dispersants and additives (coatings, surfactants, flavoring agents, antioxidants and others).

The composition of the invention may also comprise at least one additional agent with an anti-cancer activity, preferably an agent with an activity against multiple myeloma, medulloblastoma or acute myeloid leukaemia. The therapeutic agent of the invention and the additional anti-cancer agent(-s) may be co-administered or administered simultaneously or sequentially or in any suitable order.

The composition and the therapeutic agent of the invention may be administered by various routes, including injection, orally or topically. Preparations for oral administration may be in the form of solutions, suspensions, emulsions, capsules, tablets or powders. Oral liquid preparations may contain diluents such as water and alcohols, optionally with the addition of surfactants, suspending agents or emulsifiers. Capsules can be of the gelatin type, and tablets may contain excipients known in the art. Injectable preparations include aqueous and non-aqueous isotonic sterile solutions, optionally containing antioxidants, buffers, isotonic agents and the like. A typical carrier is water or physiological saline.

A composition is generally obtained by diluting and mixing the active ingredient with the carrier or closing it in a carrier. If the therapeutic agent is a nucleic acid, it can be administered in a special liposomal systems that recognize the type of cells or tissues. In another embodiment, the nucleic acid can be introduced by using an expression vector containing a sequence encoding the desired inhibitor, for example, micro RNA or siRNA.

The dose of the therapeutic agent is determined taking into account the route of administration, the progression of the disease, and other significant circumstances like age and weight of the patient.

The invention also relates to the method for inducing synthetic lethality in a cancer cell, wherein the cancer cell having a mutation in hDIS3 RNB domain is treated with an agent inhibiting the endonucleolytic activity of hDIS3 PIN domain.

In the preferred method for inducing synthetic lethality in cancer cells, the agent inhibiting the activity of hDIS3 PIN domain is obtained by the method for selection for a DIS3 PIN domain endonuclease activity inhibitor or is the therapeutic agent of the invention or is the composition of the invention.

In the preferred method for inducing synthetic lethality in cancer cells DIS3 has at least one mutation in the coding sequence within its RNB domain of AA 427-843 of SEQ ID NO: 1, preferably contains at least one amino acid change within its RNB domain of AA 427-843 of SEQ ID NO: 1.

In the preferred method for inducing synthetic lethality in cancer cells the DIS3 PIN domain is hDIS3 PIN of AA 1-217 of SEQ ID NO: 1.

The invention also relates to the yeast strain, preferably a *S. cerevisiae* strain, for use in the method of selection for a DIS3 PIN domain endonuclease activity inhibitor, wherein the yeast strain comprises DIS3 with a mutation in Dis3 RNB domain, which is an equivalent of a mutation found in cancer cell, preferably mutation found in medulloblastoma, acute myeloid leukaemia or multiple myeloma cell.

In the yeast strain mutation in Dis3 RNB domain preferably at least one mutation selected from human equivalents S477R, G766R, R780K, V504G, A524P, I845V, D487N with relation to SEQ ID NO: 1 is present.

In the yeast strain the Dis3 has preferably at least one mutation in the coding sequence within its RNB domain, preferably contains at least one amino acid change within its RNB domain which is homologous to human hDIS3RNB domain of AA 427-843 of SEQ ID NO: 1 and therefore such mutations are equivalent to mutation in cancer cell selected from medulloblastoma, acute myeloid leukaemia or multiple myeloma.

In the preferred yeast strain the DIS3 PIN domain is hDIS3 PIN of AA 1-217 of SEQ ID NO: 1 or the DIS3 PIN domain is DIS3 PIN of (AA 1-241 of SEQ ID NO: 2). The preferred yeast strain is selected from dis3-G833R, dis3-R847K, dis3-V568G, dis3-A588P, dis3-D551N.

In the preferred method of selection for a DIS3 PIN domain endonuclease activity inhibitor for use in therapy of cancer cells having a mutation in hDIS3 RNB domain, the method comprises the use of the yeast strain of the invention.

The invention also relates to the use of the yeast strain of invention for the screening for a DIS3 PIN domain endonuclease activity inhibitor for its use in the therapy of cancer cell having the mutation in hDIS3 RNB domain.

The invention also relates to the cell line for use in the method of selection for a DIS3 PIN domain endonuclease activity inhibitor, in which the cell line comprises DIS3 with the mutation in DIS3 RNB domain which is an equivalent of the mutation found in cancer cell.

The cell line is preferably used in the method of selection for a DIS3 PIN domain endonuclease activity inhibitor for the cancer cell selected from medulloblastoma, acute myeloid leukaemia, multiple myeloma.

The preferred cell line is a human cell line, preferably a derivative of the HEK293 Flp-In T-Rex cell line.

The preferred human cell line of the invention, is constructed with the use of a vector comprising a bidirectional inducible promoter expressing:
sh-microRNA capable of silencing an endogenous hDIS3 copy and
an exogenous hDIS3 variant having a mutation, corresponding to a mutation found in a cancer cell having a mutation in hDIS3 RNB domain, and containing a recoded fragment in order to make it insusceptible to sh-miRNA activity.

The invention also provides the method for construction of the engineered cell line according to the invention and vector for use in such a method.

In the preferred cell line the mutation in DIS3 RNB domain at least one mutation selected from S477R, G766R, R780K, V504G, A524P, I845V, D487N with relation to SEQ ID NO: 1 is present.

In the preferred cell line DIS3 RNB codes for hDIS3 RNB with at least one mutation in the sequence AA 427-843 of SEQ ID NO: 1.

In the preferred cell line DIS3 PIN domain is hDIS3 PIN of AA 1-217 of SEQ ID NO: 1.

In the preferred method of selection for a DIS3 PIN domain endonuclease activity inhibitor for use in therapy of cancer cells having a mutation in hDIS3 RNB domain the method comprises the use of cell line of invention.

The invention also relates to the use of the cell line of invention for the screening for a DIS3 PIN domain endonuclease activity inhibitor for its use in the therapy of cancer cell having the mutation in hDIS3 RNB domain.

In another aspect, the present invention provides a method of screening of cancer patients, in particular medulloblastoma, acute myeloid leukaemia, multiple myeloma patients, with cancer cell harboring a hDIS3 mutation, for the susceptibility of cancer cell to inhibitors of hDIS3 PIN domain activity, wherein the method is an in vitro assay using purified hDIS3 protein, its fragments or homologues, harboring the said mutation.

In another aspect, the invention provides a method of screening of cancer patients, in particular medulloblastoma, acute myeloid leukaemia, multiple myeloma patients, with cells harboring a hDIS3 mutation, for the susceptibility of cancer cells to inhibitors of hDIS3 PIN domain activity, wherein the method involves the use of yeast strains with corresponding mutations in Dis3 RNB domain. The invention also provides the yeast strains for use in such a method of screening of cancer patients, The yeast strains according to the invention for use in such a method harbor a non-lethal Dis3 RNB domain mutation, corresponding to the mutation found in human patient.

In yet another aspect, the invention provides the method involving the use of engineered human cell lines with mutations in hDIS3 RNB domain for screening of cancer patients, in particular medulloblastoma, acute myeloid leukaemia, multiple myeloma patients, for the susceptibility of cancer cells to inhibitors of hDIS3 PIN domain activity. The invention also provides the engineered human cell lines for use in such a method for screening of cancer patients. The engineered human cell line used in such a method, harbors a non-lethal Dis3 RNB domain mutation, corresponding to the mutation found in patient.

BRIEF DESCRIPTION OF DRAWINGS

FIGS. 1A-C. Substitutions of conserved amino acids in hDIS3 RNB domain decrease enzymatic activity of the protein. (A) Schematic view of domain organization of human and yeast Dis3 proteins. Amino acids substituted in multiple myeloma are indicated in light gray and their positions with respect to Dis3 domains are marked with arrows. An asterisk indicates position of D487, which was previously shown to be critical for exoribonucleolytic activity of hDIS3. Corresponding amino acids in S. cerevisiae Dis3p are marked with italics. (B) SDS-PAGE analysis of different variants of the full-length hDIS3 protein purified using two-step affinity chromatography, followed by gel filtration. Position of hDIS3 proteins is marked with a solid arrow. Common contamination with bacterial DnaK chaperone and hDIS3 proteolytic degradation products are indicated with an asterisk and open arrows, respectively. PageRuler™ Prestained Protein Ladder (Fermentas) with molecular masses indicated was used as a marker in the leftmost lane. (C) TLC analysis of the RNA degradation efficiency for different recombinant variants of the full-length hDIS3 protein, shown in (B). Internally radiolabeled RNA, synthesized by the in vitro transcription in the presence of [$\alpha$-$^{32}$P]UTP, was incubated with equal amounts of various hDIS3 versions or in the absence of the protein. Sample aliquots were collected at indicated time points and spotted onto PEI-cellulose TLC plate, which was then developed in the direction shown with the vertical grey arrow; positions of substrate and product (UMP) are indicated with solid and open arrows, respectively. S477R, G766R and R780K mutations significantly inhibit ribonucleolytic degradation.

FIGS. 3A-D. Mutations in yeast DIS3 in positions analogous to those found in multiple myeloma cause growth defects and molecular phenotypes indicating exosome dysfunction. (A) Serial dilutions of indicated yeast strains were spotted on YPD plates and incubated at 25° C., 30° C. and 37° C. for 60 hours. V568G and A524P mutations resulted in thermosensitivity, while G833R and R847K substitutions led to growth inhibition at all tested temperatures. The two G833R and R847K point mutations seemed to give synergistic effect in rrp6Δ background. (B) Total RNA isolated from the same strains as in (A) was subjected to northern-blot analysis using probes specific to typical exosome substrates; DIS3 mutations (G833R and R847K in particular) caused accumulation of 5'-ETS, NEL025 cryptic unstable transcript and 7S precursor of 5.8S rRNA synthesis (as well as their degradation intermediates). (C) Western-blot analysis of the expression of different protein A-tagged exogenous Dis3 proteins in constructed single-mutant yeast strains. Total protein samples were isolated from various yeast strains, separated in SDS-PAGE gel and transferred onto nitrocellulose membrane, which was then probed with peroxidase-anti-peroxidase antibody. Masses of individual bands of molecular weight protein ladder are indicated on the left. All Dis3 variants were efficiently expressed. (D) Catalytic mutation in Dis3 PIN domain is synthetically lethal with mutations in RNB domain corresponding to those associated with MM. Diploid yeast strains in which one DIS3 allele contained D171N mutation, inactivating Dis3 PIN domain endonuclease activity and either G833R (top) or R847K (bottom) amino acid change, were sporulated and spores were dissected. Only two spores from each tetrad were viable. Numbers 1-4 correspond to individual tetrads.

FIGS. 9A-C. MM-associated hDIS3 mutations adversely affect cell growth and metabolic activity in a human cellular model. (A) Cell-growth assay; equal amounts of each cell line were seeded on culture dishes, subjected to doxycycline-mediated induction (48 hours+48 hours) and analyzed by microscopy; the cells harboring mutated hDIS3 versions grew worse that their counterpart producing wild-type protein and the strength of growth phenotype was the following: hDIS3$^{D487N}$>hDis3$^{R780K}$>hDIS3$^{G766R}$. (B) Cell competition assay. Equal amounts of each stable model cell line and "empty" HEK293 Flp-In T-REx were mixed, subjected to doxycycline-mediated induction and analyzed using an epifluorescent microscope; ratio of fluorescent/non-fluorescent cells reflected survival potential of a given model cell line and proved to be much lower for the cells producing hDIS3$^{D487N}$ and hDIS3$^{R780K}$ variants than for their counterparts synthesizing hDIS3$^{G766R}$ or hDIS3$^{WT}$ versions. (C) Metabolic activity assay; approximately equal number of cells representing each stable cell line were grown in triplicates in 96-well plates (either uninduced: "−dox" or treated with doxycycline: "+dox"); AlamarBlue® reagent was added to the cells after time periods indicated and changes of the metabolic status were reflected by colorimetric measurements; in agreement with results from (A), hDIS3$^{D487N}$ and hDIS3$^{G766R}$ mutants gave strongest and weakest phenotype, respectively.

FIGS. 10A-E. Catalytic mutation in the hDIS3 PIN domain, responsible for endonucleolytic activity, leads to synergistic effects with MM-associated mutations within RNB domain. (A) Cell-growth assay; equal amounts of each cell line were seeded on culture dishes, grown in the absence (−dox) or presence (+dox) of doxycycline and analyzed by microscopy; the cell lines producing hDIS3 variants harboring mutations in both catalytic domains of hDIS3 grew significantly worse than the respective cell lines producing hDIS3 versions with mutated amino acids only within RNB domain. (B) Metabolic activity assay; approximately equal number of cells representing each stable cell line were grown in triplicates in 96-well plates (either uninduced: "−dox" or treated with doxycycline: "+dox"); AlamarBlue® reagent was added to the cells after 72 hours and metabolic status was assessed by colorimetric measurements; in agreement with results from (A), cells producing hDIS3 double mutants display lower metabolic activity than their counterparts expressing protein variants with intact PIN domain. (C) Catalytic mutation of PIN domain does not enhance accumulation of 3'-extended 5.8S rRNA precursor molecules; high-resolution northern-blot analysis of 5.8S rRNA and its precursor: total RNA was isolated from cell lines producing either wild-type hDIS3 or its variants with mutations in the PIN or/and RNB domains, which were all subjected to doxycycline treatment; RNA samples were resolved in denaturing polyacrylamide gel for 2 hours; following RNA transfer, nylon membranes were hybridized with probes complementary either to mature 5.8S rRNA or to the region located downstream its 3' border (precursor probe); 5S rRNA was utilized as a loading control. (D) and (E) Quantitative PCR analysis of different PROMPT regions (D) and corresponding protein-coding transcripts (E) in cell lines producing different hDIS3 variants; the graphs show results of quantification of three independent experiments; values on the left represent fold increase of transcripts in cells expressing mutated versus wild-type hDIS3; GAPDH mRNA was utilized for normalization purposes; abundance of all analyzed PROMPTs was highly increased in cells producing hDIS3 double mutants when compared to the respective proteins harboring mutations only within RNB domain (D); the same trend was also observable for mRNAs synthesized under the control of respective promoters located downstream for the three of the analyzed PROMPT regions, but not for unrelated mitochondrial transcript—ATP6/8, which was used as a negative control (E);

DESCRIPTION OF EMBODIMENTS

Figure 2A:
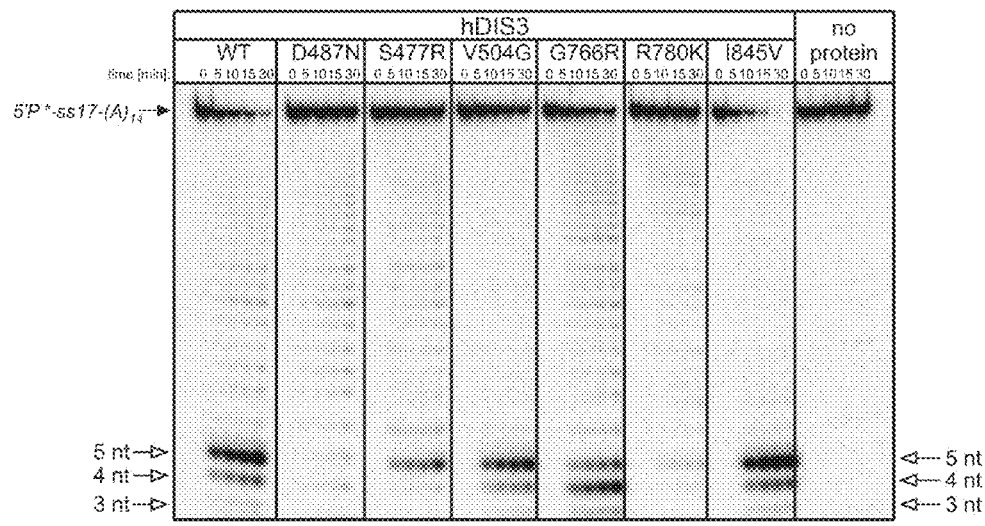
FIGS. 2A-C. hDIS3 mutations result in changes of the degradation pattern of unstructured RNA substrates and inability to degrade structured substrates. (A) 5'-labeled ss17-(A)$_{14}$ substrate was incubated in a buffer containing 100 μM magnesium with equal amounts of different versions of hDIS3 or in the absence of the protein. Reactions were terminated at the indicated time points, followed by denaturing PAGE and phosphorimaging. Positions of substrate and 3-5-nt-long degradation products are marked with solid and open arrows, respectively. R780K mutation abolished the activity, similarly to D487N, while S477R and G766R substitutions led to the change in ratio of 5nt/4nt products. (B) Experiment was performed as in (A), but using 5'-labeled ss44 oligonucleotide. S477R and R780K mutations markedly reduced hDIS3 exoribonucleolytic activity. G766R amino acid change resulted in the loss of processivity. (C) Experiment was performed as in (A), but using 5'-labeled RNA substrate forming a partial duplex ds17-(A)$_{14}$. hDIS3$^{S477R}$, hDIS3$^{G766R}$ and hDIS3$^{R780K}$ mutated proteins were not able to continue degradation of the substrate upon encountering double-stranded region.

As discussed herein, the invention relates to the novel methods of selection of exosome complex inhibitors which are hDIS3 PIN domain inhibitors, which can be further use as therapeutic agent for the treatment of cancers bearing mutations in the RNB domain of the hDIS3 ribonuclease. Preferably RNB domain of the hDIS3 is (427-843 of SEQ ID NO: 1), and hDIS3 PIN domain is (1-217 of SEQ ID NO: 1). The mutations in the RNB domain of the hDIS3 ribonuclease are preferably the same as the mutations occurring in cancers like medulloblastoma, acute myeloid leukaemia, and, in particular, multiple myeloma. The mutations in the RNB domain of the hDIS3 ribonuclease are preferably selected from mutations S477R, G766R, R780K, V504G, A524P, I845V with relation to SEQ ID NO: 1. The invention also relates to the novel hDIS3 PIN domain inhibitor which is selected by the method of invention and its use as therapeutic agent for the treatment of cancers bearing mutations in the RNB domain of the hDIS3 ribonuclease, such as medulloblastoma, acute myeloid leukaemia, and, in particular, multiple myeloma. The mutations in the RNB domain of the hDIS3 ribonuclease are preferably the same as the mutations occurring in cancers like multiple myeloma, medulloblastoma, acute myeloid leukaemia The mutations in the RNB domain of the hDIS3 ribonuclease are preferably selected from mutation S477R, G766R, R780K, V504G, A524P, I845V with relation to SEQ ID NO: 1. The use of exosome complex inhibitor which is hDIS3 PIN domain inhibitor as the therapeutic agent is based on synthetic lethality between the mutations already present in the RNB domain and externally-induced inhibition of endonucleolytic activity of the hDIS3 PIN domain by the novel exosome complex inhibitor which is hDIS3 PIN domain inhibitor.

As used herein, the terms "protein", "peptide", "protein fragment" are used interchangeably to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

A "protein domain" as used herein, is a conserved part of a given protein sequence and structure that can evolve, function, and exist independently of the rest of the protein chain. Each domain forms a compact three-dimensional structure and often can be independently stable and folded. The "DIS3 RNB domain" as used herein, is a part of the DIS3 ribonuclease, preferably yeast (for example *Saccharomyces cerevisiae*) or human, with an exoribonucleolytic activity. The hDIS3 RNB domain comprises amino acids 427-843 in the hDIS3 protein sequence (AA 427-843 of SEQ ID NO: 1). The *S. cerevisiae* Dis3 RNB domain comprises amino acids 478-910 in the yeast Dis3 protein sequence (AA 478-910 of SEQ ID NO: 2).

The "DIS3 PIN domain" as used herein, is a part of the DIS3 ribonuclease, preferably yeast (for example *Saccharomyces cerevisiae*) or human, with an endoribonucleolytic activity. The DIS3 PIN domain in human cells comprises amino acids 1-217 in the DIS3 protein sequence(AA 1-127 of SEQ ID NO: 1). The *S. cerevisiae* Dis3 PIN domain comprises amino acids 1-241 in the yeast Dis3 protein sequence (AA 1-241 of SEQ ID NO: 2).

An "isolated" polynucleotide or polypeptide is one that is substantially free of the materials with which it is associated in its native environment.

The term "homology" or "identity", with respect to a nucleotide or amino acid sequence, indicates a quantitative measure of homology between two sequences. Homologues have at least a 50% identity compared to a reference sequence. Preferably a homologue has 80, 85, 90, 95, 98 or 99% identity to a sequence of reference. A "homologous nucleic acid sequence" or "homologous amino acid sequence," or variations thereof, refer to sequences characterized by a homology at the nucleotide level or amino acid level as defined above. Sequence similarity for polypeptides, which is also referred to as sequence identity, is typically measured using sequence analysis software. In the present invention, homologous protein sequences include protein sequences of a polypeptide of species other than humans, including, but not limited to, yeast (*Saccharomyces cerevisiae*).

As used herein, the terminology "equivalent mutation" refers to mutations in substantially equivalent sequences, for example homologues as defined above, that are in locations different from, but corresponding to one another.

"Synthetic lethality" used herein is intended to refer to a type of interaction where the co-occurrence of a genetic event and the activity of an agent (like therapeutic agent, DIS3 PIN domain endonuclease activity inhibitor or drug) results in organismal or cellular death or selective growth retardation, in particular cancer cell death.

A "vector" refers to a recombinant DNA or RNA plasmid or virus that comprises a heterologous polynucleotide to be delivered to a target cell, either in vitro or in vivo.

The term "recombinant" means a polynucleotide semisynthetic, or synthetic origin which either does not occur in nature or is linked to another polynucleotide in an arrangement not found in nature.

The terms "cancer" and "cancerous" refer to or describe the physiological condition in mammals that is typically characterized by unregulated cell growth. A "tumor" comprises one or more cancerous cells. Examples of cancers include, but are not limited to, multiple myeloma, medulloblastoma, acute myeloid leukaemia. Thus by the term cancer as use herein both cancer and tumor should be understood.

The phrase "pharmaceutically acceptable" indicates that the substance or composition must be compatible chemically and/or toxicologically, with the other ingredients comprising a formulation, and/or the mammal being treated therewith.

As used herein, the terms "treat" and "treatment" refer to both therapeutic treatment and prophylactic or preventative measures, wherein the object is to prevent or slow down (lessen) an-undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented. In the case of cancer, the treatment should be understood as reducing the number of cancer cells; reducing the cancer (tumor) size; inhibiting (i.e., slowing to some extent and preferably stopping) cancer cell or tumor growth; and/or relieving to some extent one or more of the symptoms associated with the cancer.

The term "derivative" for chemical compound shall be understood as compound that is derived from a similar compound by some chemical or physical process.

The majority of mutations found in MM and other cancers affect conserved residues in the hDIS3 RNB domain which points to the fact that they may have an impact on the exonucleolytic activity of this enzyme (FIG. IA). On the contrary, none of these mutations locate within PIN domain, entirely responsible for the second, endoribonucleolytic activity of hDIS3 (FIG. 1A).

The applicants have found that several mutations in the hDIS3 gene, observed in MM patients, like the hDIS3$^{S477R}$, hDIS3$^{G766R}$ and hDIS3$^{R780K}$ variants, significantly diminish exoribonucleolytic activity of hDIS3 protein (FIG. 1C, FIG. 2). Biochemical assays performed using recombinant variants of hDIS3, bearing the S477R, G766R and R780K mutations and 5'-end labeled RNA substrates (such as used in Example 1, below) show that not only the overall activity is reduced, but also disclose that mutations found in MM patients lead to changes in the pattern of final degradation products, enzyme processivity and ability to degrade structured regions of RNA molecules.

In support of this, the applicants further demonstrate that yeast strains expressing endogenous Dis3 with introduced amino acid changes equivalent to those found in MM patients (such as: dis3-G833R (G766R in humans), dis3-R847K (R780K in humans), dis3-V568G (V504G in humans) and dis3-A588P (A524P in humans)), display growth defects of various strength. This is accompanied by molecular phenotypes typical for exosome dysfunction (FIG. 3A, 3B). Moreover, it is unexpectedly shown that a further inactivation of N-terminal PIN domain endonuclease activity in yeast is synthetically lethal with MM-like Dis3 mutations in RNB domain, which adversely affect exoribonucleolytic activity of the protein (FIG. 3D). Since there are differences between human and yeast exosomes, despite the well conserved structure, a human model was also constructed by the applicants. It was unexpectedly shown that human cells harboring the hDIS3 mutations observed in MM patients grow at a slower rate and display lower metabolic activity than their counterpart expressing wild-type hDIS3 version (FIG. 9). Growth defects correlate well with accumulation of RNA molecules synthesized by all 3 human RNA polymerases. The strongest accumulation is observed in the case of 5.8S ribosomal RNA precursor and unstable noncoding transcripts—PROMPTs (FIG. 6).

It turned out that the inactivation of hDIS3 PIN domain endonucleolytic activity acts synergistically with MM-associated mutations within RNB domain, causing enhanced growth aberrations and additional accumulation of PROMPTs (FIG. 10). This finding, together with similar results obtained in the case of yeast, unexpectedly demonstrates that the PIN domain is a very effective target for design of novel therapeutic agents that might be employed in therapy of cancers with changed hDIS3 activity, preferably harboring mutations in the RNB domain of the hDIS3 ribonuclease, such as changes occurring in the RNB domain of the hDIS3 in medulloblastoma, acute myeloid leukaemia, and, in particular, multiple myeloma (MM).

Further, it was shown by the applicants that 2-hydroxy-(4H)-isoquinoline-1,3-dione (AC1LAHYL) acts as an inhibitor of the hDIS3 PIN domain activity and is capable of specifically inhibiting the growth of cells with DIS3 MM-associated mutations.

Therefore, an exosome complex inhibitor, preferably a hDIS3 PIN domain inhibitor, in particular 2-hydroxy-(4H)-isoquinoline-1,3-dione (AC1LAHYL), its derivatives, resolved enantiomers, diastereoisomers, solvates and pharmaceutically acceptable salts thereof may be used to specifically target cancer cells, such as medulloblastoma, acute myeloid leukaemia and, in particular, multiple myeloma cells, bearing the hDIS3 mutations. The mutations in the RNB domain of the hDIS3 in these cancers are preferably selected from mutation S477R, G766R, R780K, V504G, A524P, I845V with relation to SEQ ID NO: 1.

The in vitro assay, based on the in vitro digestion of RNA substrates, described herein, may also be used for screening for novel hDIS3 PIN domain endonuclease activity inhibitors, with the use of purified hDIS3 protein, its fragments (such as a recombinant version of the isolated PIN domain) or homologs. The purified hDIS3 protein or its isolated PIN domain may be obtained and purified from bacteria, preferably E. coli, following heterologous expression. Preferably, the isolated hDIS3 PIN domain comprises the sequence disclosed in 1-217 of SEQ ID NO: 1. The RNA substrate may be for example 5' fluoresceine-labeled ss17-(A)$_{34}$. The evaluation of the activity of the PIN domain in the presence and absence of the tested agent may be evaluated by any means readily known to the ones skilled in the art, such as denaturing PAGE and fluorimaging. Therapeutic agents found with the use of this method may preferably be used in cancer therapy of cancers bearing hDIS3 mutations, preferably mutations in the RNB domain of the hDIS3 such as multiple myeloma, medulloblastoma, acute myeloid leukaemia.

As described herein, the yeast strains expressing endogenous Dis3 with introduced amino acid changes equivalent to those found in MM patients, such as dis3-G833R (G766R in humans), dis3-R847K (R780K in humans), dis3-V568G (V504G in humans), dis3-A588P (A524P in humans), may also be applied for screening for novel therapeutic agents which are hDIS3 PIN domain inhibitors. Such agents may be detected by their capability to inhibit the growth of said yeast strains when added to the yeast growth medium. The exosome function may also be evaluated for such yeast strains and compared for yeast grown in the presence and absence of the tested agent. The evaluation of exosome function may be performed by any means known to the ones skilled in the art, for example by isolation of total RNA, further northern-blot analysis using probes specific to typical exosome substrates; such as 5'-ETS, NEL025 cryptic unstable transcript and 7S precursor of 5.8S rRNA synthesis (as well as their degradation intermediates). Therapeutic agents found with this method may preferably be used in cancer therapy of cancers bearing hDIS3 mutations, preferably mutations in the RNB domain of the hDIS3 such as multiple myeloma, medulloblastoma, acute myeloid leukaemia.

The engineered human cell line assay, described herein, may also be used for screening for novel PIN domain endonuclease activity inhibitors. The human model stable cell lines producing hDIS3 variants for example with MM-like mutations may be obtained with the use of a vector for transfection, said vector comprising a bidirectional inducible promoter expressing for example:
  sh-microRNA capable of silencing an endogenous hDIS3 copy and
  an exogenous hDIS3 variant harboring a mutation, corresponding to a mutation found in a cancer patient, and containing a recoded fragment in order to make it insusceptible to sh-miRNA activity.

The vector may additionally comprise a marker gene, such as eGFP. The vector of the invention may comprise the nucleotide sequence of pMM9 or pMM10.

This type of vector allows for the construction of a human cell line expressing a desired hDIS3 variant. Such an engineered human cell line of the invention may be used for the evaluation of exosome function by any means known to the ones skilled in the art. Such methods may include, for example: assessing cellular growth of the cells after induction of expression of miRNA silencing the endogenous copy of hDIS3 and induction of expression of the exogenous hDIS3 variant. This may be accomplished by microscopy (preferably fluorescence microscopy) and/or flow cytometry. It may also be coupled with cell viability assessment (preferably an assay sensitive to cell metabolic activity, for example AlamarBlue®. The evaluation of exosome function may include examining exosome substrates, such as 5.8S rRNA processing intermediates, tRNAs, RNA polymerase III transcripts and PROMPTs. This may be achieved, for example, by total RNA isolation after induction of expression of sh-miRNA silencing of the endogenous hDIS3 copy and simultaneous induction of expression of the exogenous hDIS3 variant. This may be followed by low- or high-resolution northern blots. Isolated RNA may also be reverse transcribed to DNA and further analyzed with methods such as PCR or RealTime PCR.

The in vitro assay disclosed herein, based on RNA substrates and purified hDIS3 protein bearing the mutation found in specific cancer patients, may also be used for evaluating the effects on exosome functions of new hDIS3 mutations found in the cancer patients and further to assess the potential susceptibility of the cancer cells with the specific mutation to future therapy using an exosome complex inhibitor, preferably a hDIS3 PIN domain inhibitor. The purified hDIS3 protein bearing the mutation found in specific cancer patients may be prepared as a recombinant variant of wild type hDIS3 sequence and purified from a bacteria, preferably E. coli, following heterologous expression. The RNA substrates may be for example an in vitro transcribed RNA substrate uniformly labeled with UTP, or as another example, 5'-end labeled RNA substrates (such as used in Example 1, below).

The evaluation of the activity of the hDIS3 protein bearing the mutation found in specific cancer patients in presence and absence of the tested agent may be evaluated by any means readily known to the ones skilled in the art, such as: TLC, or denaturing PAGE and phosphorimaging, depending on labeling of RNA substrates.

The yeast methods described herein, based on yeast strains expressing endogenous Dis3 with introduced amino acid changes equivalent specifically to those found in cancer patients, may also be used for evaluating the effects on exosome functions of new hDIS3 mutations found in the cancer patients and further to assess the potential susceptibility of the cancer cells with the specific mutation to future therapy using an exosome complex inhibitor, preferably a hDIS3 PIN domain inhibitor. The evaluation of exosome function in such mutant yeast strains may be performed by any means known to the ones skilled in the art, for example by isolation of total RNA, further northern-blot analysis using probes specific to typical exosome substrates; such as 5'-ETS, NEL025 cryptic unstable transcript and 7S precursor of 5.8S rRNA synthesis (as well as their degradation intermediates).

The vector of the invention may also be used to obtain an engineered human cell line for a specific mutation found in patient's cancer cells in order to evaluate the exoribonucleolytic activity of hDIS3 protein for the specific variant and further to assess the potential susceptibility of the cancer cells with the specific mutation, to therapy using an exosome complex inhibitor, preferably a hDIS3 PIN domain inhibitor. Such an engineered human cell line may be used for evaluation of exosome function by any means known to the ones skilled in the art. Such methods may include, for example: assessing cellular growth of the cells after induction of expression of miRNA silencing the endogenous copy of hDIS3 and induction of expression of the exogenous hDIS3 variant. This may be accomplished by microscopy (preferably fluorescence microscopy) and/or flow cytometry. It may also be coupled with cell viability assessment (preferably an assay sensitive to cell metabolic activity, for example AlamarBlue®. The evaluation of exosome function may include examining exosome substrates, such as 5.8S rRNA processing intermediates, tRNAs, RNA polymerase III transcripts and PROMPTs. This may be achieved for example by total RNA isolation after induction of expression of sh-miRNA silencing of the endogenous hDIS3 copy and simultaneous induction of expression of the exogenous hDIS3 variant. This may be followed by low- or high-resolution northern blots. Isolated RNA may also be reverse transcribed to DNA and further analyzed with methods such as PCR or RealTime PCR.

Although the present invention and its advantages have been described in detail, it should be understood that various changes, substitutions and alterations can be made herein without departing from the spirit and scope of the invention as defined in the appended claims.

The present invention will be further illustrated in the following examples which are given for illustration purposes only and are not intended to limit the invention in any way.

EXAMPLES

In the following examples, unless specified otherwise, standard materials and methods are used as described in Sambrook J. et al. "Molecular Cloning: A Laboratory Manual, $2^{nd}$ edition, 1989, Cold Spring Harbor, N.Y. Cold Spring Harbor Laboratory Press, or proceeding in accordance with manufacturers' recommendations for specific materials and methods.

Bacterial Strains

The following E. coli strains were used: MH1 (E. coli araD lacX74 galU hsdR hsdM rpsL), dam-/dcm-(New England Biolabs; *E. coli* ara-14 leuB6fhuA31 lacY1 tsx78 glnV44 galK2 galT22 mcrA dcm-6 hisG4 rfbD1 R(zgb210::Tn10) Tet$^S$ endA1 rspL136 (Str$^R$) dam13::Tn9 (Cam$^R$) xylA-5 mtl-1 thi-1 mcrB1 hsdR2), BL21-CodonPlus-RIL (Stratagene; *E. coli* B F− ompT hsdS($r_B^-$ $m_B^-$) dcm+ Tet$^r$ gal endA Hte [argU ileY leuW Cam$^r$]).

Yeast Strains

*S. cerevisiae* strain encoding fusion of wild-type Dis3p with and protein A tag-TEV protease cleavage site and TRP selection marker (ADZY532; referred herein to as wt) was a derivative of haploid BMA64 (MATa ade 2-1 his3-11,15 leu2-3, 112 trp1Δ ura3-1 can1-100), created by homologous recombination (Puig et al. 2001). *S. cerevisiae* strain dis3-D551N mutant was constructed previously (Dziembowski et al. 2007). rrp6Δ strain was from Euroscarf (acc. no.: Y11777; BY4742 MATα his3Δ1 leu2Δ0 lys2Δ0 ura3Δ0 YOR001w::kanMX4). *S. cerevisiae* strains dis3-V568G, dis3-A588P, dis3-G833R and dis3-R847K mutants were constructed as specified in Example II.

*S. cerevisiae* strain ADZY531 was constructed as follows. D171N mutation was introduced into the DIS3 gene in the BMA64 wild type haploid strain by in vivo recombination. First, the fragment of DIS3 gene with the D171N mutation was amplified using ADZKD 106 (CGGTCATATGAGAGTGTGTTGCG) (SEQ ID NO: 3) and ADZKD110 primers (GAGAATTTGTATTTTCAGGGTGAGC) (SEQ ID NO: 4) and pBS3278 vector (Lebreton et al. 2008) as a template. The remaining part of the DIS3 gene, together with protein A tag-protease TEV cleavage site and TRP selection marker was amplified using ADZKD111 (GCTCACCCTGAAAATACAAATTCTC) (SEQ ID NO: 5) and ADZKD107 (AGTGGTTTAGTGGTAAAATCCAACGTTGCCATCGTTGGGCCCCCGGTTCG) (SEQ ID NO: 6) primers and a genomic DNA isolated from ADZY532 strain as a template. In the last step, overlap PCR was performed using ADZKD106 and ADZKD107 primer and both amplicons obtained in reactions described above, in order to join both fragments. Transformation of the haploid BMA64 strain with the final PCR product gave strain ADZY531.

All restriction enzymes and T4 DNA ligase were from Thermo Scientific. CIP was from New England Biolabs. All DNA purification kits: DNA Plasmid Mini, DNA Plasmid Midi and Gel-Out were from A&A Biotechnology. T4 PNK was from New England Biolabs. PCR reactions were performed with the Phusion DNA polymerase (Thermo Scientific).

In the Table 6 there are gathered hDIS3 RNB domain mutations, their equivalents in yeast strains or cell lines and effects observed for such mutants, obtained in the below Examples.

Example I

Proteins Encoded by some hDIS3 Gene Versions with MM-Associated Mutations Display Various Defects in the Degradation of Different RNA Substrates.

Oligonucleotides, Plasmids and Cloning.

The *E. coli* BL21-CodonPlus-RIL strain was used. Plasmids pMM1, pMM2, pMM3, pMM4, pMM5 and pMM6 (for heterologous expression of various hDIS3 versions in *E. coli*) were generated by site-directed mutagenesis with oligonucleotide pairs shown in Table 1, using a pHEX1 construct (encoding wild-type hDIS3; Tomecki et al. 2010b) as template.

TABLE 1

Primers used for site-directed mutagenesis and construction of recombinant hDIS3 variants bearing MM-associated mutations, for heterologous expression in *E. coli*.

| Name | Nucleotide sequence (5'-3') | Seq. Id. No | Constructed plasmid | hDIS3 variant |
|---|---|---|---|---|
| S477Rfor | TGTGTATCTGCAGAGTAGACCCACCAGGATGTACTGATATAG | 7 | pMM1 | S477R |
| S477Rrev | GGTCTACTCTGCAGATACACAGATGCCTCAGGTCTTCTCGG | 8 | | |
| V504Gfor | AGGT TGGTGGCCATATTGCTGATGTGAGCCATTTTATTAGG | 9 | pMM2 | V504G |
| V504Grev | AGCAATATGGCCACCAACCTCCAAATTTCCATTTTCGAGTTC | 10 | | |
| A524Pfor | AGAATCACCTAGGAGAGGAACAACTGTGTATCTTTGTGAAAAG | 11 | pMM3 | A524P |
| A524Prev | TTCCTCTCCTAGGTGATTCTTGATCCAAGGCATTTCCTGGC | 12 | | |
| G766Rfor | CATCACTACCGGTTAGCGTCTCCAATATACACACATTTTAC | 13 | pMM4 | G766R |
| G766Rrev | GACGCTAACCGGTAGTGATGAAAATCATTATCCATTCCAGAAC | 14 | | |
| R780Kfor | CCCATTAAACGTTACGCAGATGTCATTGTTCATCGGCTTTTGG | 15 | pMM5 | R780K |
| R780Krev | TCTGCGTAACGTTTAATGGGTGAAGTAAAATGTGTGTATATTGG | 16 | | |
| I845Vfor | CAAAGGAGTAGTAAGTGAAGAGGCCTATATTTTATTTGTAAGAAAGAATGCC | 17 | pMM6 | I845V |
| I845Vrev | AAAATATAGGCCTCTTCACTTACTACTCCTTTGCTTTTGAAGAATAACTGGG | 18 | | |

The presence of S477R, V504G, A524P, G766R, R780K and I845V mutations was confirmed by digestion with PstI, MlsI, XmaJI, BshTI, Psp1406I and Eco1471 restriction enzymes, respectively and sequencing of hDIS3 inserts using primers (Table 2).

TABLE 2

Primers used for sequencing of hDIS3 inserts.

| Name | Nucleotide sequence (5'-3') | Seq. Id. No |
|---|---|---|
| SumoF | TCATACTGTCAAAGACAGGG | 19 |
| HD3F883 | GAAGATATTGTGGCTGTGGAGC | 20 |
| HD3F1848 | CCGTGGACTGAATAAACTAGCC | 21 |
| HD3F2429 | TGACAGACAAACACAAGCTTGC | 22 |
| HD3R1021 | TTACAGCAGTCTTAAGCATTCG | 23 |

TABLE 2-continued

Primers used for sequencing of hDIS3 inserts.

| Name | Nucleotide sequence (5'-3') | Seq. Id. No |
|---|---|---|
| HD3R1592 | CTGGCTGATTCTTGATCCAAGG | 24 |
| HD3R2443 | TGTGTTTGTCTGTCAACTCTGG | 25 | pHEX8 construct, encoding hDIS3 with D487N mutation—a genuine catalytic mutant of RNB domain (Tomecki et al. 2010b) was also used for comparison.

Heterologous Expression and Purification of hDIS3 Proteins.

For purification of different hDIS3 versions, E. coli BL21-CodonPlus-RIL strain (Stratagene) was transformed with appropriate plasmids (pHEX1, pHEX8, pMM1, pMM2, pMM3, pMM4, pMM5, pMM6). Transformant growth and further protein isolation was performed according to standard procedures. Proteins were purified from native extracts by nickel affinity chromatography and gel filtration on Superdex S-200 10/300 GL column (GE Healthcare). All steps were done automatically using an ÄKTAxpress apparatus. The purity of the proteins was assessed by electrophoresis in SDS-PAGE gels. Protein amounts were estimated by densitometric analysis of the gels stained with Coomassie Brilliant Blue R-250 using serial dilutions of BSA as a standard. The obtained purified hDIS3 variants corresponding to wild type, catalytic mutant and variants found in MM patients were used further in in vitro biochemical assays.

Substrate Preparation for in vitro Biochemical Assays.

Oligoribonucleotides:

ss17-$A_{14}$,
(SEQ ID NO: 26)
r(CCCCACCACCAUCACUUAAAAAAAAAAAAAA), ss44,
(SEQ ID NO: 27)
r(CGACUGGAGCACGAGGACACUGACAUGGACUGAAGGAGUAGAAA)
and comp1,
(SEQ ID NO: 28)
r(AAGUGAUGGUGGUGGGG)

were purified by electrophoresis, excision and elution 5'-end labeling of substrates was performed with T4 PNK (NEB) and [γ-$^{32}$P]ATP (GE Healthcare). All labeled single-stranded RNA substrates were further purified following electrophoresis. ds17-$(A)_{14}$ partial RNA duplex was prepared by mixing nonradioactive single-stranded oligoribonucleotides ss17-$(A)_{14}$ and comp1 in a 1:1.2 molar ratio, with addition of radiolabeled ss17-$(A)_{14}$ oligo in standard conditions. Internally labeled RNA was obtained by in vitro transcription performed using pLsm1 plasmid digested with SalI as a template, in the presence of [α-$^{32}$P]UTP and T7 RNA polymerase (NEB). Radiolabeled transcript was extracted and further purified by centrifugation in Spin Modules (MP Biomedicals) packed with Sephadex G-50 (Bio-Rad).

pLsm1 plasmid, used for preparing internally labeled RNA, kindly provided by Prof. Joanna Kufel (University of Warsaw), is pGEM-T Easy with insert encompassing nucleotides 1-387 of the open reading frame corresponding to A. thaliana Lsm1 protein.

Exoribonuclease Assays.

In vitro enzymatic assays of hDIS3 exoribonucleolytic activity were performed in 10 mM Tris-HCl, pH 8.0; 75 mM NaCl; 1 mM 2-mercaptoethanol, 100 µM $MgCl_2$. Protein concentration was 0.1 µM, while substrate concentration was 0.2 µM or 2 µM for duplex and unstructured RNA molecules, respectively. For gel-based analyses, reactions were performed at 37° C. for the indicated times and then terminated by formamide loading dye Reaction products were resolved in denaturing 20% polyacrylamide, 8 M urea, 1xTBE gels. In the case of TLC-based experiment, samples were collected by mixing aliquots of the reaction mixtures with 1 µl of 0.5 M EDTA and subsequently analysed by running them on PEI-cellulose plates (Schleicher & Schuell) in 0.5 M LiCl/1M formic acid, using non-radioactive UMP as a marker. For both types of analyses, reaction products were visualized using a FUJI PhosphorImager.

In order to analyze the exonucleolytic activity, recombinant versions of hDIS3 protein (either wild-type or bearing different mutations detected in MM) were purified from E. coli following heterologous overexpression. hDIS3$^{S477R}$, hDIS3$^{V504G}$, hDIS3$^{G766R}$, hDIS3$^{R780K}$ and hDIS3$^{I845V}$ mutant proteins were successfully purified (FIG. 1B), while it proved difficult to obtain hDIS3$^{A524P}$ recombinant version, which was insoluble irrespective of expression conditions that were utilized. In parallel, two control hDIS3 variants were purified: hDIS3$^{WT}$, which was previously shown to display robust exoribonucleolytic activity and hDIS3$^{D487N}$—a catalytically inactive mutant with one of the aspartic acid residues coordinating magnesium in the active site of RNB domain substituted with its amide (Tomecki et al. 2010b; see Supplementary FIG. S6 therein, where hDIS3$^{D487N}$ is referred to as hDIS3$^{RNB\ MUT}$). All protein versions mentioned above were obtained with similar efficiency and in all cases it was possible to achieve a comparable degree of purity—the only significant contaminant identified by mass-spectrometry was bacterial DnaK chaperone, which level was slightly increased for hDIS3$^{S477R}$, most probably due to the lower solubility of this particular variant (FIG. 1B).

Then, a preliminary biochemical experiment was performed using all purified hDIS3 variants and in vitro transcribed RNA substrate uniformly labeled with UTP. Time-course-based analysis of degradation of such RNA substrate by a standard TLC method allowed to tentatively assess the influence of individual mutations on exoribonucleolytic activity. It was noted that while the degradative potential of the protein was almost unchanged in the case of hDIS3$^{V504G}$ and hms3$^{I845V}$ (i.e. the rate of RNA decay was comparable to hDIS3$^{WT}$), the activity was severely reduced for hDIS3$^{S477R}$, hDIS3$^{G766R}$ and hDIS3$^{R780K}$ variants (FIG. 1C). For the hDIS3$^{R780K}$, the phenotype closely resembled the one that was observed for the genuine catalytic mutant of RNB domain—hDIS3$^{D487N}$ (FIG. 1C).

Figure 2B:
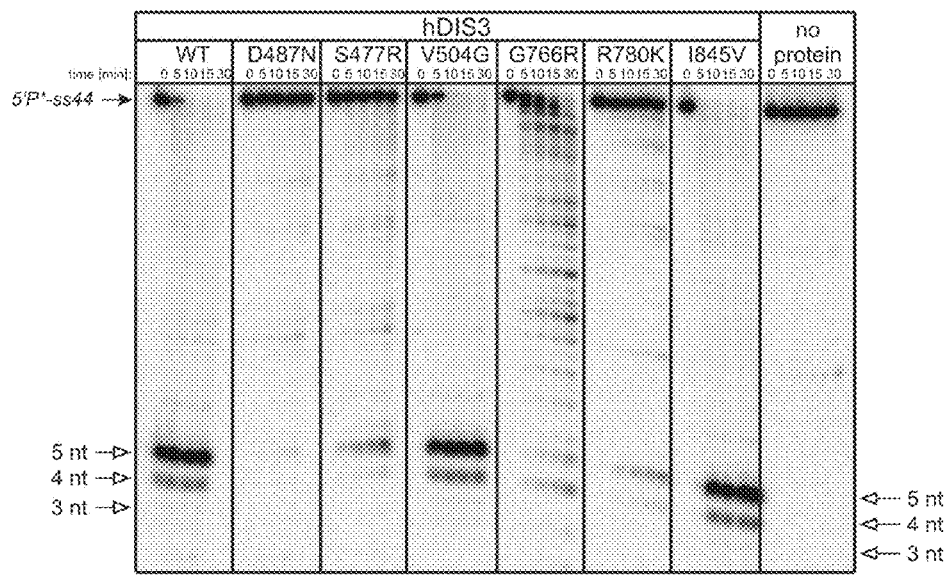
Figure 2C:
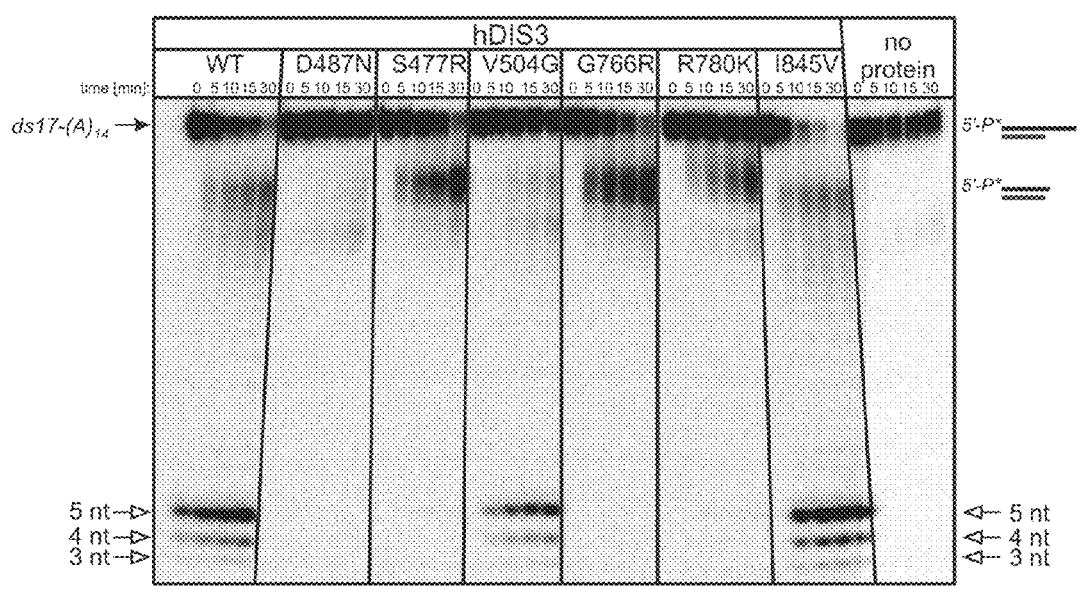

In order to assess defects in RNA degradation caused by different hDIS3 mutations in relation to the wild-type protein in a more qualitative way, biochemical assays were performed on various 5'-end labeled oligoribonucleotide substrates, i.e. 1) single-stranded RNA oligonucleotide, composed of 17-mer generic sequence, followed by 14-nucleotide-long oligo(A) tail (5'P*-ss17-$(A)_{14}$); 2) 44-mer, lacking oligo(A) extension (5'P*-ss44) and 3) structured substrate containing a 17-nucleotide duplex followed by a 14-nt-long oligo(A) tail (5'P*-ds17-$(A)_{14}$), and decay products were analyzed in denaturing polyacrylamide gels (FIG. 2). It was noticed that in case of hDIS3$^{I845V}$ and hDIS3$^{V504G}$ mutants, patterns of final degradation products were exactly the same as for the hDIS3$^{WT}$ control for all substrates (FIG. 2A-C). The rate of degradation was however slightly slower for hDIS3$^{V504G}$ variant when compared to hDIS3$^{WT}$ and hDIS3$^{I845V}$ counterparts. On the contrary, the remaining mutations had visible impact on hDIS3 function. The most striking one was R780K, which led to virtually complete inhibition of exonucleolytic degradation of both single-stranded substrates, similar to catalytic D487N mutation (FIG. 2A, B), which nicely confirmed the results of TLC analysis, shown in the FIG. 1C. On the other hand, hDIS3$^{S477R}$ and hDIS3$^{G766R}$ variants displayed a bit milder defects on 5'P*-ss17-(A)$_{14}$ substrate, consisting in the changes of the ratio of final degradation products in comparison with hDIS3$^{WT}$: for hDIS3$^{S477R}$, the level of 4-nt-long decay products was reduced, while in the case of hDIS3$^{G766R}$ it was increased, at the expense of decrease of the amounts of 5-nt-long degradation products (FIG. 2A). Moreover, hDIS3$^{G766R}$ mutant apparently lost processivity and became distributive in the presence of 5'P*-ss44 substrate (FIG. 2B). Importantly, in the case of partially double-stranded 5'P*-ds17-(A)$_{14}$ substrate, while hDIS3$^{S477R}$, hDIS3$^{G766R}$ and hDIS3$^{R780K}$ seemed to digest a single-stranded extension, they all stalled upon encountering secondary structure in the substrate (this effect was most pronounced for hDIS3 variant harboring R780K mutation), even though the degradation of partial duplex was not completely abolished, as was the case of hDIS3$^{D487N}$ catalytic mutant (FIG. 2C).

Concluding, results of biochemical assays performed employing different techniques and using various RNA substrates strongly indicated that mutations in hDIS3 gene leading to the following amino acid substitutions: S477R, G766R and R780K cause significant aberrations of hDIS3 exoribonucleolytic activity, while in the case of V504G and I845V the effects are more subtle, if any.

Example II

Mutations in Yeast DIS3 Gene Corresponding To those Found in MM Patients Cause Cell-Growth Defects and Molecular Phenotypes Leading To an Impairment of the Exosome Function.

S. Cerevisiae Strains (Yeast Strains) and Construction of Mutants.

dis3-V568G, dis3-A588P, dis3-G833R and dis3-R847K mutants (see FIG. 1A for corresponding human amino acid changes) were constructed as follows. A diploid BMA64 strain was transformed with DNA fragment containing DIS3 gene harboring a respective mutation, a tag (encompassing TEV protease cleavage site and sequence encoding protein A) and the TRP selection marker. First, two parts of the DIS3 gene were produced in two independent amplifications: 5' using ADZKD106 forward primer, complementary to the sequence located upstream the Dis3p coding sequence and suitable reverse primer ADZKD134, ADZKD136, ADZKD138, ADZKD140 covering the mutated site; and 3'—with appropriate forward primer ADZKD133, ADZKD135, ADZKD137, ADZKD139 covering the mutated site and ADZKD107 reverse primer complementary to the sequence downstream the TRP selection marker. Primers, theirs sequences and mutant constructions are specified in the below Table 3.

TABLE 3

| Primer | Seq. Id No | Primer sequence | Primer used for construction |
|---|---|---|---|
| (forward) ADZKD106 | 3 | CGGTCATATGAGAGTGTGTTGCG | |
| (reverse) ADZKD134 | 29 | AGTGAGTAACATCAGCAATATGGCCACCAACTTCCCAATTACCGTT | dis3-V568G |
| (reverse) ADZKD136 | 30 | TATACAGAAGTACCTCTTGCGGGCCCTTCCGCATCCAGGGCAGTGC | dis3-A588P |
| (reverse) ADZKD138 | 31 | TGTGTAGATATCAACGGCTAACCGGTAGTGTCTAAAGTCAGGATA | dis3-G833R |
| (reverse) ADZKD140 | 32 | ATGGGCCACAACATCACAGTAACGTTTAATAGGTGATGTGAAATGTG | dis3-R847K |
| (reverse) ADZKD107 | 6 | AGTGGTTTAGTGGTAAAATCCAACGTTGCCATCGTTGGGCCCCCGGTTCG | |
| (forward) ADZKD133 | 33 | AACGGTAATTGGGAAGTTGGTGGCCATATTGCTGATGTTACTCACT | dis3-V568G |
| (forward) ADZKD135 | 34 | GCACTGCCCTGGATGCGGAAGGGCCCGCAAGAGGTACTTCTGTATA | dis3-A588P |
| (forward) ADZKD137 | 35 | TATCCTGACTTTAGACACTACCGGTTAGCCGTTGATATCTACACA | dis3-G833R |
| (forward) ADZKD139 | 36 | CACATTTCACATCACCTATTAAACGTTACTGTGATGTTGTGGCCCAT | dis3-R847K |

Total genomic DNA isolated from ADZY532 (wt) strain served as template in all above-mentioned amplifications. The full-length amplicons with desired mutations were obtained with ADZKD106 and ADZKD107 primers in overlap PCR (where products of the 5' and 3' amplifications served as templates), and were subsequently used for transformation. Selected transformants were sporulated and spores were dissected. A spore harboring dis3-V568G mutation gave strain ADZY679, dis3-A588P-ADZY681, dis3-G833R-ADZY783 and dis3-R847K-strain ADZY685. The presence of V568G, A588P, G833R and R847K mutations was validated by amplification of the genomic DNA fragments using ADZKD145 (GGATGATGTTAATTGCTTGG) (SEQ ID NO. 37)—ADZKD146 (TTGAAACTCTACCAC-CGACC) (SEQ ID NO. 38) primer pair, followed by digestion of PCR products with MlsI, ApaI, BshTI and Psp1406I restriction enzymes, respectively. Finally, correctness of the ORF sequence was confirmed by sequencing of the obtained PCR product, using primers:

```
                                       (SEQ ID NO. 39)
RTADZ-9:  GAGATACATTGTGAGGGACC,, (SEQ ID NO. 40)
RTADZ-27: ATGTCAGTTCCCGCTATCGC,, (SEQ ID NO. 41)
ADZKD151: CGTCGTTCTTGTTACCAACG,, (SEQ ID NO. 42)
ADZKD152: CACCGTGATTTCCGACAAGC,, (SEQ ID NO. 43)
ADZ1601:  GCCCGCAGAAGGCCACGATTGG,, (SEQ ID NO. 44)
RTADZ-68: AGGGCTCTCTTGAAATTGTCTG,,
and
                                       (SEQ ID NO. 45)
ADZ1603:  GACAGGTGTGTGGATCCCGAAG.
``` rrp6Δ dis3-G833R and rrp6Δ dis3-R847K strains were obtained through crossing rrp6Δ strain with either ADZY783 or ADZY685. Spores were dissected and double mutants were selected. Spores harboring RRP6 deletion together with either DIS3 G833R or R847K mutation gave strains ADZY732 and ADZY742, respectively.

Diploid strains harboring mutations in both PIN and RNB domains of Dis3 - dis3-D171N G833R-pA/DIS3 WT (ADZY713) and dis3-D171N R847K-pA/DIS3 WT (ADZY716), were obtained as follows. Diploid BMA64 strain was transformed with a DNA fragment containing DIS3 gene harboring D171N mutation (mutation in PIN domain) and G833R or R847K mutation (mutation in RNB domain), respectively, a tag (encompassing TEV protease cleavage site and sequence encoding protein A) and the TRP selection marker. First, two parts of the DIS3 gene were amplified: 5'—using ADZKD106-ADZKD141 (CCTAAATAGAGCATTCAACGGTGACCAGG) (SEQ ID NO. 46). primer pair and total genomic DNA isolated from ADZY531 strain (with the DIS3 locus containing D171N mutation in the PIN domain) as a template; and 3'—with ADZKD142 (CCTGGTCACCGTTGAATGCTCTATT-TAGG) (SEQ ID NO. 47).—ADZKD107 primer pair, employing total genomic DNA isolated from ADZY783 or ADZY685 (with the DIS3 locus containing G833R or R847K mutation), respectively, as template. The full-length amplicons with the desired mutations were obtained with ADZKD 106 and ADZKD 107 primers in overlap PCR (where products of the 5' and 3' amplifications served as templates), and were subsequently used for transformation. Selected transformants gave desired strains.

Yeast Growth Assays.

Yeast strains described above were grown in complete YPD medium at 30° C. overnight until $OD_{600}$ reached 0.2 before spotting serial dilutions onto YPD plates. Cell growth was analyzed after 60 h of incubation at 25° C., 30° C. or 37° C. Analysis of viability for strains harboring mutations in both PIN and RNB domains of Dis3 was carried out by sporulation of ADZY713 and ADZY716 diploid strains, followed by tetrad dissection.

Rna Isolation and Northern-Blot Analysis.

RNA was isolated from yeast cultures using standard hot acid phenol procedure Northern blots were handled according to standard procedures and probed either at 42° C. (5'-labeled oligonucleotide probes) or at 63° C. (DNA fragments labeled by random-priming).

For detection of yeast 5'-ETS and NEL025 CUT, PCR probes labeled by random-priming with $\alpha$-$^{32}$P[dATP] and DecaLabel DNA Labeling Kit (ThermoScientific), as described in Lebreton et al. 2008 were employed. For other transcripts, $^{32}$P-labeled oligonucleotides were used as probes. Sequences of these oligonucleotides were the following: yeast 7S antisense oligo—GGCCAG-CAATTTCAAGTTA (SEQ ID NO. 48), yeast 5.8S antisense oligo—GCGTTGTTCATCGATGC (SEQ ID NO. 49), yeast 5S antisense oligo—CTACTCGGTCAGGCTC (SEQ ID NO. 50). After hybridization membranes were washed and exposed to PhosphorImager screens (FujiFilm), which were scanned following exposure using a FLA 7000 scanner (FujiFilm).

Western Blotting.

Protein samples from yeast cultures were run in 10-12% SDS-PAGE gels and immobilized on Protran nitrocellulose membranes (Whatman) Protein A tag was detected directly by using rabbit Peroxidase-Anti-Peroxidase Soluble Complex antibody (Sigma-Aldrich; P1291) (1:3000). Eventually, blots were developed in Curix 60 machine (AGFA), using Immun-Star™ WesternC™ Kit (Bio-Rad) and CL-XPosure™ Films (Thermo Scientific).

The functional analyses of hDIS3 MM mutations were started with the construction of yeast strains expressing endogenous Dis3 with introduced equivalent amino acid changes. It was possible to produce all mutants except dis3-S541R (S477R in humans). First, basic growth tests were performed and it was noticed that dis3-G833R (G766R in humans) and dis3-R847K (R780K in humans) strains display a strong growth retardation phenotype in comparison with the wild-type control, even at physiological temperature (FIG. 3A). In the case of dis3-G833R mutant growth defect was even stronger than that observed for dis3-D551N (D487N in humans) catalytic mutant. On the other hand, while the two remaining mutant strains—dis3-V568G (V504G in humans) and dis3-A588P (A524P in humans)—grew normally at 30° C., they appeared to be extremely thermosensitive, as their growth was virtually completely abolished at the elevated temperature (FIG. 3A). Results of growth tests of yeast DIS3 mutants provided the first in vivo support that amino acids changed in MM patients are important for the exosome function. Moreover, as observed above in the preceding in vitro analyses, substitution of V568 (V504 in hDIS3) led to milder defect than changes of G833 (G766 in hDIS3) or R847 (R780 in hDIS3) (FIG. 3A). Also, the phenotype of the two G833 and R847 mutations in *S. cerevisiae* in rrp6Δ background was tested and it was found that such a combination results in a slightly synergistic growth inhibition (FIG. 3A).

Then, the molecular effects of DIS3 gene mutations in yeast were tested by northern-blot analyses on total RNA samples isolated from mutant and control strains, using probes detecting typical exosome substrates: 5'-ETS by-product of ribosomal RNA processing, NEL025 CUT (cryptic unstable transcript) and 7S precursor in 5.8S rRNA maturation pathway. It was observed that all DIS3 mutations (genuine D551N catalytic one and four corresponding to those found in MM patients) cause comparable accumulation of full-length 5'-ETS and 7S rRNA with regard to their amounts in wild-type strain (FIG. 3B). On the other hand, looking carefully on the levels of 7S and 5'-ETS degradation intermediates, as well as NEL025 CUT, the DIS3 mutations could be divided into two classes: the one encompassing D551N, G833R and R847K amino acid changes led to more significant accumulation of all above-mentioned species than another, represented by V568G and A588P substitutions (FIG. 3B). Again, this is in concordance with the facts that: 1) the respective mutant hDIS3 proteins displayed different phenotypes in the in vitro biochemical assays (FIG. 2); 2) mutant yeast strains demonstrated variable growth defects (FIG. 3A).

The observed phenotypes are not due to the lack of expression of the respective DIS3 mutants, as confirmed by western blotting against the protein A tag which was introduced at the 3'-end of all inserts employed during generation of the strains (FIG. 3C).

Combining DIS3 G833R or R847K mutation with deletion of RRP6 gene did not seem to remarkably enhance the analyzed molecular phenotypes (maybe except additional accumulation of NEL025 CUT in rrp6Δ dis3-G833R in comparison with dis3-G833R single mutant) (FIG. 3B). On the other hand, no strains which would harbor G833R or R847K mutation in the background of D171N were isolated (FIG. 3D), while D171N was previously shown to abolish PIN domain endonucleolytic activity (Lebreton et al. 2008). It indicates that RNB domain mutations analogous to those associated with MM in humans are in yeast synthetically lethal with simultaneous inactivation of endonuclease, similarly to what was observed for the genuine catalytic RNB domain mutation, D487N (Lebreton et al. 2008).

Altogether, experiments performed using the yeast model showed that changing amino acids in Dis3 positions analogous to those cancers in which hDIS3 activity is changed, especially in mutations in RNB domain being equivalent of mutations observed in multiple myeloma patients inhibits S. cerevisiae growth through the impairment of the exosome ability to exonucleolytically degrade its physiological substrates.

Example III

MM-Associated hDIS3 Mutations Result in Accumulation of Different RNA Species in Human Cellular Model.

A multistep cloning procedure for generation of vectors for co-expression of different versions of recoded hDIS3 with FLAG epitope at the C-terminus and sh-miRNAs directed against endogenous hDIS3 mRNA was the following. First, inserts encompassing open reading frames coding for WT, RNB MUT (D487N), G766R and R780K variants of hDIS3 were amplified with D3FMluI: (ATATACGCGT-GCCGCCACCATGCTCAAGTCCAAGACGTTC) (SEQ ID NO. 51) and D3RB120I: (GCGCGGGCCCTTACTT-GTCGTCGTCGTCCTTGTAATCTAT ATCTTTTC-CAAGCTTCATCTTCT) (SEQ ID NO. 52) primer pair and using pHEX1, pHEX8, pMM4 or pMMS constructs as respective templates. Next, the inserts were cloned into MluI and Bsp120I sites of BI-16 vector (Sammarco and Grabczyk, 2005), thus replacing hRLUC ORF present therein, with the use of E. coli MH1 strain. This way, [BI-16'] hDIS3 WT, [BI-16'] hDIS3 RNB MUT, [BI-16'] hDIS3 G766R and [BI-16'] hDIS3 R780K transitory vectors were constructed. hDIS3 inserts were sequenced as above.

In parallel, a search was performed for miRNA sequences that should specifically and efficiently target endogenous hDIS3 mRNA, using BLOCK-iT™ RNAi Designer tool from Invitrogen (with "miR RNAi" option) (http://rnaidesigner.invitrogen.com/rnaiexpress). Candidate sequences were chosen, ranked as 1., 3., 5., 6. and 7. (with the highest scores returned by the program; sequences ranked as 2. and 4. were rejected, as they partially overlapped with 1. and 3.), starting at positions 495., 898., 1159., 1273. and 1404. of hDIS3 ORF, respectively. Basing on the general idea of BLOCK-iT™ Pol II miR RNAi Expression Vector Kits from Invitrogen (http://www.invitrogen.com/site/us/en/home/Products-and-Services/Applications/rnai/Vector-based-RNAi/Pol-II-miR-RNAi-Vectors.html), then a synthetic DNA fragment was designed, encompassing a combination of miRNA sequences listed above miR1159-miR1273-miR1404 (tri-miR2) which was utilized in further experiments. It encoded three tandemly positioned shRNAs corresponding to pre-designed miRNAs—so-called sh-miRs, where sense and antisense miRNA sequences were separated by the loop element enabling formation of the hairpin. Each of the sh-miR sequence was flanked at both termini with motifs ensuring correct miRNA processing from the artificial pre-miRNA precursor, following a natural miRNA biogenesis pathway active in human cells. In addition, polyadenylation signal derived from the gene encoding herpes simplex virus thymidylate kinase (HSV-TK-pA) was placed at the 3'-end of this synthetic cassette, allowing for correct termination of transcription in human cells. The cassette contained EcoRI/SalI and ClaI/HindIII restriction site combinations at the 5' and 3' extremities, respectively, which were used in subsequent cloning steps. It was synthesized by BlueHeronBio and inserted between EcoRI and HindIII sites of pUCAmpMinusMCS vector. Next, a sequence encoding eGFP (allowing for monitoring of expression of the cassette containing artificial pre-miRNA) was amplified in PCR using eGFPFor
(SEQ ID NO. 53)
(GCGGAATTCATATACCTAGGACCATGGTGAGCAAGGGCGAGGAGC), eGFPRev
(SEQ ID NO. 54)
(GCGCGTCGACTCACTACCTCCTCTTACTTGTACAGCTCGTCCATGC)

primer pair and pEGFP-N1 plasmid (Clontech) as a template and inserted into EcoRI and SalI sites of the provided [pUCAmpMinusMCS] tri-miR 2 plasmid, thus giving [pUCAmpMinusMCS] eGFP-tri-miR 2 transitory construct. Additionally, a site recognized by XmaJI restriction endonuclease was introduced in eGFPFor oligonucleotide upstream the 5'-end of eGFP ORF, which was used at further cloning stage.

In the next phase of construct generation, it was necessary to change the sequence of exogenous hDIS3 ORF in order to make it insensitive to miRNA action. To this end, a synthesis of recoded hDIS3 fragment encompassing nucleotides 451.-1457. of the open reading frame was ordered. It is worth noting that this fragment covered all five sites that were initially aimed to be targeted with miRNA, and—on the other hand—it was located outside the region where D487N (RNB MUT), G766R and R780K mutations had been earlier introduced. The idea of recoding was to introduce synonymous mutations into all possible codons (at those positions where degeneration of genetic code could be utilized) within the fragment containing sites recognized by miRNA and taking codon usage frequency into account, so that the sequence would be as much divergent from the initial one as possible. Recoded hDIS3 ORF fragment was synthesized by BlueHeronBio, also as an insert in pUCAmp-MinusMCS vector, surrounded with ~30-45 nt-long flanking regions fully complementary to the initial sequence and terminated at both extremities with sites recognized by SchI restriction enzyme—an endonuclease cleaving DNA at some distance from its site and leaving blunt ends following cleavage. Owing to the presence of such termini, the insert could be excised from the provided [pUCAmpMinusMCS] rec$_{13}$ hDIS3 plasmid (propagated in *E. coli* MH1 strain) with SchI and then utilized as a "megaprimer" in overlap extension PCR (Bryksin and Matsumura, 2010), employing [BI-16'] hDIS3 WT, [BI-16'] hDIS3 RNB MUT, [BI-16'] hDIS3 G766R and [BI-16'] hDIS3 R780K plasmids generated in the first step (see above) as templates. Products were digested with DpnI restriction enzyme and introduced to *E. coli* MH1 strain by transformation. This gave rise to [BI-16'] hDIS3rec WT, [BI-16'] hDIS3rec RNB MUT, [BI-16'] hDIS3rec G766R and [BI-16'] hDIS3rec R780K transitory constructs, respectively. The presence of recoded fragment was checked by digestion with AdeI restriction enzyme and sequencing, using primers: HD3F1848, HD3F2429, hD3r8l9R-CTTGTTCTCCTCGGAATCTC (SEQ ID NO: 55), HD3R1592 and HD3R2443.

The aim of the ultimate cloning stage was to transfer a DNA fragment containing a co-cistron of eGFP coding sequence and pre-miRNA/HSV-TK-pA from [pUCAmpMinusMCS] eGFP-tri-miR 2 construct to each of the four BI-16 vector derivatives from the previous step, through replacement of the FLUC ORF present in the latter. To this end, all plasmids were propagated in *E. coli* dam-/dcm-strain prior to the standard cloning procedure, utilizing XmaJI and ClaI restriction sites, followed by transformation of the ligation products into *E. coli* MH1 strain. This eventually led to the generation of final constructs: pMM7, pMM8, PMM9, pMM10. Both hDIS3rec and eGFP-tri-miR 2 inserts were sequenced using primers: HD3F1848, HD3F2429, hD3r8l9R, HD3R1592 and HD3R2443, BI16seq1-CAT-TCTCCGCTCCATCGTTC (SEQ ID NO: 56) and BI16seq2-TCCACTGGTCGACTCACTAC (SEQ ID NO: 57).

Cell Culture and Generation of Stable Cell Lines.

HEK293 Flp-In T-REx (Invitrogen) cells were cultured as monolayers in Dulbecco's modified Eagle's medium (D-MEM, Gibco), supplemented with 10% tetracycline-free foetal bovine serum (TET System Approved FBS, Clontech) and antibiotics (Penicillin-Streptomycin; Sigma-Aldrich) at 37° C. in a 5% $CO_2$ humidified atmosphere. The stable inducible HEK293 Flp-In T-REx cell lines were obtained in this study using the Flp-In™ T-REx™ system (Invitrogen), with the use of pMM7, pMM8, PMM9, pMM10 constructs (highly pure Midi preps of plasmid DNA), were grown in the same conditions as above, supplemented with hygromycin B (100 µg/ml) and blasticidin (10-15 µg/ml) (both from Invitrogen). Transfections were done with Lipofectamine2000 (Invitrogen). Expression of exogenous genes was induced by addition of doxycycline to the culture medium at the final concentration of 100 ng/ml.

RNA Isolation and Northern-Blot Analysis.

RNA was isolated from human cell lines using TRI Reagent (Sigma-Aldrich). and followed by RNA immobilization to membrane Northern blots were handled according to standard procedures.

Randomly-primed PCR products, obtained with the use of primer pairs:

```
                                         (SEQ ID NO: 58)
        GAPDH_F (TGCACCACCAACTGCTTAGC)

(SEQ ID NO: 59)
        -GAPDH_R (GGCATGGACTGTGGTCATGAG),
        and
                                         (SEQ ID NO: 60)
        7SL_F (TCGGGTGTCCGCACTAAGTT)

(SEQ ID NO: 61)
        -7SL-R (TGGCTATTCACAGGCGCGAT).
``` were used as probes for detection of GAPDH mRNA and 7SL RNA, respectively. Randomly-primed probe, generated as described in (Tomecki et al. 2010b; Supplementary Information) was used for detection of hDIS3 transcript. Randomly-primed DNA probe specific to histone H2A mRNA was generated by EcoRI/HindIII-mediated excision of sequence corresponding to its full-length CDS (GenBank ID: AY131971.1), cloned between respective sites of pUC19; the construct was kindly provided by Prof. Zbigniew Dominski. For other transcripts, $^{32}$P-labeled oligonucleotides were used as probes. Sequences of these oligonucleotides were according to Table 4.

TABLE 4

$^{32}$P-labeled oligonucleotides used as probes.

| Probe name | Probe sequence | SEQ ID NO |
|---|---|---|
| human 5.8S rRNA precursor antisense oligo | GCGATTGATCGGCAAGCGA | 62 |
| human 5.8S rRNA antisense oligo | TCCTGCAATTCACATTAATTCTCGCAGCTAGC | 63 |
| human 5S rRNA antisense oligo | CATCCAAGTACTAACCAGGCCC | 64 |
| human tRNA AsnGTT antisense oligo | ACCAACCTTTCGGTTAACAGCCGAACGCGC | 65 |
| human tRNA AspGTC antisense oligo | CGGTCTCCCGCGTGACAGGCGGGGATACTC | 66 |
| human tRNA HisGTG antisense oligo | CGAGGTTGCTGCGGCCACAACGCAGAGTAC | 67 |

TABLE 4-continued $^{32}$P-labeled oligonucleotides used as probes.

| Probe name | Probe sequence | SEQ ID NO |
|---|---|---|
| human tRNA TrpCCA antisense oligo | CGCAACCTTCTGATCTGGAGTCAGACGCGC | 68 |
| human tRNA TyrGTA antisense oligo | GACCTAAGGATCTACAGTCCTCCGCTCTAC | 69 |
| human tRNA LysTTT (1,2) antisense oligo | GACCCTCAGATTAAAAGTCTGATGCTCTAC | 70 |
| human tRNA PheGAA antisense oligo | GGACCTTTAGATCTTCAGTCTAACGCTCTC | 71 |
| human tRNA CysGCA antisense oligo | GGGACCTCTTGATCTGCAGTCAAATGCTCT | 72 |
| human RNase P RNA antisense oligo | ATGGGCGGAGGAGAGTAGTCTG | 73 |
| human RNase MRP RNA antisense oligo | GCCGCGCTGAGAATGAGCCCC | 74 |
| human U2 snRNA antisense oligo | GGGTGCACCGTTCCTGGAGGTACTGCAATA | 75 |
| human U5 snRNA antisense oligo | TTGGGTTAAGACTCAGAGTTGTTCCTCTCC | 76 |
| human U6 snRNA antisense oligo | GAACGCTTCACGAATTTGCG | 77 |
| human U3 snoRNA antisense oligo | ACCACTCAGACCGCGTTCTCTCCCTCTCAC | 78 |

After hybridization membranes were washed and exposed to PhosphorImager screens (FujiFilm), which were scanned following exposure using a FLA 7000 scanner (FujiFilm).

Western Blotting.

Protein samples from human cell lines were treated as described in Example II for Western blotting and incubated with one of the following primary antibodies: mouse monoclonal anti-eGFP (B2) (Santa Cruz Biotechnology; sc-9996) (1:1000), rabbit polyclonal anti-FLAG (Sigma-Aldrich; F-7425) (1:3000), rabbit polyclonal anti-hDIS3L (Sigma-Aldrich; HPA041805, lot: R38591) (1:500), rabbit polyclonal anti-hRRP6 (Sigma-Aldrich; P4124) (1:3000), rabbit polyclonal anti-hDIS3L2 (home-made; see Lubas et al. 2013) (1:2000), goat polyclonal anti-GAPDH (V-18) (Santa Cruz Biotechnology; sc-20357) (1:2000). Membranes were then washed with TBST and incubated with appropriate secondary antibody (goat anti-mouse, goat anti-rabbit (Calbiochem; 401215, 401393, respectively) or rabbit anti-goat (Sigma-Aldrich; A5420)) conjugated with horseradish peroxidase. Eventually, blots were developed in Curix 60 machine (AGFA), using Immun-Star™ WesternC™ Kit (Bio-Rad) and CL-XPosure™ Films (Thermo Scientific).

Immunolocalization Analysis.

$2 \times 10^4$ cells of HEK293 Flp-In T-Rex-derived stable cell lines were plated onto chamber slides (Thermo Scientific), in a medium with doxycycline (100 ng/ml) to induce protein expression. Cells were fixed permeabilized and blocked. Cells were incubated, first with primary antibody and then with secondary antibody coupled to fluorophore. Finally, cells were stained with DAPI (Invitrogen) After the final wash coverslips were mounted on chamber slides in Pro-Long Gold antifade reagent (Invitrogen), left in the dark overnight at 25° C. and then stored at 4° C. until microscopic analysis. The following antibodies were used (dilutions in parentheses): 1) primary-mouse monoclonal anti-FLAG (M2) (Sigma-Aldrich; F3165) (1:200); rabbit polyclonal anti-hDIS3 (Sigma-Aldrich; HPA039281, lot: R37348) (1:100); rabbit polyclonal anti-fibrillarin (Abcam; ab5821) (1:150); 2) secondary—Alexa Fluor 635-conjugated goat anti-mouse, Alexa Fluor 555-conjugated goat anti-rabbit IgG, Alexa Fluor (both from Molecular Probes) (1:800). Imaging was performed on a FluoView FV1000 system with spectral detectors (Olympus), using appropriate emission filters and a 60×/1.40 oil immersion objective lens. Images were processed using the FluoView software.

Polysome Gradients and RNA Isolation.

Stable cell lines were grown overnight in a medium containing doxycycline on one plate until reaching ~95% confluence. Cells were treated with cycloheximide (Sigma-Aldrich; 200 µg/ml) at 37° C. for 15 minutes, harvested by trypsinization, spun down for 1 minute at 500 xg; 4° C. and then washed 3 times with ice-cold PBS containing 100 µg/ml cycloheximide. After final wash and complete removal of PBS, the cells were suspended in 0.5 ml of lysis buffer (10 mM Hepes-KOH, pH=7.5; 100 mM KCl; 2.5 mM MgCl$_2$; 1 mM DTT; 100 µg/ml cycloheximide; 1 mg/ml heparin (Sigma-Aldrich); 1% reduced Igepal-CA630 (Sigma-Aldrich); 80 u/µl RiboLock™ RNase Inhibitor (Thermo Scientific); 1 x Protease Inhibitor Cocktail, Complete EDTA-free (Roche)), lysed by thorough pipetting and incubation for 15 minutes at 4° C. on a rotating wheel. Lysates were then centrifuged for 10 minutes at 10000 xg; 4° C. and RNA concentration in collected supernatants was measured using Nanodrop 2000 c device (Thermo Scientific). 8 OD$_{260}$ units of cytoplasmic lysates in 500 µl of lysis buffer were layered onto 7-47% sucrose gradients (prepared using filtered sucrose solutions in lysis buffer, lacking detergent and ribonuclease inhibitor) and ultracentrifuged for 2 hours at 39000 xg; 4° C. in SW-41 Ti rotor (Beckman Coulter). Subsequently, 0.5 ml fractions were collected from each gradient by pumping 60% sucrose solution (prepared as above) to the bottom of tubes and OD$_{260}$ was monitored on ÄKTA Purifier. For RNA isolation from polysome gradients, collected fractions were thoroughly mixed with 650 µl of phenol: guanidine thiocyanate (1:1) by vortexing and incubated at 65° C. for 8 minutes. Then, 320 µl of chloroform and 120 µl of 3M sodium acetate (pH=5.2) were added, followed by vortexing and centrifugation for 5 minutes at 13200 rpm. Samples were extracted twice with chloroform and RNA was precipitated from aqueous phase with isopropanol, washed with 75% ethanol and suspended in 20 µl of RNase-free water. RNA samples were subsequently pooled and analysed by northern-blotting.

siRNA Transfection.

siRNA-mediated knockdown was done using stealthRNA and Lipofectamine RNAiMAX (Invitrogen). The stealthRNA oligo against hRRP6 (ID HSS182420) or negative control (Stealth™ RNAi Negative Control Low GC) (both from Invitrogen) were used at the final concentration of 20 nM. The cells were grown in the absence or presence of doxycycline for additional 60 hours before harvesting.

Reverse Transcription and Quantitative PCR.

Figure 4A:
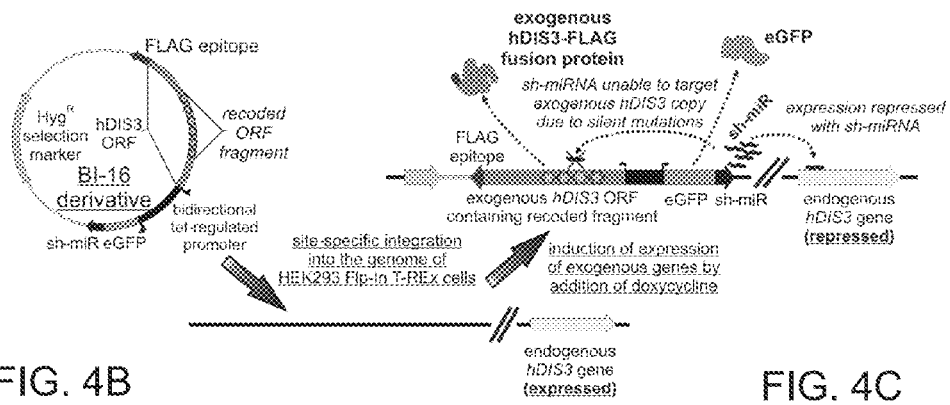
FIGS. 4A-D. Characterization of the constructed human model cell lines. (A) General principle of the constructed human cellular model. Derivatives of BI-16 vector (compatible with Flp-In T-Rex system from Invitrogen) containing: 1) wild-type or mutated version of FLAG-tagged hDIS3 ORF with recoded region and 2) eGFP-sh-miRNA fusion, both under the control of bidirectional tetracycline-regulated promoter, were integrated into the genome of HEK293 Flp-In T-REx cell line; upon induction with doxycycline each of the generated stable cell lines produced a given variant of hDIS3-FLAG fusion and sh-miRNA, designed in a way ensuring that only the expression of endogenous hDIS3 copy (but not exogenous sequence encoding hDIS3-FLAG, encompassing sh-miRNA-insensitive recoded fragment within the ORF) was silenced; production of sh-miRNA was monitored by eGFP co-expression. (B) Northern-blot analysis of hDIS3 expression; total RNA was isolated from cell lines containing exogenous sequences coding for wild-type or mutated hDIS3 versions, either uninduced (lanes "−dox") or subjected to doxycycline treatment (lanes "+dox"); following electrophoretic separation in denaturing agarose gel, RNA was transferred onto membrane, which was then sequentially hybridized with probes complementary to the 5'-terminal part of hDIS3 ORF or to GAPDH (loading control). (C) Western-blot analysis of the expression of FLAG-tagged hDIS3 variants and eGFP-sh-miR fusion; protein samples were prepared from the same cell lines as in (B), separated in SDS-PAGE gel and transferred onto nitrocellulose membrane, which was then probed with anti-FLAG or anti-eGFP antibody; staining of the membrane with Ponceau S Red was utilized as a loading control. (D) Western-blot analysis of the expression of other human proteins displaying 3'-5' exoribonucleolytic activity; protein samples were analyzed as in (C), but using antibodies specific to hDIS3L, hRRP6 or hDIS3L2.
Figure 4B:
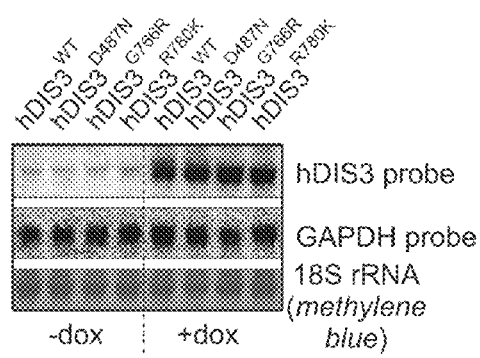
Figure 4C:
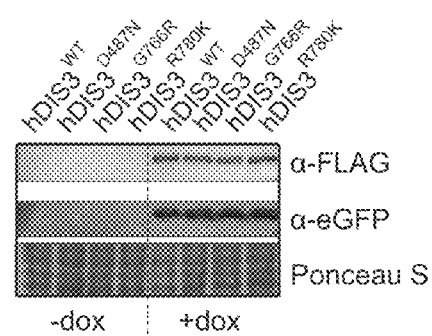
Figure 4D:
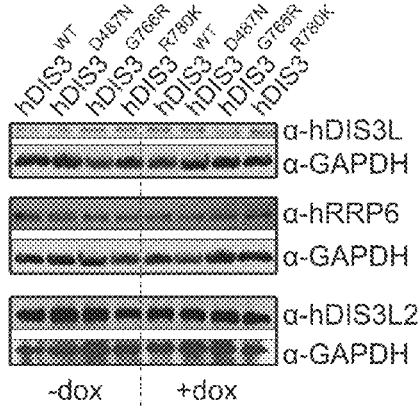
Figure 5A:
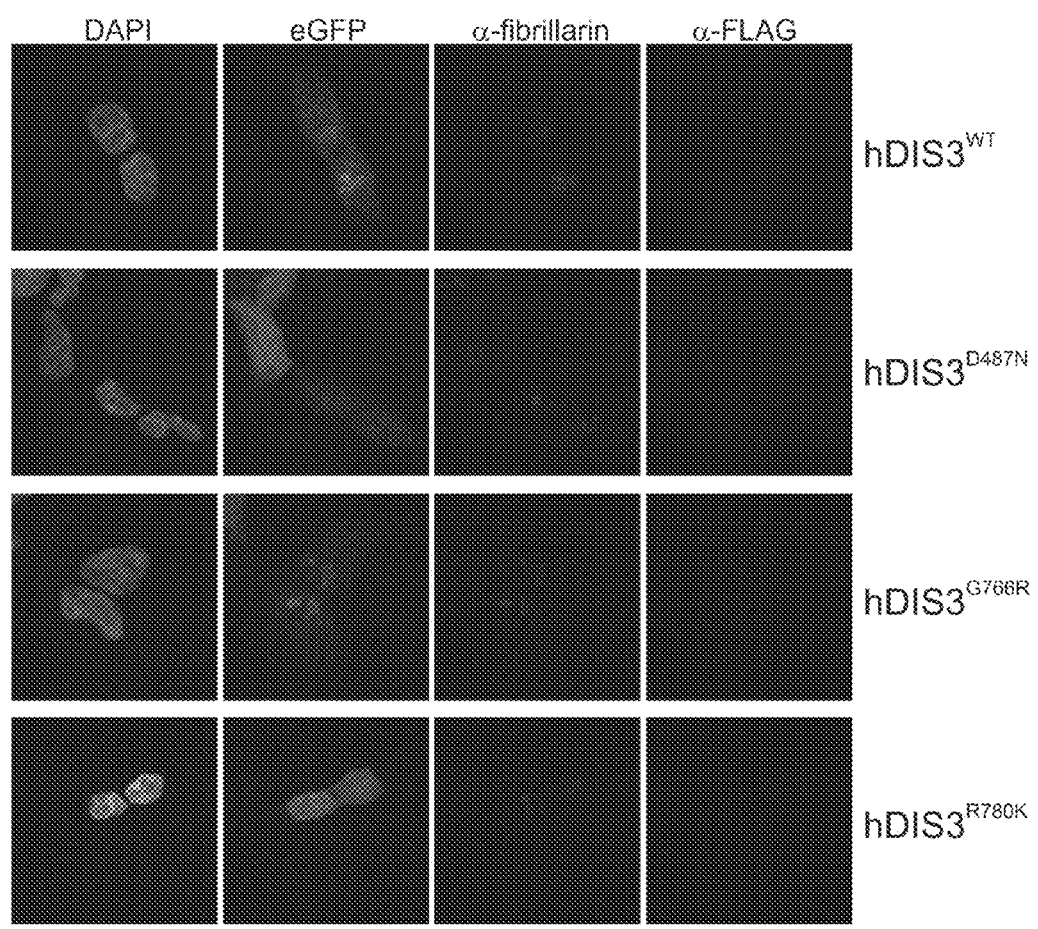
FIGS. 5A-B. Overexpressed exogenous hDIS3 variants display proper intracellular localization. (A) Model cell lines bearing exogenous sequences coding for different FLAG-tagged versions of hDIS3 were subjected to induction, followed by immunofluorescence using anti-FLAG and anti-fibrillarin (nucleolar marker) antibodies (detected with secondary antibodies coupled with Alexa Fluor 635 and 555 fluorescent dyes, respectively) in combination with DAPI staining of the nuclei; eGFP fluorescence was used to monitor the expression of eGFP-sh-miR fusion; hDIS3-FLAG fusions seemed to localize in the nucleoplasm, while they were clearly excluded from the nucleoli; weak cytoplasmic staining was also visible. (B) Cells were analyzed by immunofluorescence as above, but using only anti-hDIS3 antibody (detected with secondary antibody coupled with Alexa Fluor 555); a signal, corresponding to both endogenous and exogenous hDIS3, arose only from the nucleoplasm, but was absent from the nucleoli.
Figure 5B:
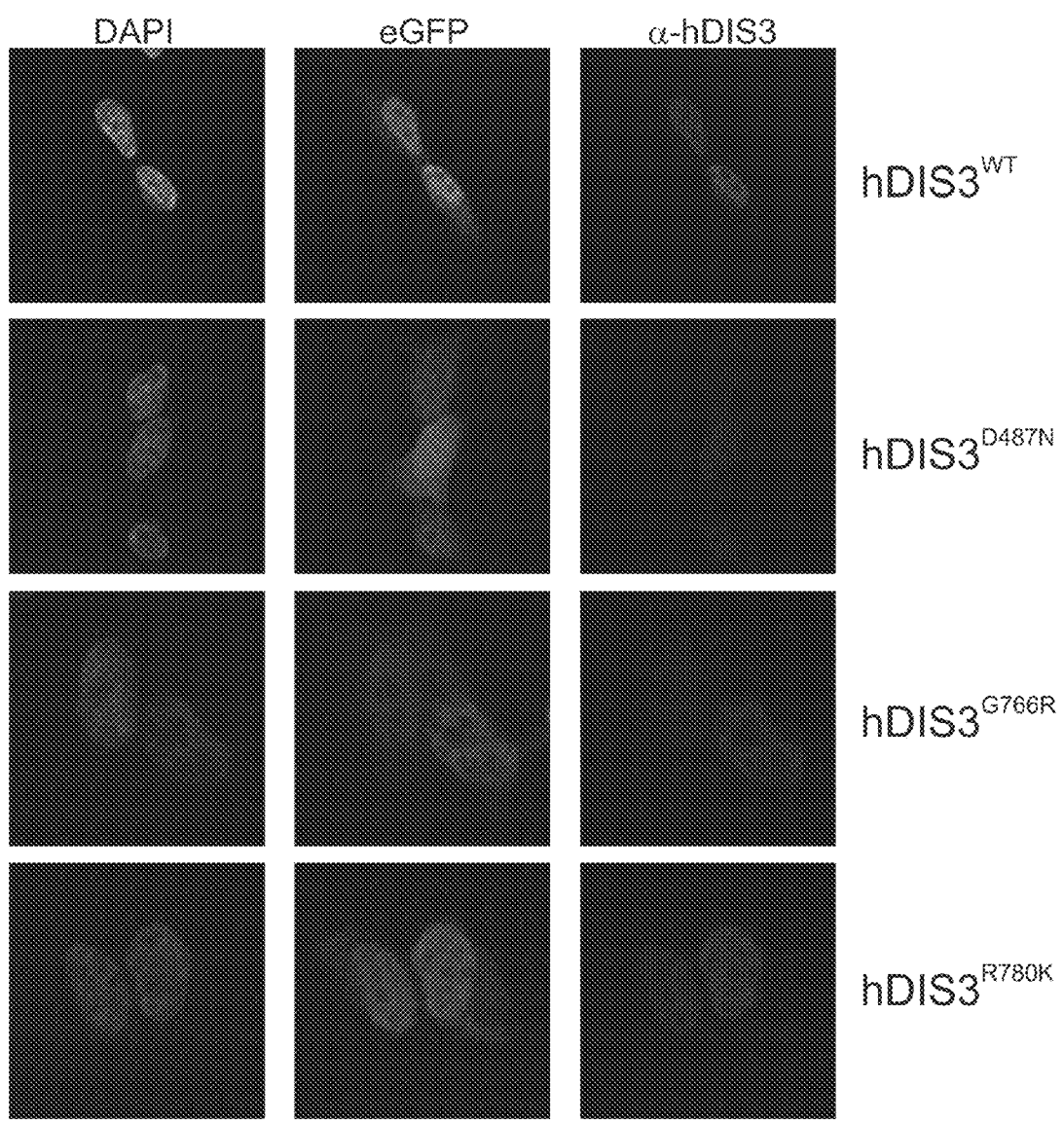

10 μg of total RNA extracted from stable human cell lines were treated with 6 units of TURBO™ DNase (Ambion), in the presence of RiboLock™ RNase Inhibitor (Thermo Scientific), Following extraction, 2 μg of DNase-treated RNA was reverse transcribed by using a mixture of 50 pmol of an oligo(dT) primer and 250 ng of random hexamers (Invitrogen) and Superscript III™ reverse transcriptase (Invitrogen) 1/100 of a cDNA reaction was mixed with Platinum® Quantitative PCR SuperMix-UDG (Invitrogen), 2.5 pmol of each primer and 0.3 μg BSA in triplicates, in a final volume of 10 μl and applied to real-time PCR analysis in a Roche LightCycler® 480 system using an annealing temperature of 58° C. Negative controls lacking reverse transcriptase showed a negligible background. All data were normalized to GAPDH mRNA. The following specified in Table 5 primer pairs were used for amplification.

exogenous hDIS3 variant tagged with FLAG epitope and containing a recoded fragment in order to make it insusceptible to miRNA action (FIG. 4A). Four such cell lines were established, exogenously overproducing either hDIS3$^{WT}$, genuine catalytic mutant hDIS3$^{D487N}$ or one of the two hDIS3 variants associated with multiple myeloma that had been examined in all previous experiments and gave strongest phenotypes, in particular in the yeast model— hDIS3$^{G766R}$ and hDIS3$^{R780K}$. Northern- and western-blot analyses confirmed that both inserts were efficiently expressed in all four cell lines (FIG. 4B,C). Before starting experiments with the model cell lines, it was verified that the expression of other known human 3'-5' exonucleases involved in RNA metabolism, both cooperating with the exosome core—hDIS3L and hRRP6, and functioning independently of the complex (hDIS3L2) remains unchanged in this experimental system (FIG. 4D). Furthermore, immunolocalization experiments on these cell lines were performed in order to be sure that neither overexpression of hDIS3 nor the introduced mutations influence the intracellular localization of the protein (FIG. 5A, B).

With the use of the model cell lines, it was examined whether expression of mutated versions of hDIS3 protein leads to aberrations in metabolism of RNA molecules representing various classes. To this end, total RNA from the

TABLE 5

| Name | Sequence of primers (Forward/Reverse) | SEQ ID NO |
| --- | --- | --- |
| GAPDH | GTCAGCCGCATCTTCTTTTG/GCGCCCAATACGACCAAATC | 79/80 |
| 40-2b PROMPT | GGGAGTCTAAGGAAAAGGAG/CAGTGAAAGGAGAGCGTATC | 81/82 |
| 40-13 PROMPT | GGAAATAGTGGAGAAAAGCA/CATTTTTGAAGGAACGGTAG | 83/84 |
| 40-33 PROMPT | CTGGCCTAGCTAAAGTCTCA/TCTGCTCCTAGCTCTCAGTC | 85/86 |
| 40-52 PROMPT | AGTTCCAAGAAACCACACAC/GGTCGTTTGAGTGGACTAAC | 87/88 |
| 40-13 gene | GGAGTTGACAGCAGAGTTTT/ATGCACTTTAACCAGGTTTG | 89/90 |
| 40-33 gene | GGTGACAACTGGTCTCTGTC/CCGAAAGTTACCAAAACATT | 91/92 |
| 40-52 gene | AAAATGAGACTGGCCACTAA/GATGTGGGATTCTCTCAAAC | 93/94 |
| mtATP6/8 | CCATCAGCCTACTCATTCAACC/GCGACAGCGATTTCTAGGATAG | 95/96 |

Since the results of biochemical analyses and experiments performed using yeast cells were quite promising, it prompted to test the impact of hDIS3 mutations in humans using a proper cellular model. The most appropriate would be obviously multiple myeloma cell lines bearing different hDIS3 variants. However, sequence analysis that were performed for several commercially available MM cell lines from patients did not reveal presence of mutations in hDIS3 gene (data not shown). On the other hand, although I845V mutation was present in SKMM1 cell line (data not shown), it was not advantageous to use this line since the mutation does not influence the exoribonucleolytic activity of the enzyme (FIG. 1C and 2). Therefore, it was necessary to construct a novel cellular model, which would allow to analyze the influence of hDIS3 mutations on cell physiology and RNA metabolism. This goal was achieved through combining Flp-In™ T-REx™ system from Invitrogen with the use of compatible vector containing bidirectional tetracycline-inducible promoter (Sammarco & Grabczyk, 2005) (FIG. 4A). This experimental setup allowed to generate HEK293 Flp-In T-REx cell lines stably co-expressing: 1) sh-microRNA that silenced endogenous hDIS3 copy and 2)

cell lines was isolated, which cell lines were either untreated or subjected to doxycycline-mediated induction for 48 hours. It is important to note that following such period of induction, cell lines expressing hDIS3$^{D487N}$ and hDIS3$^{R780K}$ (mutant proteins grew slightly worse than those producing hDIS3$^{WT}$ or hDIS3$^{G766R}$ variants.

Figure 6A:
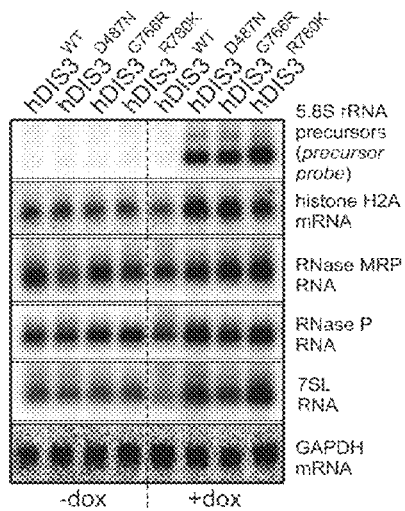
FIGS. 6A-E. Model cell lines producing mutated hDIS3 variants accumulate transcripts representing various RNA classes. (A) Low-resolution northern-blot analysis of steady-state levels of RNA molecules synthesized by different RNA polymerases; total RNA was isolated from cell lines containing exogenous sequences coding for wild-type or mutated hDIS3 versions, either uninduced (lanes "−dox") or subjected to doxycycline treatment (lanes "+dox"); following electrophoretic separation in denaturing agarose gel, RNA was transferred onto membrane, which was then sequentially hybridized with probes recognizing RNA pol I (5.8S rRNA precursor), RNA pol II (histone H2A mRNA, GAPDH mRNA) or RNA pol III transcripts (RNase P RNA, RNase MRP RNA, 7SL RNA); signals were visualized by phosphorimaging; significant increase in levels of 5.8S rRNA 3'-extented precursors was visible upon induction, while more modest accumulation was apparent for histone H2A transcript, as well as in the case of RNase P and 7SL RNAs. (B) High-resolution northern-blot analysis of 5.8S rRNA and its precursor; the same RNA samples as in (A) were resolved in denaturing polyacrylamide gels for 1 hour or for 2 hours ("longer run" in the upper part of the Figure); following transfer, membranes were hybridized with probes complementary either to mature 5.8S rRNA or to the region located downstream its 3' border (precursor probe); 5S rRNA was utilized as a loading control; accumulation of slightly different precursors was observable depending on which mutant hDIS3 variant was produced, without concomitant decrease of mature 5.8S rRNA levels. (C) High-resolution northern-blot analysis of tRNAs; RNA samples analogous to those in (A) were separated in denaturing polyacrylamide gels and further analyzed as above, using probes complementary to different tRNAs; induction-dependent accumulation was observed for the majority of analyzed tRNAs and precursors of tRNA$^{Tyr}$ and tRNA$^{Cys}$, particularly in cells producing hDIS3$^{D487N}$ and hDIS3$^{R780K}$ proteins; hybridization with the probe specific to 5.8S rRNA served as positive control of the experiment. (D) High-resolution northern-blot analysis of selected sn/snoRNAs; RNA samples analogous to those in (A) were analyzed as above, using probes specific to three different snRNA and U3 snoRNA; induction-dependent accumulation was noticeable in the case of U5 snRNA; hybridizations with the probes specific to 7SL RNA and 5.8S rRNA served as positive controls of the experiment. (E) Quantitative PCR analysis of different PROMPT regions and corresponding protein-coding transcripts in cell lines bearing various hDIS3 mutations; the graph shows results of quantification of three independent experiments; values on the left represent fold increase of transcripts in cells treated with doxycycline versus untreated cells; GAPDH mRNA, which was found to be relatively insensitive to hDIS3 mutations in northern-blots (refer to (A), as an example), was utilized for normalization purposes; abundance of all analyzed PROMPTs was significantly higher in cells producing hDIS3 variants with D487N and R780K substitutions, when compared to the wild-type control; this effect was not seen for mRNAs synthesized under the control of respective promoters located downstream of three of the analyzed PROMPT regions or for unrelated mitochondrial transcript—ATP6/8, which was used as a negative control.

First, low-resolution northern-blot analysis was applied to selected transcripts synthesized by different RNA polymerases. Above all, massive accumulation of unprocessed 5.8S ribosomal RNA precursors (RNA polymerase I transcripts) was noticed following doxycycline-mediated induction in cell lines bearing mutated hDIS3 variants (but not wild-type counterpart) (FIG. 6A). In the case of RNA polymerase II transcripts, while GAPDH polyA$^+$ mRNA levels, used for normalization, remained constant in all cell lines (irrespective of induction), clear increase of histone H2A polyA$^-$ mRNA amounts in cells expressing hDIS3$^{D487N}$, hDIS3$^{G766R}$ and hDIS3$^{R780K}$ mutant proteins was observed (FIG. 6A). Concerning RNA polymerase III transcripts, although expression of hDIS3 mutants did not seem to have significant impact on RNase MRP RNA (FIG. 6A), the levels of two other representative RNA species synthesized by this enzyme, namely RNase P RNA and 7SL RNA, were increased, particularly in cell lines producing hDIS3$^{D487N}$ and hDIS3$^{R780K}$ (variants (FIG. 6A). The phenotype observed for 7SL RNA was also confirmed by high-resolution northern blot analysis (FIG. 6D).

Figure 6B:
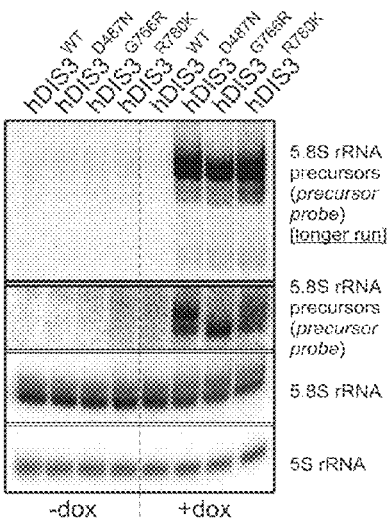
Figure 7A:
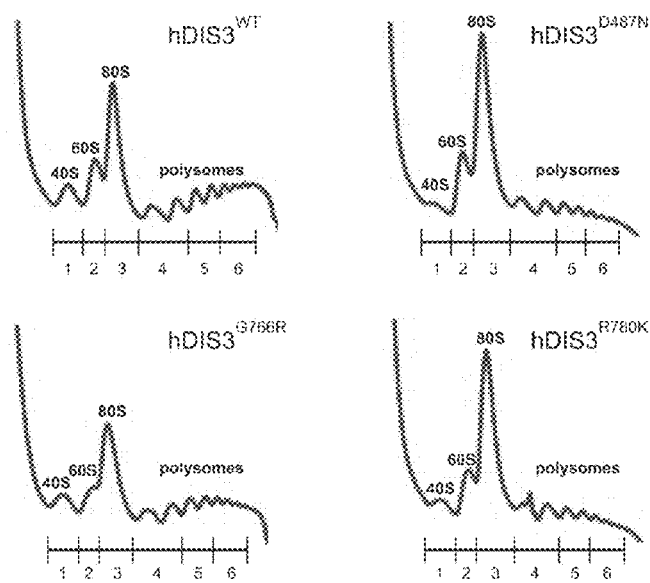
FIGS. 7A-B. Analysis of polysome profiles of model cell lines. (A) Native cytoplasmic extracts were prepared from stable cell lines subjected to induction of expression of exogenous hDIS3 variants and separated by centrifugation in sucrose gradients; graphs show distribution of absorbance at 254 nm from the top (left) to the bottom (right) of the gradients; peaks corresponding to individual ribosomal subunits (40S and 60S), monosomes (80S) and polysomes are indicated; 6 fractions were collected from each gradient (numbered 1-6)—their borders are marked with vertical lines; polysome profiles do not seem to vary between cell lines producing different variants of hDIS3. (B) Northern-blot analysis of RNA samples prepared from fractions collected in (A), performed using probes specific to 5.8S rRNA 3'-extended precursors and to the mature 5.8S and 5S rRNA molecules (controls); 5.8S rRNA precursors, which accumulate significantly in cell lines producing mutated hDIS3 variants, were present in polysomes.
Figure 7B:
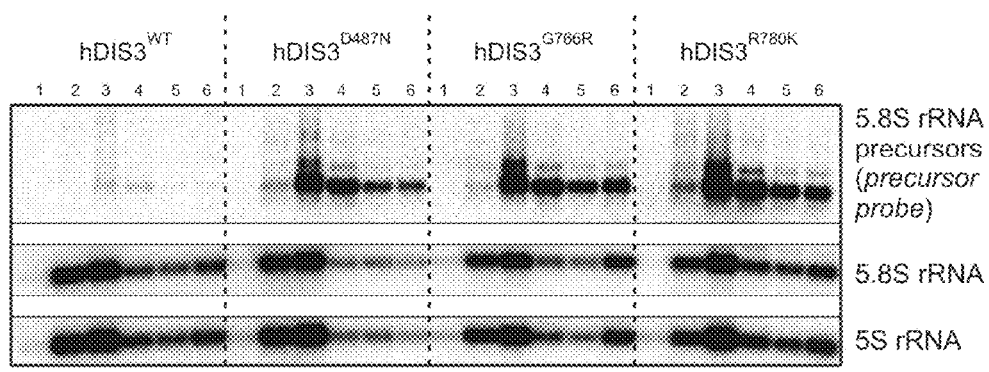
Figure 8A:
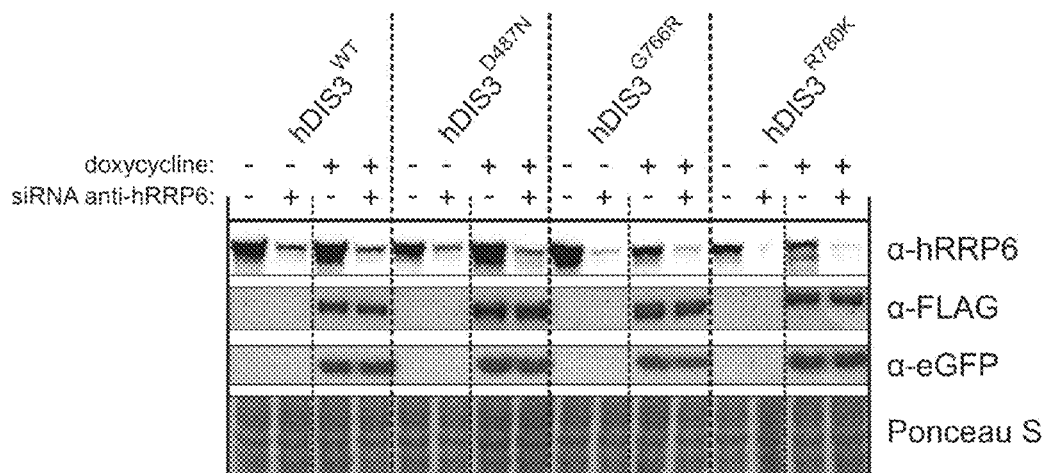
FIGS. 8A-B. siRNA-mediated silencing of hRRP6 expression does not have a significant synergistic effect on accumulation of 5.8S rRNA precursors with production of mutated hDIS3 variants. (A) Western-blot analysis was performed for protein samples from model cell lines: non-induced or treated with doxycycline (doxycycline: "−" or "+", respectively), which were transfected with either siRNA against hRRP6 (anti-hRRP6: "+") or with control, unrelated siRNA (anti-hRRP6: "−"); following transfer of proteins separated in SDS-PAGE onto nitrocellulose membrane, it was probed with antibodies specific to hRRP6, FLAG epitope or eGFP staining of the membrane with Ponceau S Red was employed as a loading control. (B) Northern-blot analysis of 5.8S rRNA precursors; total RNA was isolated from the same cell lines as in (A), separated in denaturing agarose gel and transferred onto nylon membrane, which was then hybridized with probes recognizing 5.8S rRNA 3'-extended precursors (top) or mature molecules (bottom).
Figure 8B:
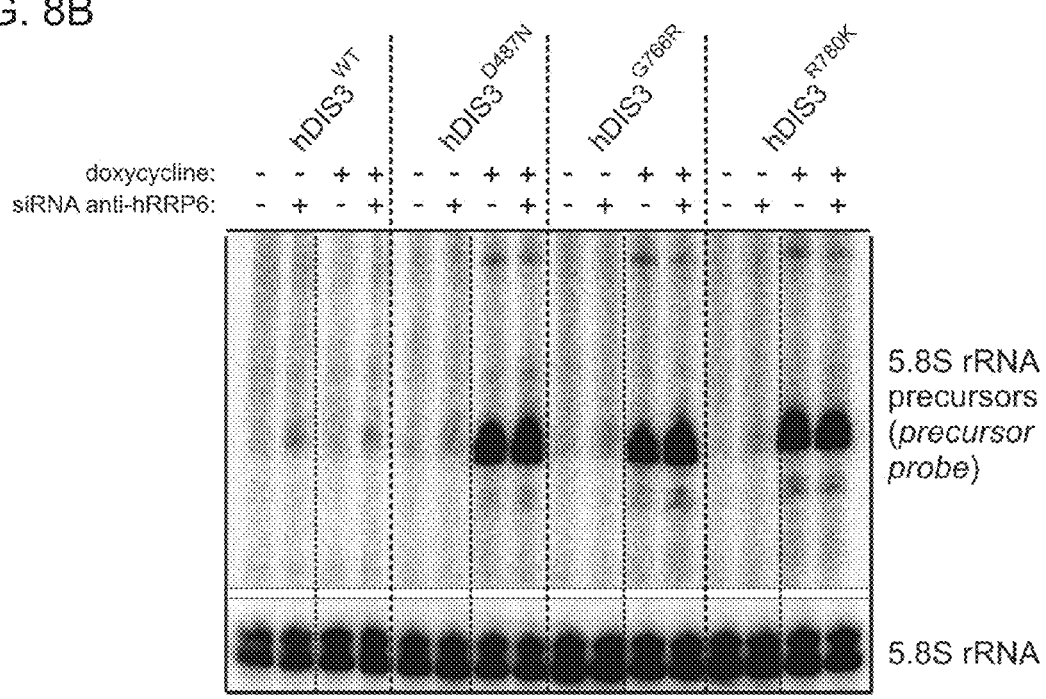

As the degree of accumulation was the strongest for 5.8S rRNA precursors, it was analyzed in more detail by high-resolution northern blots, using 5S rRNA as loading control (FIG. 6B). Generally, it was confirmed that the levels of these species were elevated exclusively upon induction carried out in cell lines with hDIS3 mutations (FIG. 6B). However, owing to this experiment, it was possible to additionally demonstrate that: 1) patterns of observed precursors differed between each of individual mutants and 2) accumulating precursors were more similar between hDIS3 D487N and R780K mutants than those detected in cell line expressing hDIS3$^{G766R}$ protein (FIG. 6B). Furthermore, it was shown that in spite of apparently significant processing defect, levels of mature 5.8S rRNA were not markedly reduced (FIG. 6B). Consequently, neither ribosome biogenesis nor polysome formation seemed to be significantly disturbed (FIG. 7A). Interestingly, observed 5.8S rRNA precursors were incorporated into polysomes (FIG. 7B). It is also worth noting that their accumulation was not further increased by siRNA-mediated silencing of hRRP6 expression (FIG. 8).

Figure 6C:
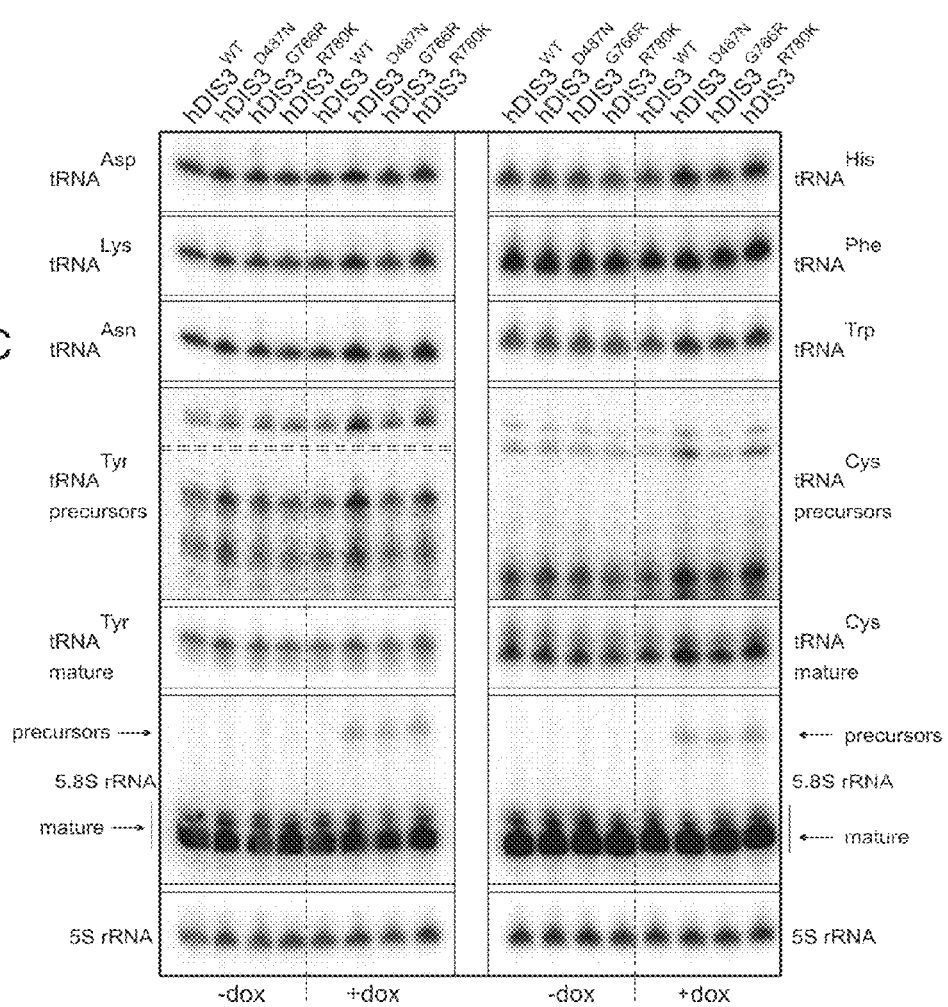

Two recent publications underscored importance of exosome and catalytic Dis3 activities in particular, in the global degradation of non-coding RNAs in yeast (Schneider et al. 2012; Gudipati et al. 2012). In both high-throughput analyses, accumulation of tRNAs and their precursors was reported as one of the most prominent phenotypes resulting from Dis3 inactivation. This, together with the finding that levels of some other RNA polymerase III transcripts are increased in cells producing mutant variants of hDIS3 (FIG. 6A), prompted to more carefully analyze the influence of hDIS3 mutations on selected tRNA molecules. It was noted that almost all examined mature tRNA (except tRNA$^{Tyr}$ and tRNA$^{Phe}$), as well as precursors of tRNA$^{Tyr}$ and tRNA$^{Cys}$, accumulate in cell lines bearing exogenous hDIS3 versions with D487N or R780K mutations following doxycycline treatment (FIG. 6C). Although the effect was not so much pronounced as for 5.8S rRNA precursors (FIG. 6A-C), it was extremely reproducible. It is again worth emphasizing that amino acid substitutions in positions 487 and 780 exerted stronger molecular phenotype than G766R change (FIG. 6C).

Figure 6D:
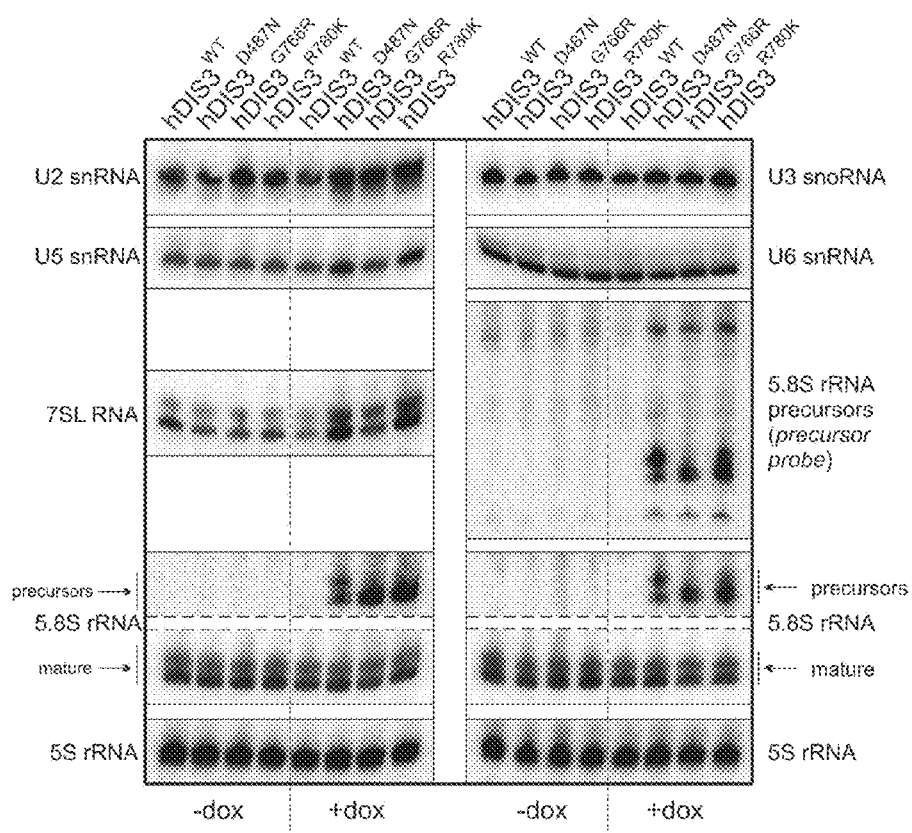
Figure 6E:
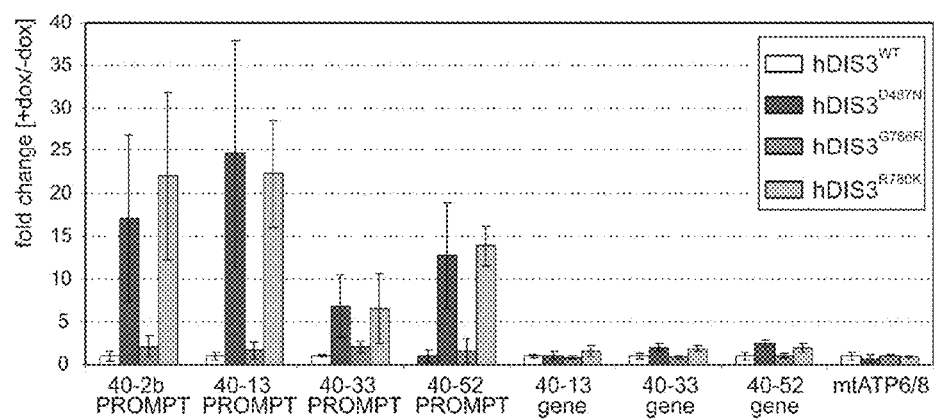

The impact of hDIS3 mutations on the accumulation of U3 snoRNA and three different snRNAs was also investigated, however only for U5 snRNA the phenotype resembling the one observed previously in the case of tRNAs was noticed (FIG. 6D). On the contrary, for all analyzed PROMPTs—unstable transcripts, which were previously shown to accumulate in cells subjected to siRNA-mediated depletion of human exosome subunits (Preker et al. 2008; Tomecki et al. 2010b; Lubas et al. 2011)—it was found that their levels were increased in all cell lines producing mutated hDIS3 variants (FIG. 6E). In agreement with other analyses, accumulation of PROMPTs was far more pronounced in cells bearing hDIS3 D487N or R780K mutation than in the case of G766R substitution (FIG. 6E). Additionally, corresponding protein-coding transcripts synthesized from promoters localized downstream 3 out of 4 PROMPTs were analyzed and it demonstrated that they were not affected by hDIS3 mutations, similarly to entirely unrelated mitochondrial transcript—ATP6/8 (FIG. 6E).

In summary, hDIS3 mutations in the model cell lines resulted in accumulation of majority of analyzed exosome substrates, including 5.8S processing intermediates, tRNAs, RNA polymerase III transcripts and PROMPTs. Although the degree of accumulation was variable between different exosome targets, it was clearly observed that in most of the cases it was more significant in the cells producing hDIS3 $^{D487N}$ and hDIS3R$^{780K}$ than hDIS3$^{G766R}$ variant.

Example IV

MM-Associated hDIS3 Mutations Lead to Growth Inhibition of Human Model Cell Lines.
Cell Growth Analyses.

Stable inducible HEK293 Flp-In T-REx cell lines obtained in Example III were grown as described in Example III until reaching 90% confluence. In the 48-hours induction mode 2×10$^5$ cells were plated directly on plates in a medium either lacking or containing doxycycline and grown for another 48 hours. In the 48-hours +48-hours induction mode the cells were first re-plated onto new plates, in a medium either lacking or containing doxycycline, at 40% confluence; 48 hours later, 2×10$^5$ cells were plated on plates in the respective medium and grown for another 48 hours. Cell growth and eGFP fluorescence were analyzed using Olympus IX81 microscope (Olympus)

"Cell competition assay" was carried out by mixing equal amounts (5×10$^5$) of "empty" HEK293 Flp-In T-REx and established stable cell line, plating them on plates, followed by induction of expression with doxycycline. Eventually, microscopy observations were performed as described above.

Assays on metabolic activity of the cell lines were performed as follows. 5000 of the cells were plated in triplicates (for each cell line, condition and time of measurement) on 96-well plates. Cells were either maintained in a medium lacking doxycycline or subjected to treatment with the inducer. 24 hours, 72 hours or 120 hours following induction, 10 µl of AlamarBlue® (Invitrogen) was added to the cultures. Amounts of the reduced reagent were quantified after 120 minutes using DTX880 Multimode Detector (Beckman Coulter). During the growth of cells for RNA isolation, it was noticed that cell lines expressing hDIS3 variants with D487N or R780K substitutions grew slightly worse following 48-hour-long period of doxycycline-mediated induction than two other cell lines. To be absolutely sure whether hDIS3 mutations have impact on cell physiology, additional growth analysis for established cell lines was performed through the observation of the uninduced cells and their counterparts subjected to a prolonged induction (that is: 48 hours, followed by passage of the cells into the fresh medium containing doxycycline and another 48 hours of culture) using a fluorescence microscope. While all of them grew normally and comparably in a medium lacking doxycycline (data not shown), upon longer-term sh-miRNA-mediated repression of endogenous hDIS3 and simultaneous expression of sh-miRNA-insensitive exogenous hDIS3 variants, the four cell lines behaved differently (FIG. 9A). hDIS3$^{WT}$ produced from the construct integrated into cells' genome clearly complemented decreased level of endogenous hDIS3 expression, so that the cell growth was undisturbed. On the contrary, in the case of cell lines expressing hDIS3$^{D487N}$ and hDIS3$^{R780K}$ variants, growth inhibition was observed (FIG. 9A), while G766R mutation in hDIS3 exerted only moderate effect on the cell growth (FIG. 9A). These results were in line both with biochemical data, which suggested that G766R leads to milder inhibition of degradation (especially when using single-stranded substrates) when compared with D487N or R780K amino acid changes (see FIG. 1C and FIG. 2) and with the findings that the two D487N or R780K mutations result in more pronounced accumulation of various RNA molecules than in the case of G766R mutation (FIG. 6).

It is worth noting that virtually all cells in the field of view displayed eGFP fluorescence (FIG. 9A), so it can be assumed that these cells expressed also the second insert, encoding hDIS3-FLAG fusion. Ubiquitous eGFP expression was also confirmed by FACS analysis (data not shown). Moreover, it was possible to take advantage of eGFP expression in the model cell lines in another simple growth test, which was dubbed as a "cell competition assay". In this experiment equal number of each of the four stable cell lines and control HEK293 Flp-In T-REx cells (devoid of eGFP) was mixed and, following induction of expression, such "hybrid" cell lines were observed under a fluorescence microscope. In the case of T-REx +hDIS3$^{WT}$ and T-REx +hDIS3$^{G766R}$ mixtures the 1:1 ratio of fluorescent to non-fluorescent cells was maintained, meaning that the established cell lines do not grow significantly slower than the control line (FIG. 9B). In contrast, the number of fluorescent cells for T-REx+hDIS3$^{D487N}$ and T-REx+hDIS3$^{R780K}$ mixtures was much lower comparing with the cells lacking fluorescence (FIG. 9B), indicating that the "empty" HEK293 Flp-In T-REx cells outcompeted cell lines stably expressing these two particular hDIS3 variants. This suggests that they are defective in complementing the decreased levels of endogenous wild-type hDIS3 protein, which is reflected by increased mortality of the cells.

More detailed comparative analysis of cell viability was performed for the model cell lines using AlamarBlue® reagent. The assay basing on this compound relies on the fact that it is reduced by metabolically-active cells upon addition to cell culture, which changes its spectral properties. The amount of reduced form of the compound reflects the metabolic activity of the cells and—indirectly—their viability (resultant of both proliferation and mortality). Therefore colorimetric measurements of the amounts of reduced AlamarBlue® in cell lines with transgenes coding for different hDIS3 variants were carried out, the cells being either uninduced or subjected to doxycycline treatment. It was noticed that the results were strikingly similar for all cell lines, provided that the co-expression of sh-miRNA and exogenous hDIS3 was not induced (FIG. 9C). On the other hand, a remarkably different behavior of the model lines was observed, following doxycycline-mediated induction: metabolic activity of the cell line expressing exogenous hDIS3$^{WT}$ was virtually unchanged comparing with the lack of induction, whereas it was reduced to different extent in the remaining three cell lines, producing mutated hDIS3 versions (FIG. 9C). In agreement with preliminary growth tests, the phenotype was strongest for hDIS3$^{D487N}$ mutant and weakest in the case of hDIS3$^{G766R}$ variant (FIG. 9C).

Summing up, with the use of the experimental system it was demonstrated that hDIS3 D487N catalytic mutation, as well as G766R and R780K substitutions found in multiple myeloma patients, lead to the enhanced mortality and inhibition of metabolic activity of human cells. Growth defects might be an ultimate result of aberrations in RNA metabolism.

Example V

MM-Associated Mutations in hDIS3 RNB Domain are Synthetically Lethal with PIN Domain Catalytic Mutation in Human Cells.

Oligonucleotides, Plasmids and Cloning.

pMM11, pMM12, PMM13, pMM14 constructs were generated by site-directed mutagenesis using D3PINF (AGGAATAACCGGGCGATTCGAGTAGCAGCAAAATGGTACAATG) (SEQ ID NO: 97)- D3PINR (TCGAATCGCCCGGTTATTCCTGTCATTAGCATTT TCTCCCTG) (SEQ ID NO: 98)-oligonucleotide pair and pMM7, pMM8, pMM9, pMM10 plasmids constructed in example III as respective templates. These construct were generated in order to examine influence of mutation occurring in PIN and RNB domains simultaneously.

Cell Culture, Generation of Stable Cell Lines and Cell Growth Analyses.

Cell lines were obtained as described in Example III but with the use of pMM11, pMM12, pMM13, pMM14 constructs. Cells were grown in conditions described in Example III. Cell growth was analyzed as described in Example IV.

RNA Isolation and Northern-Blot Analysis.

RNA isolation and high-resolution northern-blots were performed as described in Example III.

Reverse Transcription and Quantitative PCR.

Reverse transcription and quantitative PCR were performed as described in Example III.

Next, it was important to evaluate whether there might be any effect of hDIS3 PIN domain endonuclease activity in the background of different hDIS3 RNB domain mutations. To this end, analogous stable cell lines were constructed, bearing additional mutation in the catalytic site of PIN domain—D146N—which was previously shown to abolish hDIS3 endonucleolytic activity in the in vitro assays. Cell growth assays performed as described in Example IV, revealed that the growth of cell lines expressing different hDIS3 versions with D146N mutation was rather unaffected in the absence of doxycycline (FIG. 10A). On the other hand, only cell line expressing hDIS3$^{D146N}$ single mutant grew relatively normally and comparably to its counterpart producing hDIS3$^{WT}$ upon induction, indicating that endonuclease activity alone has little impact on cell physiology (FIG. 10A). In contrast, combination of PIN domain catalytic mutation with any the amino acid substitutions within RNB domain (D487N, G766R or R780K) resulted in a dramatic growth defect (FIG. 10A). A synergistic effect of inactivation of both nucleolytic activities of hDIS3 was most obvious in the case of cells expressing hDIS3$^{D146N\ G766R}$ double mutant, taking into account that the respective cell line producing hDIS3 with G766R mutation alone displayed very mild growth inhibition comparing to the WT control (FIG. 10A). Importantly, an assay performed using AlamarBlue® reagent disclosed that the metabolic activity of the cells bearing mutations within RNB domain is also additionally reduced upon accompanying inactivation of PIN domain endonuclease (FIG. 10B).

Figure 10D:
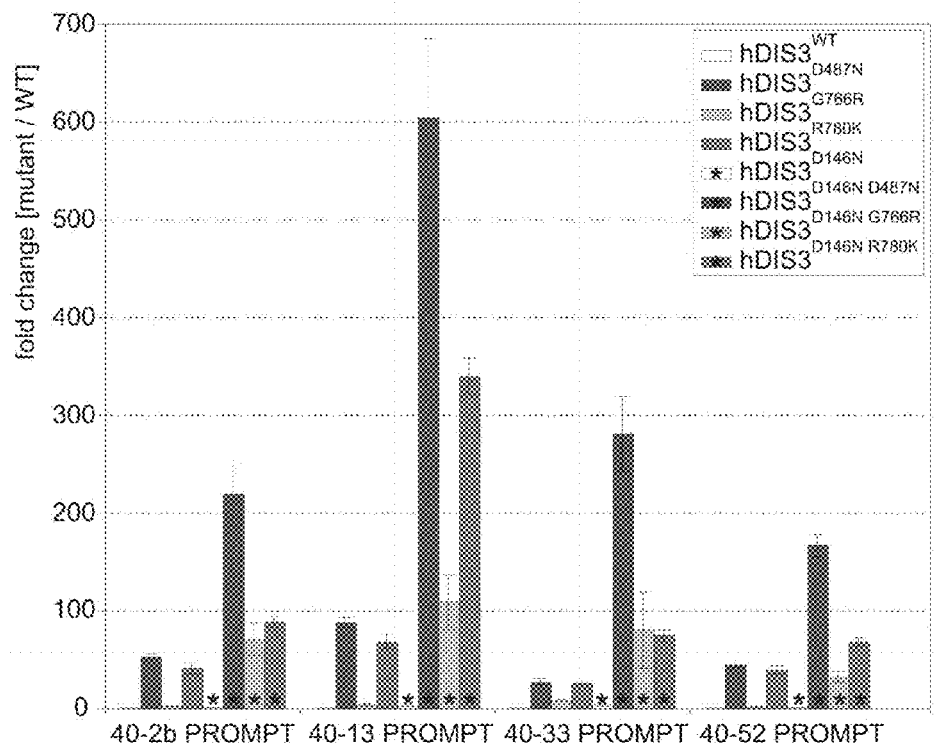
Figure 10E:
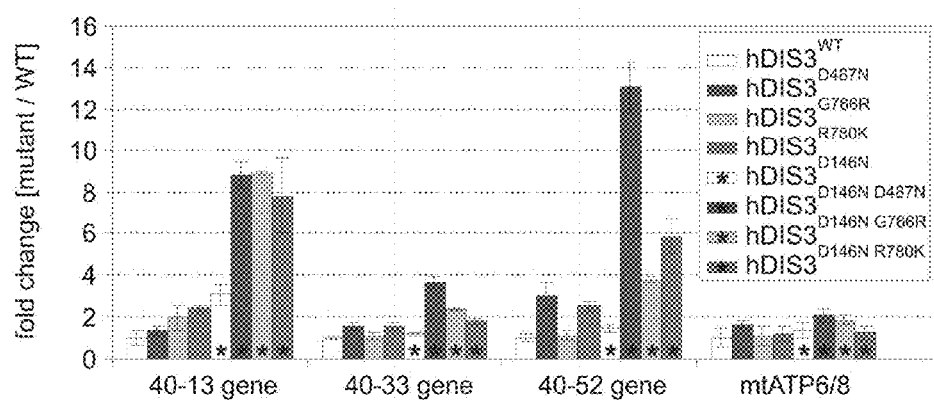

Then, an analysis of molecular phenotypes resulting from combination of MM-associated hDIS3 mutations within RNB domain with disruption of PIN domain endonucleolytic activity was carried out by comparing the cells to respective single mutants. As shown in the FIG. 10C, inactivation of PIN domain catalytic activity alone did not lead to accumulation of 5.8S rRNA precursors. Interestingly, no synergistic effect of D146N substitution in the background of RNB domain mutations was observed, as the levels of precursor molecules were not further elevated in cell lines expressing hDIS3$^{D146N\ D87N}$, hDIS3$^{D146N\ G766R}$ and hDIS3$^{D146N\ R780K}$ comparing to the cell lines producing respective hDIS3 versions with intact PIN domain active centre (FIG. 10C). This indicates that such 3'-extended 5.8S rRNA species are normally degraded mainly by hDIS3 exoribonucleolytic activity. Similarly, no additional effect of D146N mutation on RNA polymerase III transcripts or U5 snRNA was detected, i.e. the RNA species that was found to be accumulated in cell lines producing hDIS3 variants with mutations within RNB domain (data not shown). On the contrary, the results clearly demonstrate that while the levels of different PROMPTs are comparable between cell lines producing either hDIS3 with D146N substitution or its WT counterpart, the cell lines expressing hDIS3$^{D146N\ D487N5}$ hDIS3$^{D146N\ G766R}$ and hDIS3$^{D146N\ R780K}$ double mutants accumulate much higher amounts of PROMPTs than respective single mutants (FIG. 10D). This strongly suggests that such non-coding RNA molecules are degraded by cooperative action of both nucleolytic activities of hDIS3. Intriguingly, a highly similar trend for protein-coding transcripts corresponding to 3 out of 4 tested PROMPTs was noticed (but not for mitochondrial ATP6/8 mRNA, which was not expected to be affected by the exosome dysfunction), although the fold differences between double and single mutants were not so dramatic as in the case of PROMPTs (FIG. 10E).

Example VI 2-hydroxy-(4H)-isoquinoline-1,3-dione Inhibits the Endonucleolytic Activity of the Isolated PIN domain of hDIS3 in vitro.
2-hydroxy-(4H)-isoquinoline-1,3-dione Synthesis.

2-hydroxy-(4H)-isoquinoline-1,3-dione synthesis was performed according to method described in Bioorganic & Medicinal Chemistry vol. 20 ((2012) 467-479).

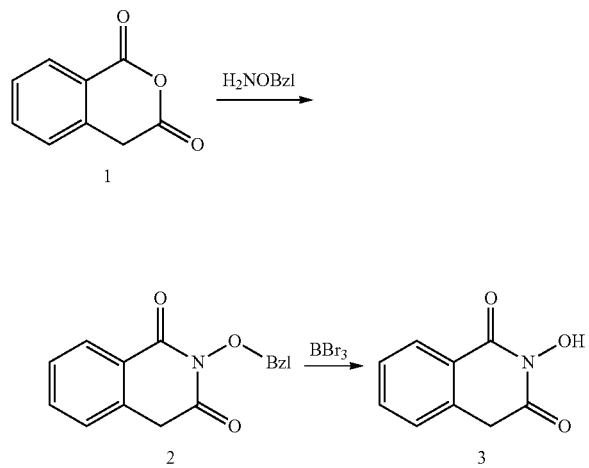

Mixture of homophtalic anhydride 1 (0.5 g; 3.08 mmol), benzylhydroxylamine hydrochloride (0.59 g; 3.7 mmol) and triethylamine (0.5 ml; 3.7 mmol) in toluene was heated on heating mantle with Dean-Stark apparatus for 4 h. Substrate is still visible on LCMS, adding amines and heating nothing change so reaction was stopped. White solid was removed by filtration.

The filtrate was concentrated to dryness, dissolved in DCM and purified by column chromatography AcOEt/hexane ⅛. Crystallization from Et$_2$O gave 0.39 g (48%) of 2 as white solid. $^1$H NMR (CDCl$_3$, 200 MHz):

δ8.23 (d, 2H, J=9Hz); 7.66-7.26 (m, 8H); 5.15 (s, 2H); 4.15 (s, 2H).

To a solution of 2 (0.36 g; 1.34 mmol) in DCM, BBr$_3$ (0.25 ml; 2.66 mmol) was added in one portion and reaction was stirred for 1 h at rt. Then reaction was carefully quenched with water. After 15 min yellow solid was removed by filtration. The filtrate was extracted with DCM, dried over MgSO$_4$ and concentrated. Crystallization from Et$_2$O gave 0.088 g of 3 as beige solid. $^1$H NMR (DMSO, 200 MHz): δ10.39 (brs, 1H); 8.01 (d, 1H, J=8Hz); 7.68-7.36 (m, 3H); 4.25 (s, 2H).

Activity Assay.

Recombinant protein was obtained with the method described in Example I. Substrate for in vitro biochemical assay was a 5' fluoresceine-labeled ss17-(A)$_{34}$, which was prepared similarly to substrates described in Example I. The activity assay was performed as described in Example I in the presence or absence of 2-hydroxy-(4H)-isoquinoline-1, 3-dione.

Figure 11A:
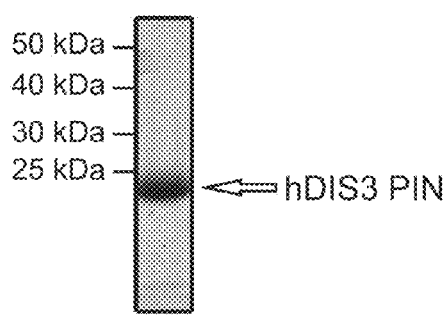
FIGS. 11A-B. 2-hydroxy-(4H)-isoquinoline-1,3-dione (ACILAHYL) inhibits the endonucleolytic activity of isolated PIN domain of hDIS3. A) SDS-PAGE analysis of the recombinant hDIS3 PIN domain; B) Activity assay. 5' fluoresceine-labeled ss17-(A)$_{34}$ substrate was incubated in a buffer containing 1 mM manganese with recombinant hDIS3 PIN domain in the presence or absence of 2-hydroxy-(4H)-isoquinoline-1,3-dione. A control reaction was also performed, which contained the inhibitor but lacked any added protein. Reactions were terminated at the indicated time points, followed by denaturing PAGE and fluorimaging.
Figure 11B:
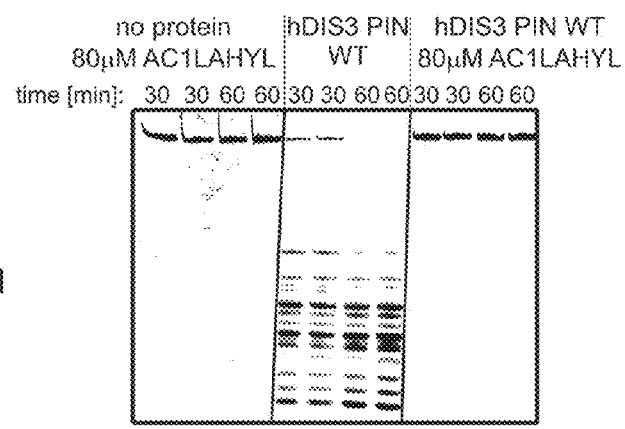

After establishing that inactivation of the hDIS3 PIN domain is synthetically lethal with MM associated mutations in the RNB domain, a search for for putative inhibitors was conducted. 2-hydroxy-(4H)-isoquinoline-1,3-dione, which is a well-known inhibitor of RNAse H (Hang et al. 2004) was synthesized. In order to conduct an activity assay for human DIS3 PIN domain endonucleolytic activity, a recombinant version of isolated PIN domain (FIG. 11A) was produced. Next, an activity assay was performed in the presence or absence of the putative inhibitor (FIG. 11B). 2-hydroxy-(4H)-isoquinoline-1,3-dione efficiently inhibited the endonucleolytic activity of human DIS3 PIN domain at 80 μM concentration.

Example VII 2-hydroxy-(4H)-isoquinoline-1,3-dione Specifically Inhibits Growth of Yeast Strains Harboring mutations in yeast DIS3 gene corresponding to those found in MM patients.

Yeast Growth Assays.

Yeast strains harboring G833R or R847K mutations, obtained in Example II were used for growth assays. Serial dilutions of indicated yeast strains were spotted on YPD plates and YPD plates with 2-hydroxy-(4H)-isoquinoline-1, 3-dione (at 1 mM concentration) and incubated at 30° C. for 60 hours.

Figure 12:
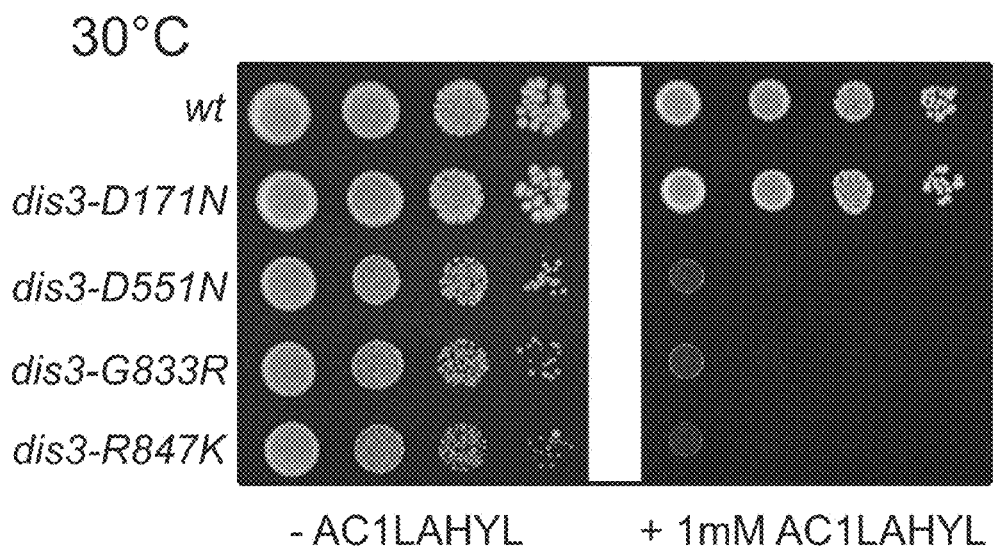
FIG. 12. 2-hydroxy-(4H)-isoquinoline-1,3-dione (AClLAHYL), an inhibitor of DIS3 PIN domain activity, leads to complete growth inhibition of yeast harboring G833R and R847K mutations but not WT yeast. Serial dilutions of indicated yeast strains were spotted on YPD plates and YPD plates with 2-hydroxy-(4H)-isoquinoline-1,3-dione (at 1 mM concentration) and incubated at 30° C. for 60 hours.

Knowing that 2-hydroxy-(4H)-isoquinoline-1,3-dione inhibits DIS3 PIN domain activity, an in vivo analysis was performed using yeast strains harboring G833R or R847K mutations, obtained in Example II (FIG. 12). 2-hydroxy-(4H)-isoquinoline-1,3-dione leads to complete growth inhibition of yeast harboring G833R and R847K mutations but not WT yeast. This indicates that inhibitors of hDIS3 PIN domain activity indeed specifically inhibit growth of cells with DIS3 MM-associated mutations.

In the below Table 6 there are gathered hDIS3 RNB domain mutations (the position of which relates to SEQ ID NO: 1) and theirs equivalents in yeasts or cell lines.

TABLE 6

| Recombinant hDIS3 variant | Changes in RNA substrate degradation in comparison to hDIS3$^{WT}$ | The obtained corresponding mutation in S. cerevisiae and phenotypes observed in the S. cerevisiae mutant strain | The obtained corresponding human cell line (derivative of HEK293 Flp-In T-REx) and phenotypes observed in the human cell line |
|---|---|---|---|
| hDIS3$^{S477R}$ | ssRNA - changes in the pattern of final degradation products dsRNA - degradation inhibited by structured regions | — | — |
| hDIS3$^{G766R}$ | ssRNA - changes in the pattern of final degradation products/ loss of processivity dsRNA - degradation inhibited by structured regions | dis3-G833R severely impaired growth strong accumulation of the exosome RNA substrates | hDIS3$^{G766R}$ moderately reduced growth and metabolic activity strong accumulation of pre-5.8S rRNA weak accumulation of other exosome substrates |
| hDIS3$^{R780K}$ | ssRNA - severely impaired degradation dsRNA - degradation inhibited by structured regions | dis3-R847K severely impaired growth strong accumulation of the exosome RNA substrates | hDIS3$^{R780K}$ severely reduced growth and metabolic activity strong accumulation of pre-5.8S rRNA strong accumulation of other exosome substrates |
| hDIS3$^{V504G}$ | ssRNA, dsRNA - slower degradation | dis3-V568G thermosensitivity weak accumulation of the exosome substrates | — |
| hDIS3$^{A524P}$ | N/A | dis3-A588P thermosensitivity weak accumulation of the exosome substrates | — |
| hDIS3$^{I845V}$ | none | — | — |
| hDIS3$^{D487N}$ | ssRNA, dsRNA - lack of degradation | dis3-D551N severely impaired growth strong accumulation of the exosome RNA substrates | hDIS3$^{D487N}$ everely reduced growth and metabolic activity strong accumulation of pre-5.8S rRNA strong accumulation of other exosome substrates |

By the above Examples it has been confirmed that in vivo that application of the compound which inhibits hDIS3 PIN domain activity lead to growth inhibition of the cells having disturbances in hDIS3 activity, especially mutations in hRNB Dis3 domain. These confirms that the compounds which are inhibitors of hDIS3 PIN domain are also effective therapeutic agents for treatment of cancers in which there are mutations in hDIS3 RNB domain. Cancers in which there are mutations in hDIS3 RNB domain can be selected form multiple myeloma, medulloblastoma and acute myeloid leukaemia. The mutations in the RNB domain of the hDIS3 are preferably selected from mutation S477R, G766R, R780K, V504G, A524P, I845V with relation to SEQ ID NO: 1.

REFERENCES CITED IN THE DESCRIPTION:

1. Allmang C et al. 1999. *EMBO J* 18: 5399-5410.
2. Allmang C et al. 2000. *Nucleic Acids Res* 28: 1684-1691.
3. Assenholt J et al. 2008. *RNA* 14: 2305-2313.
4. Barber L J et al. 2013. *J Pathol* 229: 422-429.
5. Bonneau F et al. 2009. *Cell* 139: 547-559.
6. Bryant H E et al. 2005. *Nature* 434: 913-917.
7. Camblong J et al. 2007. *Cell* 131: 706-717.
8. Camps J et al. 2013. *Cancer Res* 73: 2003-2013.
9. Chapman M A et al. 2011. *Nature* 471: 467-472.
10. Ding L et al. 2012. *Nature* 481: 506-510.
11. Drazkowska K et al. 2013. *Nucleic Acids Res* 41: 3845-3858.
12. Dziembowski A et al. 2007. *Nat Struct Mol Biol* 14: 15-22.
13. Farmer H et al. 2005. *Nature* 434: 917-921.
14. Gherzi R et al. 2004. *Mol Cell* 14: 571-583.
15. Gudipati R K et al. 2012. *Mol Cell* 48: 409-421.
16. Hang J Q et al. 2004. *Biochem Biophys Res Commun* 317: 321-329.
17. Isken O & Maquat L E. 2007. *Genes Dev* 21: 1833-1856.
18. Kadaba S et al. 2004. *Genes Dev* 18: 1227-1240.
19. Laubach J et al. 2011. *Annu Rev Med* 62: 249-264.
20. Lebreton A & Seraphin B. 2008. *Biochim Biophys Acta* 1779: 558-565.
21. Lebreton A et al. 2010. *Nature* 456: 993-996.
22. Liang L et al. 2007. *Cancer Invest* 25: 427-434.
23. Lim J et al. 1997. *Cancer Res* 57: 921-925.
24. Liu Q et al. 2006. *Cell* 127: 1223-1237.
25. Lubas M et al. 2011. *Mol Cell* 43: 624-637.
26. Lykke-Andersen S et al. 2011. *RNA Biol* 8: 61-66.
27. Malet H et al. 2010. *EMBO Rep* 11: 936-942.
28. Mitchell P et al. 1997. *Cell* 91: 457-466.
29. Mukherjee D et al. 2002. *EMBO J* 21: 165-174.
30. Orban T I & Izaurralde E. 2005. *RNA* 11: 459-469.
31. Parker R. 2012. *Genetics* 191: 671-702.

32. Parsons D W et al. 2011. *Science* 331: 435-439.
33. Porcelli L et al. 2012. *Curr Med Chem* 19: 3858-3873.
34. Preker Pet al. 2008. *Science* 322: 1851-1854.
35. Rose A E et al. 2011. *Cancer Res* 71: 2561-2571.
36. Sammarco MC & Grabczyk E. 2005. *Anal Biochem* 346: 210-216.
37. Schaeffer D et al. 2009. *Nat Struct Mol Biol* 16: 56-62.
38. Schaeffer D et al. 2012. *Nucleic Acids Res* 40: 9298-9307.
39. Schmid M & Jensen T H. 2008. *Trends Biochem Sci* 33: 501-510.
40. Schneider C et al. 2009. *Nucleic Acids Res* 37: 1127-1140.
41. Schneider C et al. 2012. *Mol Cell* 48: 422-433.
42. Staals R H et al. *EMBO J* 29: 2358-2367.
43. Tomecki R et al. 2010a. Chembiochem 11: 938-945.
44. Tomecki Ret al. *EMBO J* 29: 2342-2357.
45. Walker B A et al. 2012. *Blood* 120: 1077-1086.
46. Wang X et al. 2008. RNA 14: 107-116.
47. Wasmuth E V & Lima C D. 2012. *Mol Cell* 48: 133-144.
48. Wyers F et al. 2005. *Cell* 121: 725-737.

```
Sequence Listing Free Text (the sequences Seq Id
No 3-98 are given within the description):
SEQ ID NO: 1 is wt human Dis3 amino acid sequence
MLKSKTFLKKTRAGGVMKIVREHYLRDDIGCGAPGCAACGGAHEGPALEP

QPQDPASSVCPQPHYLLPDTNVLLHQIDVLEDPAIRNVIVLQTVLQEVRN

RSAPVYKRIRDVTNNQEKHFYTFTNEHHRETYVEQEQGENANDRNDRAIR

VAAKWYNEHLKKMSADNQLQVIFITNDRRNKEKAIEEGIPAFTCEEYVKS

LTANPELIDRLACLSEEGNEIESGKIIFSEHLPLSKLQQGIKSGTYLQGT

FRASRENYLEATVWIHGDSEENKEIILQGLKHLNRAVHEDIVAVELLPKS

QWVAPSSVVLHDEGQNEEDVEKEEETERMLKTAVSEKMLKPTGRVVGIIK

RNWRPYCGMLSKSDIKESRRHLFTPADKRIPRIRIETRQASTLEGRRIIV

AIDGWPRNSRYPNGHFVRNLGDVGEKETETEVLLLEHDVPHQPFSQAVLS

FLPKMPWSITEKDMKNREDLRHLCICSVDPPGCTDIDDALHCRELENGNL

EVGVHIADVSHFIRPGNALDQESARRGTTVYLCEKRIDMVPELLSSNLCS

LKCDVDRLAFSCIWEMNHNAEILKTKFTKSVINSKASLTYAEAQLRIDSA

NMNDDITTSLRGLNKLAKILKKRRIEKGALTLSSPEVRFHMDSETHDPID

LQTKELRETNSMVEEFMLLANISVAKKIHEEFSEHALLRKHPAPPPSNYE

ILVKAARSRNLEIKTDTAKSLAESLDQAESPTFPYLNTLLRILATRCMMQ

AVYFCSGMDNDFHHYGLASPIYTHFTSPIRRYADVIVHRLLAVAIGADCT

YPELTDKHKLADICKNLNFRHKMAQYAQRASVAFHTQLFFKSKGIVSEEA

YILFVRKNAIVVLIPKYGLEGTVFFEEKDKPNPQLIYDDEIPSLKIEDTV

FHVFDKVKVKIMLDSSNLQHQKIRMSLVEPQIPGISIPTDTSNMDLNGPK

KKKMKLGK

SEQ ID NO: 2 is wt Saccharomyces cerevisiae Dis3
amino acid sequence
MSVPAIAPRRKRLADGLSVTQKVFVRSRNGGATKIVREHYLRSDIPCLSR

SCTKCPQIVVPDAQNELPKFILSDSPLELSAPIGKHYVVLDTNVVLQAID

LLENPNCFFDVIVPQIVLDEVRNKSYPVYTRLRTLCRDSDDHKRFIVFHN

EFSEHTFVERLPNETINDRNDRAIRKTCQWYSEHLKPYDINVVLVTNDRL

NREAATKEVESNIITKSLVQYIELLPNADDIRDSIPQMDSFDKDLERDTF

SDFTFPEYYSTARVMGGLKNGVLYQGNIQISEYNFLEGSVSLPRFSKPVL

IVGQKNLNRAFNGDQVIVELLPQSEWKAPSSIVLDSEHFDVNDNPDIEAG

DDDDNNESSSNTTVISDKQRRLLAKDAMIAQRSKKIQPTAKVVYIQRRSW

RQYVGQLAPSSVDPQSSSTQNVFVILMDKCLPKVRIRTRRAAELLDKRIV

ISIDSWPTTHKYPLGHFVRDLGTIESAQAETEALLLEHDVEYRPFSKKVL

ECLPAEGHDWKAPTKLDDPEAVSKDPLLTKRKDLRDKLICSIDPPGCVDI

DDALHAKKLPNGNWEVGVHIADVTHFVKPGTALDAEGAARGTSVYLVDKR

IDMLPMLLGTDLCSLKPYVDRFAFSVIWELDDSANIVNVNFMKSVIRSRE

AFSYEQAQLRIDDKTQNDELTMGMRALLKLSVKLKQKRLEAGALNLASPE

VKVHMDSETSDPNEVEIKKLLATNSLVEEFMLLANISVARKIYDAFPQTA

MLRRHAAPPSTNFEILNEMLNTRKNMSISLESSKALADSLDRCVDPEDPY

FNTLVRIMSTRCMMAAQYFYSGAYSYPDFRHYGLAVDIYTHFTSPIRRYC

DVVAHRQLAGAIGYEPLSLTHRDKNKMDMICRNINRKHRNAQFAGRASIE

YYVGQVMRNNESTETGYVIKVFNNGIVVLVPKFGVEGLIRLDNLTEDPNS

AAFDEVEYKLTFVPTNSDKPRDVYVFDKVEVQVRSVMDPITSKRKAELLL

K
```

The invention claimed is:

1. A method for measuring a DIS3 PIN domain endonuclease activity inhibitor that induces a synthetic lethality in a cancer cell having a mutation in a hDIS3 RNB domain, comprising:
   a) constructing a model system comprising DIS3, or a DIS3 fragment, wherein the DIS3 fragment comprises a RNB domain comprising at least 80% identity to a sequence AA 427-843 of SEQ ID NO: 1 or AA 478-910 of SEQ ID NO: 2 and a functional fragment of the PIN domain comprising at least 80% identity to a sequence AA 1-217 of SEQ ID NO: 1 or AA 1-241 of SEQ ID NO: 2, wherein DIS3 or the DIS3 fragment comprises a mutation in the RNB domain, wherein the DIS3 or the DIS3 fragment is an isolated protein or is in a cell line or yeast strain, wherein the mutation is found as occurring in hDIS3 in cancer cells,
   b) contacting the model system obtained in a) with a tested agent wherein the tested agent may inhibit DIS3 PIN domain endonuclease activity, and
   c) measuring the activity of the PIN domain in the presence and absence of the tested agent, wherein this measuring is by assessing DIS3 PIN endoribonuclease activity, cellular growth or cell viability or examining exosome substrates in the presence and absence of the tested agent.

2. The method according to claim 1 wherein the model system is a yeast strain comprising DIS3 with the mutation in the RNB domain.

3. The method according to claim 1, wherein the mutation in hDIS3 gene in cancer cells is at least one mutation occurring in multiple myeloma, medulloblastoma, acute myeloid leukaemia.

4. The method according to claim 1, wherein the mutation in the RNB domain is G766R with relation to SEQ ID NO: 1.

5. The method according to claim 1, wherein the mutation in the RNB domain is S477R with relation to SEQ ID NO: 1.

6. The method according to claim 1, wherein the mutation in the RNB domain is R780K with relation to SEQ ID NO: 1.

7. The method according to claim 1, wherein the mutation in the RNB domain is V504G with relation to SEQ ID NO: 1.

8. The method according to claim 1, wherein the mutation in the RNB domain is A524P with relation to SEQ ID NO: 1.

9. The method according to claim 1, wherein the mutation in the RNB domain is I845V with relation to SEQ ID NO: 1.

10. The method according to claim 1, wherein the mutation in the RNB domain is D487N with relation to SEQ ID NO: 1.

11. The method according to claim 2, wherein the mutation in the RNB domain is G766R with relation to SEQ ID NO: 1.

12. The method according to claim 2, wherein the mutation in the RNB domain is S477R with relation to SEQ ID NO: 1.

13. The method for according to claim 2, wherein the mutation in the RNB domain is R780K with relation to SEQ ID NO: 1.

14. The method according to claim 2, wherein the mutation in the RNB domain is V504G with relation to SEQ ID NO: 1.

15. The method according to claim 2, wherein the mutation in the RNB domain is A524P with relation to SEQ ID NO: 1.

16. The method according to claim 2, wherein the mutation in the RNB domain is I845V with relation to SEQ ID NO: 1.

17. The method according to claim 2, wherein the mutation in the RNB domain is D487N with relation to SEQ ID NO: 1.

18. The method of claim 1 or 3 wherein the tested agent is a chemical or a nucleic acid.

\* \* \* \* \*

SEQUENCE LISTING

```
<160> NUMBER OF SEQ ID NOS: 98

<210> SEQ ID NO 1
<211> LENGTH: 958
<212> TYPE: PRT
<213> ORGANISM: Homo sapiens

<400> SEQUENCE: 1

Met Leu Lys Ser Lys Thr Phe Leu Lys Lys Thr Arg Ala Gly Gly Val
1               5                   10                  15

Met Lys Ile Val Arg Glu His Tyr Leu Arg Asp Asp Ile Gly Cys Gly
            20                  25                  30

Ala Pro Gly Cys Ala Ala Cys Gly Gly Ala His Glu Gly Pro Ala Leu
        35                  40                  45
```

```
Glu Pro Gln Pro Gln Asp Pro Ala Ser Ser Val Cys Pro Gln Pro His
        50                  55                  60

Tyr Leu Leu Pro Asp Thr Asn Val Leu Leu His Gln Ile Asp Val Leu
 65                  70                  75                  80

Glu Asp Pro Ala Ile Arg Asn Val Ile Val Leu Gln Thr Val Leu Gln
                 85                  90                  95

Glu Val Arg Asn Arg Ser Ala Pro Val Tyr Lys Arg Ile Arg Asp Val
            100                 105                 110

Thr Asn Asn Gln Glu Lys His Phe Tyr Thr Phe Thr Asn Glu His His
        115                 120                 125

Arg Glu Thr Tyr Val Glu Gln Glu Gln Gly Glu Asn Ala Asn Asp Arg
    130                 135                 140

Asn Asp Arg Ala Ile Arg Val Ala Ala Lys Trp Tyr Asn Glu His Leu
145                 150                 155                 160

Lys Lys Met Ser Ala Asp Asn Gln Leu Gln Val Ile Phe Ile Thr Asn
                165                 170                 175

Asp Arg Arg Asn Lys Glu Lys Ala Ile Glu Glu Gly Ile Pro Ala Phe
            180                 185                 190

Thr Cys Glu Glu Tyr Val Lys Ser Leu Thr Ala Asn Pro Glu Leu Ile
        195                 200                 205

Asp Arg Leu Ala Cys Leu Ser Glu Gly Asn Glu Ile Glu Ser Gly
    210                 215                 220

Lys Ile Ile Phe Ser Glu His Leu Pro Leu Ser Lys Leu Gln Gln Gly
225                 230                 235                 240

Ile Lys Ser Gly Thr Tyr Leu Gln Gly Thr Phe Arg Ala Ser Arg Glu
                245                 250                 255

Asn Tyr Leu Glu Ala Thr Val Trp Ile His Gly Asp Ser Glu Glu Asn
            260                 265                 270

Lys Glu Ile Ile Leu Gln Gly Leu Lys His Leu Asn Arg Ala Val His
        275                 280                 285

Glu Asp Ile Val Ala Val Glu Leu Leu Pro Lys Ser Gln Trp Val Ala
    290                 295                 300

Pro Ser Ser Val Val Leu His Asp Glu Gly Gln Asn Glu Glu Asp Val
305                 310                 315                 320

Glu Lys Glu Glu Glu Thr Glu Arg Met Leu Lys Thr Ala Val Ser Glu
                325                 330                 335

Lys Met Leu Lys Pro Thr Gly Arg Val Val Gly Ile Ile Lys Arg Asn
            340                 345                 350

Trp Arg Pro Tyr Cys Gly Met Leu Ser Lys Ser Asp Ile Lys Glu Ser
        355                 360                 365

Arg Arg His Leu Phe Thr Pro Ala Asp Lys Arg Ile Pro Arg Ile Arg
    370                 375                 380

Ile Glu Thr Arg Gln Ala Ser Thr Leu Glu Gly Arg Arg Ile Ile Val
385                 390                 395                 400

Ala Ile Asp Gly Trp Pro Arg Asn Ser Arg Tyr Pro Asn Gly His Phe
                405                 410                 415

Val Arg Asn Leu Gly Asp Val Gly Glu Lys Glu Thr Glu Thr Glu Val
            420                 425                 430

Leu Leu Leu Glu His Asp Val Pro His Gln Pro Phe Ser Gln Ala Val
        435                 440                 445

Leu Ser Phe Leu Pro Lys Met Pro Trp Ser Ile Thr Glu Lys Asp Met
    450                 455                 460
```

```
Lys Asn Arg Glu Asp Leu Arg His Leu Cys Ile Cys Ser Val Asp Pro
465                 470                 475                 480

Pro Gly Cys Thr Asp Ile Asp Asp Ala Leu His Cys Arg Glu Leu Glu
            485                 490                 495

Asn Gly Asn Leu Glu Val Gly Val His Ile Ala Asp Val Ser His Phe
            500                 505                 510

Ile Arg Pro Gly Asn Ala Leu Asp Gln Glu Ser Ala Arg Arg Gly Thr
        515                 520                 525

Thr Val Tyr Leu Cys Glu Lys Arg Ile Asp Met Val Pro Glu Leu Leu
        530                 535                 540

Ser Ser Asn Leu Cys Ser Leu Lys Cys Asp Val Asp Arg Leu Ala Phe
545                 550                 555                 560

Ser Cys Ile Trp Glu Met Asn His Asn Ala Glu Ile Leu Lys Thr Lys
            565                 570                 575

Phe Thr Lys Ser Val Ile Asn Ser Lys Ala Ser Leu Thr Tyr Ala Glu
            580                 585                 590

Ala Gln Leu Arg Ile Asp Ser Ala Asn Met Asn Asp Asp Ile Thr Thr
        595                 600                 605

Ser Leu Arg Gly Leu Asn Lys Leu Ala Lys Ile Leu Lys Lys Arg Arg
        610                 615                 620

Ile Glu Lys Gly Ala Leu Thr Leu Ser Ser Pro Glu Val Arg Phe His
625                 630                 635                 640

Met Asp Ser Glu Thr His Asp Pro Ile Asp Leu Gln Thr Lys Glu Leu
            645                 650                 655

Arg Glu Thr Asn Ser Met Val Glu Glu Phe Met Leu Leu Ala Asn Ile
            660                 665                 670

Ser Val Ala Lys Lys Ile His Glu Glu Phe Ser Glu His Ala Leu Leu
        675                 680                 685

Arg Lys His Pro Ala Pro Pro Ser Asn Tyr Glu Ile Leu Val Lys
        690                 695                 700

Ala Ala Arg Ser Arg Asn Leu Glu Ile Lys Thr Asp Thr Ala Lys Ser
705                 710                 715                 720

Leu Ala Glu Ser Leu Asp Gln Ala Glu Ser Pro Thr Phe Pro Tyr Leu
            725                 730                 735

Asn Thr Leu Leu Arg Ile Leu Ala Thr Arg Cys Met Met Gln Ala Val
            740                 745                 750

Tyr Phe Cys Ser Gly Met Asp Asn Asp Phe His His Tyr Gly Leu Ala
        755                 760                 765

Ser Pro Ile Tyr Thr His Phe Thr Ser Pro Ile Arg Arg Tyr Ala Asp
        770                 775                 780

Val Ile Val His Arg Leu Leu Ala Val Ala Ile Gly Ala Asp Cys Thr
785                 790                 795                 800

Tyr Pro Glu Leu Thr Asp Lys His Lys Leu Ala Asp Ile Cys Lys Asn
            805                 810                 815

Leu Asn Phe Arg His Lys Met Ala Gln Tyr Ala Gln Arg Ala Ser Val
            820                 825                 830

Ala Phe His Thr Gln Leu Phe Phe Lys Ser Lys Gly Ile Val Ser Glu
        835                 840                 845

Glu Ala Tyr Ile Leu Phe Val Arg Lys Asn Ala Ile Val Val Leu Ile
        850                 855                 860

Pro Lys Tyr Gly Leu Glu Gly Thr Val Phe Phe Glu Glu Lys Asp Lys
865                 870                 875                 880

Pro Asn Pro Gln Leu Ile Tyr Asp Asp Glu Ile Pro Ser Leu Lys Ile
```

```
                    885                 890                 895
Glu Asp Thr Val Phe His Val Phe Asp Lys Val Lys Val Lys Ile Met
                900                 905                 910

Leu Asp Ser Ser Asn Leu Gln His Gln Lys Ile Arg Met Ser Leu Val
                915                 920                 925

Glu Pro Gln Ile Pro Gly Ile Ser Ile Pro Thr Asp Thr Ser Asn Met
            930                 935                 940

Asp Leu Asn Gly Pro Lys Lys Lys Met Lys Leu Gly Lys
945                 950                 955

<210> SEQ ID NO 2
<211> LENGTH: 1001
<212> TYPE: PRT
<213> ORGANISM: Saccharomyces cerevisiae

<400> SEQUENCE: 2

Met Ser Val Pro Ala Ile Ala Pro Arg Arg Lys Arg Leu Ala Asp Gly
1               5                   10                  15

Leu Ser Val Thr Gln Lys Val Phe Val Arg Ser Arg Asn Gly Gly Ala
                20                  25                  30

Thr Lys Ile Val Arg Glu His Tyr Leu Arg Ser Asp Ile Pro Cys Leu
            35                  40                  45

Ser Arg Ser Cys Thr Lys Cys Pro Gln Ile Val Val Pro Asp Ala Gln
        50                  55                  60

Asn Glu Leu Pro Lys Phe Ile Leu Ser Asp Ser Pro Leu Glu Leu Ser
65                  70                  75                  80

Ala Pro Ile Gly Lys His Tyr Val Val Leu Asp Thr Asn Val Val Leu
                85                  90                  95

Gln Ala Ile Asp Leu Leu Glu Asn Pro Asn Cys Phe Phe Asp Val Ile
            100                 105                 110

Val Pro Gln Ile Val Leu Asp Glu Val Arg Asn Lys Ser Tyr Pro Val
        115                 120                 125

Tyr Thr Arg Leu Arg Thr Leu Cys Arg Asp Ser Asp Asp His Lys Arg
    130                 135                 140

Phe Ile Val Phe His Asn Glu Phe Ser Glu His Thr Phe Val Glu Arg
145                 150                 155                 160

Leu Pro Asn Glu Thr Ile Asn Asp Arg Asn Asp Arg Ala Ile Arg Lys
                165                 170                 175

Thr Cys Gln Trp Tyr Ser Glu His Leu Lys Pro Tyr Asp Ile Asn Val
            180                 185                 190

Val Leu Val Thr Asn Asp Arg Leu Asn Arg Glu Ala Ala Thr Lys Glu
        195                 200                 205

Val Glu Ser Asn Ile Ile Thr Lys Ser Leu Val Gln Tyr Ile Glu Leu
    210                 215                 220

Leu Pro Asn Ala Asp Asp Ile Arg Asp Ser Ile Pro Gln Met Asp Ser
225                 230                 235                 240

Phe Asp Lys Asp Leu Glu Arg Asp Thr Phe Ser Asp Phe Thr Phe Pro
                245                 250                 255

Glu Tyr Tyr Ser Thr Ala Arg Val Met Gly Gly Leu Lys Asn Gly Val
            260                 265                 270

Leu Tyr Gln Gly Asn Ile Gln Ile Ser Glu Tyr Asn Phe Leu Glu Gly
        275                 280                 285

Ser Val Ser Leu Pro Arg Phe Ser Lys Pro Val Leu Ile Val Gly Gln
    290                 295                 300
```

-continued

```
Lys Asn Leu Asn Arg Ala Phe Asn Gly Asp Gln Val Ile Val Glu Leu
305                 310                 315                 320

Leu Pro Gln Ser Glu Trp Lys Ala Pro Ser Ser Ile Val Leu Asp Ser
            325                 330                 335

Glu His Phe Asp Val Asn Asp Asn Pro Asp Ile Glu Ala Gly Asp Asp
                340                 345                 350

Asp Asp Asn Asn Glu Ser Ser Ser Asn Thr Thr Val Ile Ser Asp Lys
            355                 360                 365

Gln Arg Arg Leu Leu Ala Lys Asp Ala Met Ile Ala Gln Arg Ser Lys
        370                 375                 380

Lys Ile Gln Pro Thr Ala Lys Val Val Tyr Ile Gln Arg Arg Ser Trp
385                 390                 395                 400

Arg Gln Tyr Val Gly Gln Leu Ala Pro Ser Ser Val Asp Pro Gln Ser
                405                 410                 415

Ser Ser Thr Gln Asn Val Phe Val Ile Leu Met Asp Lys Cys Leu Pro
            420                 425                 430

Lys Val Arg Ile Arg Thr Arg Arg Ala Ala Glu Leu Leu Asp Lys Arg
        435                 440                 445

Ile Val Ile Ser Ile Asp Ser Trp Pro Thr Thr His Lys Tyr Pro Leu
450                 455                 460

Gly His Phe Val Arg Asp Leu Gly Thr Ile Glu Ser Ala Gln Ala Glu
465                 470                 475                 480

Thr Glu Ala Leu Leu Leu Glu His Asp Val Glu Tyr Arg Pro Phe Ser
                485                 490                 495

Lys Lys Val Leu Glu Cys Leu Pro Ala Glu Gly His Asp Trp Lys Ala
            500                 505                 510

Pro Thr Lys Leu Asp Asp Pro Glu Ala Val Ser Lys Asp Pro Leu Leu
        515                 520                 525

Thr Lys Arg Lys Asp Leu Arg Asp Lys Leu Ile Cys Ser Ile Asp Pro
    530                 535                 540

Pro Gly Cys Val Asp Ile Asp Asp Ala Leu His Ala Lys Lys Leu Pro
545                 550                 555                 560

Asn Gly Asn Trp Glu Val Gly Val His Ile Ala Asp Val Thr His Phe
                565                 570                 575

Val Lys Pro Gly Thr Ala Leu Asp Ala Glu Gly Ala Ala Arg Gly Thr
            580                 585                 590

Ser Val Tyr Leu Val Asp Lys Arg Ile Asp Met Leu Pro Met Leu Leu
        595                 600                 605

Gly Thr Asp Leu Cys Ser Leu Lys Pro Tyr Val Asp Arg Phe Ala Phe
    610                 615                 620

Ser Val Ile Trp Glu Leu Asp Asp Ser Ala Asn Ile Val Asn Val Asn
625                 630                 635                 640

Phe Met Lys Ser Val Ile Arg Ser Arg Glu Ala Phe Ser Tyr Glu Gln
                645                 650                 655

Ala Gln Leu Arg Ile Asp Asp Lys Thr Gln Asn Asp Glu Leu Thr Met
            660                 665                 670

Gly Met Arg Ala Leu Leu Lys Leu Ser Val Lys Leu Gln Lys Arg
        675                 680                 685

Leu Glu Ala Gly Ala Leu Leu Ala Ser Pro Glu Val Lys Val His
    690                 695                 700

Met Asp Ser Glu Thr Ser Asp Pro Asn Glu Val Glu Ile Lys Lys Leu
705                 710                 715                 720

Leu Ala Thr Asn Ser Leu Val Glu Glu Phe Met Leu Leu Ala Asn Ile
```

725                 730                 735
Ser Val Ala Arg Lys Ile Tyr Asp Ala Phe Pro Gln Thr Ala Met Leu
        740                 745                 750

Arg Arg His Ala Ala Pro Pro Ser Thr Asn Phe Glu Ile Leu Asn Glu
        755                 760                 765

Met Leu Asn Thr Arg Lys Asn Met Ser Ile Ser Leu Glu Ser Ser Lys
        770                 775                 780

Ala Leu Ala Asp Ser Leu Asp Arg Cys Val Asp Pro Glu Asp Pro Tyr
785                 790                 795                 800

Phe Asn Thr Leu Val Arg Ile Met Ser Thr Arg Cys Met Met Ala Ala
                805                 810                 815

Gln Tyr Phe Tyr Ser Gly Ala Tyr Ser Tyr Pro Asp Phe Arg His Tyr
        820                 825                 830

Gly Leu Ala Val Asp Ile Tyr Thr His Phe Thr Ser Pro Ile Arg Arg
        835                 840                 845

Tyr Cys Asp Val Val Ala His Arg Gln Leu Ala Gly Ala Ile Gly Tyr
850                 855                 860

Glu Pro Leu Ser Leu Thr His Arg Asp Lys Asn Lys Met Asp Met Ile
865                 870                 875                 880

Cys Arg Asn Ile Asn Arg Lys His Arg Asn Ala Gln Phe Ala Gly Arg
                885                 890                 895

Ala Ser Ile Glu Tyr Tyr Val Gly Gln Val Met Arg Asn Asn Glu Ser
        900                 905                 910

Thr Glu Thr Gly Tyr Val Ile Lys Val Phe Asn Asn Gly Ile Val Val
        915                 920                 925

Leu Val Pro Lys Phe Gly Val Glu Gly Leu Ile Arg Leu Asp Asn Leu
930                 935                 940

Thr Glu Asp Pro Asn Ser Ala Ala Phe Asp Glu Val Glu Tyr Lys Leu
945                 950                 955                 960

Thr Phe Val Pro Thr Asn Ser Asp Lys Pro Arg Asp Val Tyr Val Phe
                965                 970                 975

Asp Lys Val Glu Val Gln Val Arg Ser Val Met Asp Pro Ile Thr Ser
        980                 985                 990

Lys Arg Lys Ala Glu Leu Leu Leu   Lys
        995                 1000

<210> SEQ ID NO 3
<211> LENGTH: 23
<212> TYPE: DNA
<213> ORGANISM: artificial
<220> FEATURE:
<223> OTHER INFORMATION: primer ADZKD106

<400> SEQUENCE: 3
cggtcatatg agagtgtgtt gcg                                           23

<210> SEQ ID NO 4
<211> LENGTH: 25
<212> TYPE: DNA
<213> ORGANISM: artificial
<220> FEATURE:
<223> OTHER INFORMATION: primer ADZKD110

<400> SEQUENCE: 4
gagaatttgt attttcaggg tgagc                                         25

<210> SEQ ID NO 5

<211> LENGTH: 25
<212> TYPE: DNA
<213> ORGANISM: artificial
<220> FEATURE:
<223> OTHER INFORMATION: primer ADZKD111

<400> SEQUENCE: 5
gctcaccctg aaaatacaaa ttctc                                              25

<210> SEQ ID NO 6
<211> LENGTH: 50
<212> TYPE: DNA
<213> ORGANISM: artificial
<220> FEATURE:
<223> OTHER INFORMATION: primer ADZKD107

<400> SEQUENCE: 6
agtggtttag tggtaaaatc aacgttgcc atcgttgggc ccccggttcg                    50

<210> SEQ ID NO 7
<211> LENGTH: 42
<212> TYPE: DNA
<213> ORGANISM: artificial
<220> FEATURE:
<223> OTHER INFORMATION: primer S477Rfor

<400> SEQUENCE: 7
tgtgtatctg cagagtagac ccaccaggat gtactgatat ag                           42

<210> SEQ ID NO 8
<211> LENGTH: 41
<212> TYPE: DNA
<213> ORGANISM: artificial
<220> FEATURE:
<223> OTHER INFORMATION: primer S477Rrev

<400> SEQUENCE: 8
ggtctactct gcagatacac agatgcctca ggtcttctcg g                            41

<210> SEQ ID NO 9
<211> LENGTH: 41
<212> TYPE: DNA
<213> ORGANISM: artificial
<220> FEATURE:
<223> OTHER INFORMATION: primer V504Gfo

<400> SEQUENCE: 9
aggttggtgg ccatattgct gatgtgagcc attttattag g                            41

<210> SEQ ID NO 10
<211> LENGTH: 42
<212> TYPE: DNA
<213> ORGANISM: artificial
<220> FEATURE:
<223> OTHER INFORMATION: primer cV504Grev

<400> SEQUENCE: 10
agcaatatgg ccaccaacct ccaaatttcc attttcgagt tc                           42

<210> SEQ ID NO 11
<211> LENGTH: 43
<212> TYPE: DNA
<213> ORGANISM: artificial
<220> FEATURE:
<223> OTHER INFORMATION: primer A524Pfor

<400> SEQUENCE: 11
agaatcacct aggagaggaa caactgtgta tctttgtgaa aag                43

<210> SEQ ID NO 12
<211> LENGTH: 41
<212> TYPE: DNA
<213> ORGANISM: artificial
<220> FEATURE:
<223> OTHER INFORMATION: primer A524Prev

<400> SEQUENCE: 12
ttcctctcct aggtgattct tgatccaagg catttcctgg c                  41

<210> SEQ ID NO 13
<211> LENGTH: 41
<212> TYPE: DNA
<213> ORGANISM: artificial
<220> FEATURE:
<223> OTHER INFORMATION: primer G766Rfor

<400> SEQUENCE: 13
catcactacc ggttagcgtc tccaatatac acacatttta c                  41

<210> SEQ ID NO 14
<211> LENGTH: 43
<212> TYPE: DNA
<213> ORGANISM: artificial
<220> FEATURE:
<223> OTHER INFORMATION: primer G766Rrev

<400> SEQUENCE: 14
gacgctaacc ggtagtgatg aaaatcatta tccattccag aac                43

<210> SEQ ID NO 15
<211> LENGTH: 43
<212> TYPE: DNA
<213> ORGANISM: artificial
<220> FEATURE:
<223> OTHER INFORMATION: primer R780Kfor

<400> SEQUENCE: 15
cccattaaac gttacgcaga tgtcattgtt catcggcttt tgg                43

<210> SEQ ID NO 16
<211> LENGTH: 44
<212> TYPE: DNA
<213> ORGANISM: artificial
<220> FEATURE:
<223> OTHER INFORMATION: primer R780Krev

<400> SEQUENCE: 16
tctgcgtaac gtttaatggg tgaagtaaaa tgtgtgtata ttgg               44

<210> SEQ ID NO 17
<211> LENGTH: 52
<212> TYPE: DNA
<213> ORGANISM: artificial
<220> FEATURE:
<223> OTHER INFORMATION: primer I845Vfor

<400> SEQUENCE: 17
caaaggagta gtaagtgaag aggcctatat tttatttgta agaaagaatg cc       52

<210> SEQ ID NO 18
<211> LENGTH: 52
<212> TYPE: DNA

```
<213> ORGANISM: artificial
<220> FEATURE:
<223> OTHER INFORMATION: primer I845Vrev

<400> SEQUENCE: 18
aaaatatagg cctcttcact tactactcct ttgcttttga agaataactg gg            52

<210> SEQ ID NO 19
<211> LENGTH: 20
<212> TYPE: DNA
<213> ORGANISM: artificial
<220> FEATURE:
<223> OTHER INFORMATION: primer SumoF

<400> SEQUENCE: 19
tcatactgtc aaagacaggg                                                20

<210> SEQ ID NO 20
<211> LENGTH: 22
<212> TYPE: DNA
<213> ORGANISM: artificial
<220> FEATURE:
<223> OTHER INFORMATION: primer HD3F883

<400> SEQUENCE: 20
gaagatattg tggctgtgga gc                                             22

<210> SEQ ID NO 21
<211> LENGTH: 22
<212> TYPE: DNA
<213> ORGANISM: artificial
<220> FEATURE:
<223> OTHER INFORMATION: primer HD3F1848

<400> SEQUENCE: 21
ccgtggactg aataaactag cc                                             22

<210> SEQ ID NO 22
<211> LENGTH: 22
<212> TYPE: DNA
<213> ORGANISM: artificial
<220> FEATURE:
<223> OTHER INFORMATION: primer HD3F2429

<400> SEQUENCE: 22
tgacagacaa acacaagctt gc                                             22

<210> SEQ ID NO 23
<211> LENGTH: 22
<212> TYPE: DNA
<213> ORGANISM: artificial
<220> FEATURE:
<223> OTHER INFORMATION: primer HD3R1021

<400> SEQUENCE: 23
ttacagcagt cttaagcatt cg                                             22

<210> SEQ ID NO 24
<211> LENGTH: 22
<212> TYPE: DNA
<213> ORGANISM: artificial
<220> FEATURE:
<223> OTHER INFORMATION: primer HD3R1592

<400> SEQUENCE: 24
ctggctgatt cttgatccaa gg                                             22
```

<210> SEQ ID NO 25
<211> LENGTH: 22
<212> TYPE: DNA
<213> ORGANISM: artificial
<220> FEATURE:
<223> OTHER INFORMATION: primer HD3R2443

<400> SEQUENCE: 25
tgtgtttgtc tgtcaactct gg                                            22

<210> SEQ ID NO 26
<211> LENGTH: 31
<212> TYPE: RNA
<213> ORGANISM: artificial
<220> FEATURE:
<223> OTHER INFORMATION: oligoribonucleotide ss17-A14

<400> SEQUENCE: 26
ccccaccacc aucacuuaaa aaaaaaaaaa a                                   31

<210> SEQ ID NO 27
<211> LENGTH: 44
<212> TYPE: RNA
<213> ORGANISM: artificial
<220> FEATURE:
<223> OTHER INFORMATION: Oligoribonucleotide ss44

<400> SEQUENCE: 27
cgacuggagc acgaggacac ugacauggac ugaaggagua gaaa                    44

<210> SEQ ID NO 28
<211> LENGTH: 17
<212> TYPE: RNA
<213> ORGANISM: artificial
<220> FEATURE:
<223> OTHER INFORMATION: Oligoribonucleotide compl

<400> SEQUENCE: 28
aagugauggu ggugggg                                                   17

<210> SEQ ID NO 29
<211> LENGTH: 46
<212> TYPE: DNA
<213> ORGANISM: artificial
<220> FEATURE:
<223> OTHER INFORMATION: primer ADZKD134

<400> SEQUENCE: 29
agtgagtaac atcagcaata tggccaccaa cttcccaatt accgtt                  46

<210> SEQ ID NO 30
<211> LENGTH: 46
<212> TYPE: DNA
<213> ORGANISM: artificial
<220> FEATURE:
<223> OTHER INFORMATION: primer ADZKD136

<400> SEQUENCE: 30
tatacagaag tacctcttgc gggcccttcc gcatccaggg cagtgc                  46

<210> SEQ ID NO 31
<211> LENGTH: 45
<212> TYPE: DNA
<213> ORGANISM: artificial
<220> FEATURE:

<223> OTHER INFORMATION: primer ADZKD138

<400> SEQUENCE: 31
tgtgtagata tcaacggcta accggtagtg tctaaagtca ggata          45

<210> SEQ ID NO 32
<211> LENGTH: 47
<212> TYPE: DNA
<213> ORGANISM: artificial
<220> FEATURE:
<223> OTHER INFORMATION: primer ADZKD140

<400> SEQUENCE: 32
atgggccaca acatcacagt aacgtttaat aggtgatgtg aaatgtg        47

<210> SEQ ID NO 33
<211> LENGTH: 46
<212> TYPE: DNA
<213> ORGANISM: artificial
<220> FEATURE:
<223> OTHER INFORMATION: primer ADZKD133

<400> SEQUENCE: 33
aacggtaatt gggaagttgg tggccatatt gctgatgtta ctcact         46

<210> SEQ ID NO 34
<211> LENGTH: 46
<212> TYPE: DNA
<213> ORGANISM: artificial
<220> FEATURE:
<223> OTHER INFORMATION: primer ADZKD135

<400> SEQUENCE: 34
gcactgccct ggatgcggaa gggcccgcaa gaggtacttc tgtata         46

<210> SEQ ID NO 35
<211> LENGTH: 45
<212> TYPE: DNA
<213> ORGANISM: artificial
<220> FEATURE:
<223> OTHER INFORMATION: primer ADZKD137

<400> SEQUENCE: 35
tatcctgact ttagacacta ccggttagcc gttgatatct acaca          45

<210> SEQ ID NO 36
<211> LENGTH: 47
<212> TYPE: DNA
<213> ORGANISM: artificial
<220> FEATURE:
<223> OTHER INFORMATION: primer ADZKD139

<400> SEQUENCE: 36
cacatttcac atcacctatt aaacgttact gtgatgttgt ggcccat        47

<210> SEQ ID NO 37
<211> LENGTH: 20
<212> TYPE: DNA
<213> ORGANISM: artificial
<220> FEATURE:
<223> OTHER INFORMATION: primer ADZKD145

<400> SEQUENCE: 37
ggatgatgtt aattgcttgg                                      20

```
<210> SEQ ID NO 38
<211> LENGTH: 20
<212> TYPE: DNA
<213> ORGANISM: artificial
<220> FEATURE:
<223> OTHER INFORMATION: primer ADZKD146

<400> SEQUENCE: 38
ttgaaactct accaccgacc                                              20

<210> SEQ ID NO 39
<211> LENGTH: 20
<212> TYPE: DNA
<213> ORGANISM: artificial
<220> FEATURE:
<223> OTHER INFORMATION: primer RTADZ-9

<400> SEQUENCE: 39
gagatacatt gtgagggacc                                              20

<210> SEQ ID NO 40
<211> LENGTH: 20
<212> TYPE: DNA
<213> ORGANISM: artificial
<220> FEATURE:
<223> OTHER INFORMATION: primer RTADZ-27

<400> SEQUENCE: 40
atgtcagttc ccgctatcgc                                              20

<210> SEQ ID NO 41
<211> LENGTH: 20
<212> TYPE: DNA
<213> ORGANISM: artificial
<220> FEATURE:
<223> OTHER INFORMATION: primer ADZKD151

<400> SEQUENCE: 41
cgtcgttctt gttaccaacg                                              20

<210> SEQ ID NO 42
<211> LENGTH: 20
<212> TYPE: DNA
<213> ORGANISM: artificial
<220> FEATURE:
<223> OTHER INFORMATION: primer ADZKD152

<400> SEQUENCE: 42
caccgtgatt tccgacaagc                                              20

<210> SEQ ID NO 43
<211> LENGTH: 22
<212> TYPE: DNA
<213> ORGANISM: artificial
<220> FEATURE:
<223> OTHER INFORMATION: primer ADZ1601

<400> SEQUENCE: 43
gcccgcagaa ggccacgatt gg                                           22

<210> SEQ ID NO 44
<211> LENGTH: 22
<212> TYPE: DNA
<213> ORGANISM: artificial
<220> FEATURE:
<223> OTHER INFORMATION: primer RTADZ-68
```

```
<400> SEQUENCE: 44
agggctctct tgaaattgtc tg                                              22

<210> SEQ ID NO 45
<211> LENGTH: 22
<212> TYPE: DNA
<213> ORGANISM: artificial
<220> FEATURE:
<223> OTHER INFORMATION: primer ADZ1603

<400> SEQUENCE: 45
gacaggtgtg tggatcccga ag                                              22

<210> SEQ ID NO 46
<211> LENGTH: 29
<212> TYPE: DNA
<213> ORGANISM: artificial
<220> FEATURE:
<223> OTHER INFORMATION: primer ADZKD141

<400> SEQUENCE: 46
cctaaataga gcattcaacg gtgaccagg                                       29

<210> SEQ ID NO 47
<211> LENGTH: 29
<212> TYPE: DNA
<213> ORGANISM: artificial
<220> FEATURE:
<223> OTHER INFORMATION: primer ADZKD142

<400> SEQUENCE: 47
cctggtcacc gttgaatgct ctatttagg                                       29

<210> SEQ ID NO 48
<211> LENGTH: 19
<212> TYPE: DNA
<213> ORGANISM: artificial
<220> FEATURE:
<223> OTHER INFORMATION: oligonucleotide yeast 7S antisense

<400> SEQUENCE: 48
ggccagcaat ttcaagtta                                                  19

<210> SEQ ID NO 49
<211> LENGTH: 17
<212> TYPE: DNA
<213> ORGANISM: artificial
<220> FEATURE:
<223> OTHER INFORMATION: oligonucleotide yeast 5.8S antisense

<400> SEQUENCE: 49
gcgttgttca tcgatgc                                                    17

<210> SEQ ID NO 50
<211> LENGTH: 16
<212> TYPE: DNA
<213> ORGANISM: artificial
<220> FEATURE:
<223> OTHER INFORMATION: oligonucleotide yeast 5S antisense

<400> SEQUENCE: 50
ctactcggtc aggctc                                                     16

<210> SEQ ID NO 51
<211> LENGTH: 40
```

```
<212> TYPE: DNA
<213> ORGANISM: artificial
<220> FEATURE:
<223> OTHER INFORMATION: primer D3FMluI

<400> SEQUENCE: 51
atatacgcgt gccgccacca tgctcaagtc caagacgttc                           40

<210> SEQ ID NO 52
<211> LENGTH: 63
<212> TYPE: DNA
<213> ORGANISM: artificial
<220> FEATURE:
<223> OTHER INFORMATION: primer D3RB120I

<400> SEQUENCE: 52
gcgcgggccc ttacttgtcg tcgtcgtcct tgtaatctat atcttttcca agcttcatct    60
tct                                                                  63

<210> SEQ ID NO 53
<211> LENGTH: 45
<212> TYPE: DNA
<213> ORGANISM: artificial
<220> FEATURE:
<223> OTHER INFORMATION: primer eGFPFor

<400> SEQUENCE: 53
gcggaattca tatacctagg accatggtga gcaagggcga ggagc                    45

<210> SEQ ID NO 54
<211> LENGTH: 46
<212> TYPE: DNA
<213> ORGANISM: artificial
<220> FEATURE:
<223> OTHER INFORMATION: primer eGFPRev

<400> SEQUENCE: 54
gcgcgtcgac tcactacctc ctcttacttg tacagctcgt ccatgc                   46

<210> SEQ ID NO 55
<211> LENGTH: 20
<212> TYPE: DNA
<213> ORGANISM: artificial
<220> FEATURE:
<223> OTHER INFORMATION: primer hD3r819R

<400> SEQUENCE: 55
cttgttctcc tcggaatctc                                                20

<210> SEQ ID NO 56
<211> LENGTH: 20
<212> TYPE: DNA
<213> ORGANISM: artificial
<220> FEATURE:
<223> OTHER INFORMATION: primer BI16seq1

<400> SEQUENCE: 56
cattctccgc tccatcgttc                                                20

<210> SEQ ID NO 57
<211> LENGTH: 20
<212> TYPE: DNA
<213> ORGANISM: artificial
<220> FEATURE:
<223> OTHER INFORMATION: primer BI16seq2
```

```
<400> SEQUENCE: 57
tccactggtc gactcactac                                              20

<210> SEQ ID NO 58
<211> LENGTH: 20
<212> TYPE: DNA
<213> ORGANISM: artificial
<220> FEATURE:
<223> OTHER INFORMATION: primer GAPDH_F

<400> SEQUENCE: 58
tgcaccacca actgcttagc                                              20

<210> SEQ ID NO 59
<211> LENGTH: 21
<212> TYPE: DNA
<213> ORGANISM: artificial
<220> FEATURE:
<223> OTHER INFORMATION: primer GAPDH_R

<400> SEQUENCE: 59
ggcatggact gtggtcatga g                                            21

<210> SEQ ID NO 60
<211> LENGTH: 20
<212> TYPE: DNA
<213> ORGANISM: artificial
<220> FEATURE:
<223> OTHER INFORMATION: primer 7SL_F

<400> SEQUENCE: 60
tcgggtgtcc gcactaagtt                                              20

<210> SEQ ID NO 61
<211> LENGTH: 19
<212> TYPE: DNA
<213> ORGANISM: artificial
<220> FEATURE:
<223> OTHER INFORMATION: primer 7SL-R

<400> SEQUENCE: 61
tggctattca caggcgcga                                               19

<210> SEQ ID NO 62
<211> LENGTH: 19
<212> TYPE: DNA
<213> ORGANISM: artificial
<220> FEATURE:
<223> OTHER INFORMATION: oligonucleotide human 5.8S rRNA precursor
      antisense

<400> SEQUENCE: 62
gcgattgatc ggcaagcga                                               19

<210> SEQ ID NO 63
<211> LENGTH: 32
<212> TYPE: DNA
<213> ORGANISM: artificial
<220> FEATURE:
<223> OTHER INFORMATION: oligonucleotide human 5.8S rRNA antisense

<400> SEQUENCE: 63
tcctgcaatt cacattaatt ctcgcagcta gc                                32

<210> SEQ ID NO 64
```

```
<211> LENGTH: 22
<212> TYPE: DNA
<213> ORGANISM: artificial
<220> FEATURE:
<223> OTHER INFORMATION: oligonucleotide human 5S rRNA antisense oligo

<400> SEQUENCE: 64
catccaagta ctaaccaggc cc                                          22

<210> SEQ ID NO 65
<211> LENGTH: 30
<212> TYPE: DNA
<213> ORGANISM: artificial
<220> FEATURE:
<223> OTHER INFORMATION: oligonucleotide human tRNA AsnGTT antisense
      oligo

<400> SEQUENCE: 65
accaaccttt cggttaacag ccgaacgcgc                                  30

<210> SEQ ID NO 66
<211> LENGTH: 30
<212> TYPE: DNA
<213> ORGANISM: artificial
<220> FEATURE:
<223> OTHER INFORMATION: oligonucleotide human tRNA AspGTC antisense
      oligo

<400> SEQUENCE: 66
cggtctcccg cgtgacaggc ggggatactc                                  30

<210> SEQ ID NO 67
<211> LENGTH: 30
<212> TYPE: DNA
<213> ORGANISM: artificial
<220> FEATURE:
<223> OTHER INFORMATION: oligonucleotide human tRNA HisGTG antisense
      oligo

<400> SEQUENCE: 67
cgaggttgct gcggccacaa cgcagagtac                                  30

<210> SEQ ID NO 68
<211> LENGTH: 30
<212> TYPE: DNA
<213> ORGANISM: artificial
<220> FEATURE:
<223> OTHER INFORMATION: oligonucleotide human tRNA TrpCCA antisense
      oligo

<400> SEQUENCE: 68
cgcaaccttc tgatctggag tcagacgcgc                                  30

<210> SEQ ID NO 69
<211> LENGTH: 30
<212> TYPE: DNA
<213> ORGANISM: artificial
<220> FEATURE:
<223> OTHER INFORMATION: oligonucleotide human tRNA TyrGTA antisense
      oligo

<400> SEQUENCE: 69
gacctaagga tctacagtcc tccgctctac                                  30

<210> SEQ ID NO 70
<211> LENGTH: 30
<212> TYPE: DNA
```

-continued

```
<213> ORGANISM: artificial
<220> FEATURE:
<223> OTHER INFORMATION: oligonucleotide human tRNA LysTTT (1,2)
      antisense oligo

<400> SEQUENCE: 70
gaccctcaga ttaaaagtct gatgctctac                                      30

<210> SEQ ID NO 71
<211> LENGTH: 30
<212> TYPE: DNA
<213> ORGANISM: artificial
<220> FEATURE:
<223> OTHER INFORMATION: oligonucleotide human tRNA PheGAA antisense
      oligo

<400> SEQUENCE: 71
ggacctttag atcttcagtc taacgctctc                                      30

<210> SEQ ID NO 72
<211> LENGTH: 30
<212> TYPE: DNA
<213> ORGANISM: artificial
<220> FEATURE:
<223> OTHER INFORMATION: oligonucleotide human tRNA CysGCA antisense
      oligo

<400> SEQUENCE: 72
gggacctctt gatctgcagt caaatgctct                                      30

<210> SEQ ID NO 73
<211> LENGTH: 22
<212> TYPE: DNA
<213> ORGANISM: artificial
<220> FEATURE:
<223> OTHER INFORMATION: oligonucleotide human RNase P RNA antisense
      oligo

<400> SEQUENCE: 73
atgggcggag gagagtagtc tg                                              22

<210> SEQ ID NO 74
<211> LENGTH: 21
<212> TYPE: DNA
<213> ORGANISM: artificial
<220> FEATURE:
<223> OTHER INFORMATION: oligonucleotide human RNase MRP RNA antisense
      oligo

<400> SEQUENCE: 74
gccgcgctga gaatgagccc c                                               21

<210> SEQ ID NO 75
<211> LENGTH: 30
<212> TYPE: DNA
<213> ORGANISM: artificial
<220> FEATURE:
<223> OTHER INFORMATION: oligonucleotide human U2 snRNA antisense oligo

<400> SEQUENCE: 75
gggtgcaccg ttcctggagg tactgcaata                                      30

<210> SEQ ID NO 76
<211> LENGTH: 30
<212> TYPE: DNA
<213> ORGANISM: artificial
<220> FEATURE:
```

<223> OTHER INFORMATION: oligonucleotide human U5 snRNA antisense oligo

<400> SEQUENCE: 76
ttgggttaag actcagagtt gttcctctcc                                    30

<210> SEQ ID NO 77
<211> LENGTH: 20
<212> TYPE: DNA
<213> ORGANISM: artificial
<220> FEATURE:
<223> OTHER INFORMATION: oligonucleotide human U6 snRNA antisense oligo

<400> SEQUENCE: 77
gaacgcttca cgaatttgcg                                               20

<210> SEQ ID NO 78
<211> LENGTH: 30
<212> TYPE: DNA
<213> ORGANISM: artificial
<220> FEATURE:
<223> OTHER INFORMATION: oligonucleotide human U3 snoRNA antisense oligo

<400> SEQUENCE: 78
accactcaga ccgcgttctc tccctctcac                                    30

<210> SEQ ID NO 79
<211> LENGTH: 20
<212> TYPE: DNA
<213> ORGANISM: artificial
<220> FEATURE:
<223> OTHER INFORMATION: primer GAPDH Forward

<400> SEQUENCE: 79
gtcagccgca tcttcttttg                                               20

<210> SEQ ID NO 80
<211> LENGTH: 20
<212> TYPE: DNA
<213> ORGANISM: artificial
<220> FEATURE:
<223> OTHER INFORMATION: primer GAPDH Reverse

<400> SEQUENCE: 80
gcgcccaata cgaccaaatc                                               20

<210> SEQ ID NO 81
<211> LENGTH: 20
<212> TYPE: DNA
<213> ORGANISM: artificial
<220> FEATURE:
<223> OTHER INFORMATION: primer 40-2b PROM Forward

<400> SEQUENCE: 81
gggagtctaa ggaaaaggag                                               20

<210> SEQ ID NO 82
<211> LENGTH: 20
<212> TYPE: DNA
<213> ORGANISM: artificial
<220> FEATURE:
<223> OTHER INFORMATION: primer 40-2b PROM Reverse

<400> SEQUENCE: 82
cagtgaaagg agagcgtatc                                               20

```
<210> SEQ ID NO 83
<211> LENGTH: 20
<212> TYPE: DNA
<213> ORGANISM: artificial
<220> FEATURE:
<223> OTHER INFORMATION: primer 40-13 PROMPT Forward

<400> SEQUENCE: 83
ggaaatagtg gagaaaagca                                              20

<210> SEQ ID NO 84
<211> LENGTH: 20
<212> TYPE: DNA
<213> ORGANISM: artificial
<220> FEATURE:
<223> OTHER INFORMATION: primer 40-13 PROMPT Reverse

<400> SEQUENCE: 84
catttttgaa ggaacggtag                                              20

<210> SEQ ID NO 85
<211> LENGTH: 20
<212> TYPE: DNA
<213> ORGANISM: artificial
<220> FEATURE:
<223> OTHER INFORMATION: primer 40-33 PROMPT  Forward

<400> SEQUENCE: 85
ctggcctagc taaagtctca                                              20

<210> SEQ ID NO 86
<211> LENGTH: 20
<212> TYPE: DNA
<213> ORGANISM: artificial
<220> FEATURE:
<223> OTHER INFORMATION: primer 40-33 PROMPT Reverse

<400> SEQUENCE: 86
tctgctccta gctctcagtc                                              20

<210> SEQ ID NO 87
<211> LENGTH: 20
<212> TYPE: DNA
<213> ORGANISM: artificial
<220> FEATURE:
<223> OTHER INFORMATION: primer 40-52 PROMPT Forward

<400> SEQUENCE: 87
agttccaaga aaccacacac                                              20

<210> SEQ ID NO 88
<211> LENGTH: 20
<212> TYPE: DNA
<213> ORGANISM: artificial
<220> FEATURE:
<223> OTHER INFORMATION: primer 40-52 PROMPT Reverse

<400> SEQUENCE: 88
ggtcgtttga gtggactaac                                              20

<210> SEQ ID NO 89
<211> LENGTH: 20
<212> TYPE: DNA
<213> ORGANISM: artificial
<220> FEATURE:
<223> OTHER INFORMATION: primer 40-13 gene Forward
```

```
<400> SEQUENCE: 89
ggagttgaca gcagagtttt                                           20

<210> SEQ ID NO 90
<211> LENGTH: 20
<212> TYPE: DNA
<213> ORGANISM: artificial
<220> FEATURE:
<223> OTHER INFORMATION: primer 40-13 gene Reverse

<400> SEQUENCE: 90
atgcacttta accaggtttg                                           20

<210> SEQ ID NO 91
<211> LENGTH: 20
<212> TYPE: DNA
<213> ORGANISM: artificial
<220> FEATURE:
<223> OTHER INFORMATION: primer 40-33 gene Forward

<400> SEQUENCE: 91
ggtgacaact ggtctctgtc                                           20

<210> SEQ ID NO 92
<211> LENGTH: 20
<212> TYPE: DNA
<213> ORGANISM: artificial
<220> FEATURE:
<223> OTHER INFORMATION: primer 40-33 gene Reverse

<400> SEQUENCE: 92
ccgaaagtta ccaaaacatt                                           20

<210> SEQ ID NO 93
<211> LENGTH: 20
<212> TYPE: DNA
<213> ORGANISM: artificial
<220> FEATURE:
<223> OTHER INFORMATION: primer 40-52 gene Forward

<400> SEQUENCE: 93
aaaatgagac tggccactaa                                           20

<210> SEQ ID NO 94
<211> LENGTH: 20
<212> TYPE: DNA
<213> ORGANISM: artificial
<220> FEATURE:
<223> OTHER INFORMATION: primer 40-52 gene  Reverse

<400> SEQUENCE: 94
gatgtgggat tctctcaaac                                           20

<210> SEQ ID NO 95
<211> LENGTH: 22
<212> TYPE: DNA
<213> ORGANISM: artificial
<220> FEATURE:
<223> OTHER INFORMATION: primer mtATP6/8 Forward

<400> SEQUENCE: 95
ccatcagcct actcattcaa cc                                        22

<210> SEQ ID NO 96
<211> LENGTH: 22
```

```
<212> TYPE: DNA
<213> ORGANISM: artificial
<220> FEATURE:
<223> OTHER INFORMATION: primer mtATP6/8 Reverse

<400> SEQUENCE: 96
gcgacagcga tttctaggat ag                                              22

<210> SEQ ID NO 97
<211> LENGTH: 43
<212> TYPE: DNA
<213> ORGANISM: artificial
<220> FEATURE:
<223> OTHER INFORMATION: primer D3PINF

<400> SEQUENCE: 97
aggaataacc gggcgattcg agtagcagca aaatggtaca atg                       43

<210> SEQ ID NO 98
<211> LENGTH: 42
<212> TYPE: DNA
<213> ORGANISM: artificial
<220> FEATURE:
<223> OTHER INFORMATION: primer D3PINR

<400> SEQUENCE: 98
tcgaatcgcc cggttattcc tgtcattagc attttctccc tg                        42
```